US012201592B2

(12) United States Patent
Reuveni et al.

(10) Patent No.: US 12,201,592 B2
(45) Date of Patent: *Jan. 21, 2025

(54) COMBINATIONS OF IRS/STAT3 DUAL MODULATORS AND ANTI-CANCER AGENTS FOR TREATING CANCER

(71) Applicant: TYRNOVO LTD., Tel Aviv (IL)

(72) Inventors: Hadas Reuveni, Har Adar (IL); Izhak Haviv, Rosh Pina (IL); Lana Kupershmidt, Kiryat Bialik (IL)

(73) Assignee: TYRNOVO LTD., Tel Aviv (IL)

( * ) Notice: Subject to any disclaimer, the term of this patent is extended or adjusted under 35 U.S.C. 154(b) by 649 days.

This patent is subject to a terminal disclaimer.

(21) Appl. No.: 17/159,798

(22) Filed: Jan. 27, 2021

(65) Prior Publication Data

US 2021/0220297 A1    Jul. 22, 2021

Related U.S. Application Data

(63) Continuation of application No. 15/548,915, filed as application No. PCT/IL2016/050134 on Feb. 4, 2016, now Pat. No. 10,912,745.

(60) Provisional application No. 62/136,530, filed on Mar. 22, 2015, provisional application No. 62/112,257, filed on Feb. 5, 2015.

(51) Int. Cl.
| *A61K 31/165* | (2006.01) |
| *A61K 31/436* | (2006.01) |
| *A61K 31/4375* | (2006.01) |
| *A61K 31/505* | (2006.01) |
| *A61K 31/517* | (2006.01) |
| *A61K 31/519* | (2006.01) |
| *A61K 39/395* | (2006.01) |
| *C07K 16/28* | (2006.01) |

(52) U.S. Cl.
CPC .......... *A61K 31/165* (2013.01); *A61K 31/436* (2013.01); *A61K 31/4375* (2013.01); *A61K 31/505* (2013.01); *A61K 31/517* (2013.01); *A61K 31/519* (2013.01); *A61K 39/39558* (2013.01); *C07K 16/2863* (2013.01); *C07K 2317/24* (2013.01); *C07K 2317/76* (2013.01)

(58) Field of Classification Search
CPC .......................... A61K 31/055; A61K 2300/00
See application file for complete search history.

(56) References Cited

U.S. PATENT DOCUMENTS

| 5,217,999 | A | 6/1993 | Levitzki |
| 5,302,606 | A | 4/1994 | Spada |
| 5,691,362 | A | 11/1997 | McCormick |
| 5,773,476 | A | 6/1998 | Chen |
| 5,789,427 | A | 8/1998 | Chen |
| 6,020,332 | A | 2/2000 | Li |
| 6,225,335 | B1 | 5/2001 | Tang |
| 6,525,046 | B1 | 2/2003 | Cirillo |
| 8,058,309 | B2 | 11/2011 | Reuveni |
| 2002/0068687 | A1 | 6/2002 | Chen |
| 2004/0127555 | A1 | 7/2004 | Snow |
| 2004/0197335 | A1 | 10/2004 | Slavin |
| 2009/0143397 | A1 | 6/2009 | Kuo |
| 2012/0083528 | A1 | 4/2012 | Reuveni |

FOREIGN PATENT DOCUMENTS

| CN | 1155977 A | 8/1997 |
| CN | 1167568 A | 12/1997 |
| EP | 0860438 B1 | 1/2003 |
| EP | 1340500 A1 | 9/2003 |
| JP | 2005513100 A | 5/2005 |
| JP | 2005516983 A | 6/2005 |
| WO | 95024190 A2 | 9/1995 |
| WO | 97045111 A1 | 12/1997 |
| WO | 97045400 A1 | 12/1997 |
| WO | 99024442 A1 | 5/1999 |
| WO | 00043384 A1 | 7/2000 |
| WO | 01068593 A2 | 9/2001 |
| WO | 03045378 A1 | 6/2003 |
| WO | 03053425 A1 | 7/2003 |
| WO | 03072570 A1 | 9/2003 |
| WO | 2004030627 A2 | 4/2004 |

(Continued)

OTHER PUBLICATIONS

Lowe et al (Advances in Protein Chemistry and Structural Biology, 2011, vol. 84, pp. 41-61) (Year: 2011).*
Brand et al (Cancer Biology & Therapy, 2011, vol. 11, pp. 777-792) (Year: 2011).*
Ullrich & Schlessinger, (1990) Signal transduction by receptors with tyrosine kinase activity. Cell, 61(2), 203-212.
Villanueva et al., (2010) Acquired resistance to BRAF inhibitors mediated by a RAF kinase switch in melanoma can be overcome by cotargeting MEK and IGF-1R/PI3K. Cancer cell, 18(6), 683-695.
Weickhardt et al., (2012) Dual targeting of the epidermal growth factor receptor using the combination of cetuximab and erlotinib: preclinical evaluation and results of the phase II DUX study in chemotherapy-refractory, advanced colorectal cancer. J Clin Oncol 30(13): 1505-1512.

(Continued)

*Primary Examiner* — Karen A. Canella
(74) *Attorney, Agent, or Firm* — ROTHWELL, FIGG, ERNST & MANBECK, P.C.

(57) ABSTRACT

Provided is a treatment of cancer using a dual modulator of Insulin Receptor Substrate (IRS) and signal transducer and activator of transcription 3 (Stat3), as well with other agents. The combination can be used to treat a tumor that has developed resistance to an EGFR inhibitor, EGFR antibody, mTOR inhibitor, MEK inhibitor, mutated B-Raf inhibitor, chemotherapeutic agents, and certain combinations thereof, or to prevent acquired resistance of a tumor to any of said inhibitors or agents, or to prevent tumor recurrence following cease of treatment with any of said inhibitors or agents or a combination thereof. The subject matter further provides a treatment of cancer using combination therapy comprising a dual modulator of IRS and Stat3, in combination with an immunotherapy agent. The combination can be used to sensitize a tumor to immunotherapy.

16 Claims, 22 Drawing Sheets

(56) References Cited

FOREIGN PATENT DOCUMENTS

| | | | |
|---|---|---|---|
| WO | 2005068414 | A1 | 7/2005 |
| WO | 2005077942 | A1 | 8/2005 |
| WO | 2005094376 | A2 | 10/2005 |
| WO | 2007072041 | A1 | 6/2007 |
| WO | 2008028314 | A1 | 3/2008 |
| WO | 2008068751 | A1 | 6/2008 |
| WO | 2009147682 | A1 | 12/2009 |
| WO | 2012090204 | A1 | 7/2012 |
| WO | 2012117396 | A1 | 9/2012 |
| WO | 2014015280 | A1 | 1/2014 |
| WO | 2014189937 | A1 | 11/2014 |

OTHER PUBLICATIONS

Yaish et al., (1988) Blocking of EGF-dependent cell proliferation by EGF receptor kinase inhibitors. Science, 242 (4880), 933-935.

Yamada et al., (1999) Cellular sensitization to cisplatin and carboplatin with decreased removal of platinum-DNA adduct by glucose-regulated stress. Cancer Chemother Pharmacol 44(1): 59-64.

Yamada et al., (2003) Structure-function relationships of vitamin D including ligand recognition by the vitamin D receptor. Med Res Rev 23(1): 89-115.

Yoneda et al., (1991) The antiproliferative effects of tyrosine kinase inhibitors tyrphostins on a human squamous cell carcinoma in vitro and in nude mice. Cancer research, 51(16), 4430-4435.

Yu et al., (2014) Therapeutic strategies utilized in the setting of acquired resistance to EGFR tyrosine kinase inhibitors. Clin Cancer Res 20(23): 5898-5907.

Yuan & Parrill, (2000) QSAR development to describe HIV-1 integrase inhibition. Journal of Molecular Structure: Theochem, 529(1), 273-282.

Philips and Atkins (2015) Therapeutic uses of anti-PD-1 and anti-PD-L1 antibodies. Int Immunol 27(1): 39-46.

Tol et al., (2009) Chemotherapy, bevacizumab, and cetuximab in metastatic colorectal cancer. N Engl J Med 360(6): 563-572. With erratum.

Aaronson, (1991) Growth factors and cancer. Science(Washington), 254(5035), 1146-1153.

Backstrom et al., (1989) Synthesis of some novel potent and selective catechol O-methyltransferase inhibitors. Journal of medicinal chemistry, 32(4), 841-846.

Baserga, (2009) The insulin receptor substrate-1: a biomarker for cancer?. Experimental cell research, 315(5), 727-732.

Berge et al., (1977) Pharmaceutical salts. Journal of pharmaceutical sciences, 66(1), 1-19.

Blum et al., (2000) Substrate competitive inhibitors of IGF-1 receptor kinase. Biochemistry, 39(51), 15705-15712.

Bollag et al., (2010) Clinical efficacy of a RAF inhibitor needs broad target blockade in BRAF-mutant melanoma. Nature 467(7315): 596-599.

Buchwald et al., (1980) Long-term, continuous intravenous heparin administration by an implantable infusion pump in ambulatory patients with recurrent venous thrombosis. Surgery, 88(4), 507-516.

Buck et al., (2008) Feedback mechanisms promote cooperativity for small molecule inhibitors of epidermal and insulin-like growth factor receptors. Cancer research, 68(20), 8322-8332.

Cardone et al., (1998) Regulation of cell death protease caspase-9 by phosphorylation. Science, 282(5392), 1318-1321.

Crose & Linardic, (2011) Receptor tyrosine kinases as therapeutic targets in rhabdomyosarcoma. Sarcoma, 2011.

Douillet et al., (2012) Development of a solvate as an active pharmaceutical ingredient: Developability, crystallisation and isolation challenges. Journal of Crystal Growth 342(1): 2-8.

Flaherty et al., (2010) Inhibition of mutated, activated BRAF in metastatic melanoma. New England Journal of Medicine, 363(9), 809-819.

Gazit et al., (1989) Tyrphostins I: synthesis and biological activity of protein tyrosine kinase inhibitors. Journal of medicinal chemistry, 32(10), 2344-2352.

Gazit et al., (1991) Tyrphostins. II. Heterocyclic and. alpha.—substituted benzylidenemalononitrile tyrphostins as potent Inhibitors of EGF receptor and ErbB2/neu tyrosine kinases. Journal of medicinal chemistry, 34(6), 1896-1907.

Goodson, (1984) Dental Applications. In: Medical Applications of Controlled Release, vol. 2, Applications and Evaluations, R.S. Langer and D.L. Wise, Eds., Boca Raton, FL:CRC Press, pp. 115-138.

Gowthamarajan et al., (2002) Formulation and Dissolution Properties of Meloxicam Solid Dispersion Incorporated Suppositories. Indian J Pharm Sci 64(6): 525-528.

Gray and Haura (2014) Update on third-generation EGFR tyrosine kinase inhibitors. Transl Lung Cancer Res 3(6): 360-362.

Hu et al., (2000) p 0 tumor cells: a model for studying whether mitochondria are targets for rhodamine 123, doxorubicin, and other drugs. Biochemical pharmacology, 60(12), 1897-1905.

Kannappan and Mannemala (2016) Simultaneous enantioseparation and purity determination of chiral switches of amlodipine and atenolol by liquid chromatography. J Pharm Biomed Anal 120: 221-227.

Kaplan et al., (1990) Effects of 2-deoxyglucose on drug-sensitive and drug-resistant human breast cancer cells: toxicity and magnetic resonance spectroscopy studies of metabolism. Cancer research, 50(3), 544-551.

Keniry & Parsons, (2011) mTOR Inhibition, the Second Generation: ATP-Competitive mTOR Inhibitor Initiates Unexpected Receptor Tyrosine Kinase-Driven Feedback Loop. Cancer discovery, 1(3), 203-204.

Kolho et al., (1993) Hepatitis C antibodies in dialysis patients and patients with leukemia. Journal of medical virology, 40(4), 318-321.

Krishnaiah and Khan (2012) Strategies of targeting oral drug delivery systems to the colon and their potential use for the treatment of colorectal cancer. Pharm Dev Technol 17(5): 521-540.

Kurata (2008) Method of Using Gefitinib and Erlotinib. Integrated Medical Practice 57(9): 2278-2281. With English translated abstract.

Langer, (1990) New methods of drug delivery. Science, 1527-1533.

Levitzki & Gazit, (1995) Tyrosine kinase inhibition: an approach to drug development. Science (New York, NY), 267 (5205), 1782-1788.

Levitzki, (1990) Tyrphostins—potential antiproliferative agents and novel molecular tools. Biochemical pharmacology, 40(5), 913-918.

Levitzki, (1992) Tyrphostins: tyrosine kinase blockers as novel antiproliferative agents and dissectors of signal transduction. The FASEB Journal, 6(14), 3275-3282.

Li et al., (2009) Inhibition of the insulin-like growth factor-1 receptor (IGF1R) tyrosine kinase as a novel cancer therapy approach. Journal of medicinal chemistry, 52(16), 4981-5004.

Liu et al., (2001) Hypersensitization of tumor cells to glycolytic inhibitors. Biochemistry, 40(18), 5542-5547.

Liu et al., (2002) Hypoxia increases tumor cell sensitivity to glycolytic inhibitors: a strategy for solid tumor therapy (Model C). Biochemical pharmacology, 64(12), 1745-1751.

Luo and Chen (2014) Recent advances in the development of mutant-selective EGFR inhibitors for non-small cell lung cancer patients with EGFR-TKI resistance. Transl Lung Cancer Res 3(6): 368-369.

Maillet et al., (2008) Aerodynamical, immunological and pharmacological properties of the anticancer antibody cetuximab following nebulization. Pharm Res 25(6): 1318-1326.

Mazumder et al., (1995) Effects of tyrphostins, protein kinase inhibitors, on human immunodeficiency virus type 1 integrase. Biochemistry, 34(46), 15111-15122.

Moeller and Jorgensen (2008) Alternative routes of administration for systemic delivery of protein pharmaceuticals. Drug Discov Today Technol 5(2-3): e89-e94.

Noro et al., (1982) Studies on pharmaceutical drug design for suppositories. II. Rheological properties of emulsion-type suppository bases. Chem Pharm Bull (Tokyo) 30(8): 2906-2911.

(56) References Cited

OTHER PUBLICATIONS

Oliveira et al., (2008) Antineoplastic effect of rapamycin is potentiated by inhibition of IRS-1 signaling in prostate cancer cells xenografts. Journal of cancer research and clinical oncology, 134(8), 833-839.

O'Reilly et al., (2006) mTOR inhibition induces upstream receptor tyrosine kinase signaling and activates Akt. Cancer research, 66(3), 1500-1508.

Posner et al., (1994) Kinetics of inhibition by tyrphostins of the tyrosine kinase activity of the epidermal growth factor receptor and analysis by a new computer program. Molecular pharmacology, 45(4), 673-683.

Ravikumar et al., (2007) Insulin receptor substrate-1 is an important mediator of ovarian cancer cell growth suppression by all-trans retinoic acid. Cancer Res 67(19): 9266-9275.

Reuveni et al., (2013) Therapeutic destruction of insulin receptor substrates for cancer treatment. Cancer Res 73(14): 4383-4394.

Ryan & Goss, (2008) The emerging role of the insulin-like growth factor pathway as a therapeutic target in cancer. The oncologist, 13(1), 16-24.

Saudek et al., (1989) A preliminary trial of the programmable implantable medication system for insulin delivery. New England Journal of Medicine, 321(9), 574-579.

Schlessinger & Ullrich, (1992) Growth factor signaling by receptor tyrosine kinases. Neuron, 9(3), 383-391.

Schlessinger, (1988) Signal transduction by allosteric receptor oligomerization. Trends in biochemical sciences, 13 (11), 443-447.

Smith (2009) Chiral toxicology: it's the same thing . . . only different. Toxicol Sci 110(1): 4-30.

Steiner et al., (2007) ATP non-competitive IGF-1 receptor kinase inhibitors as lead anti-neoplastic and anti-papilloma agents. European journal of pharmacology, 562(1), 1-11.

Sui et al., (2013) Autophagy and chemotherapy resistance: a promising therapeutic target for cancer treatment. Cell Death Dis 4: e838; 12 pages.

Ting & Morris, (1978) Reactivity of autolymphocytotoxic antibodies from dialysis patients with lymphocytes from chronic lymphocytic leukemia (CLL) patients. Transplantation, 25(1), 31-33.

Treat et al., (1989) in Liposomes in the Therapy of Infectious Disease and Cancer. Lopez- Berestein and Fidler (eds.), Liss, NY, 353-365.

\* cited by examiner

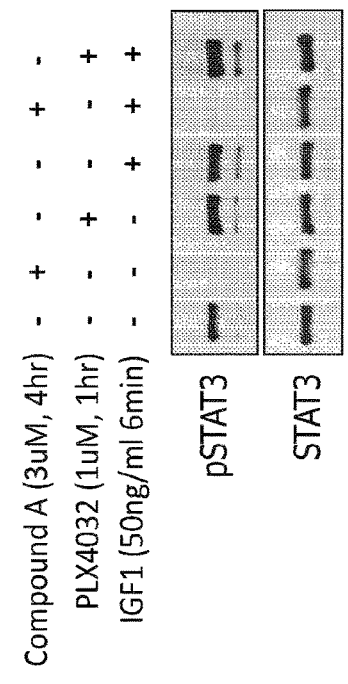
Figure 8A
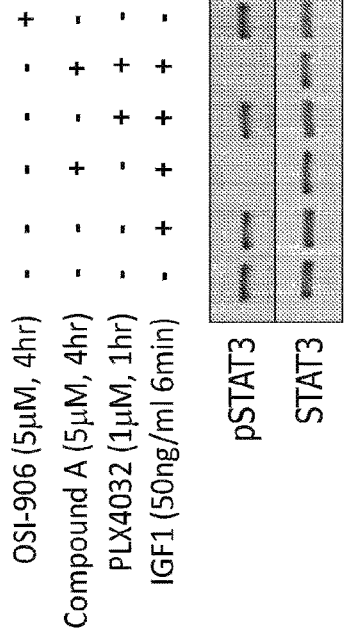
Figure 8B
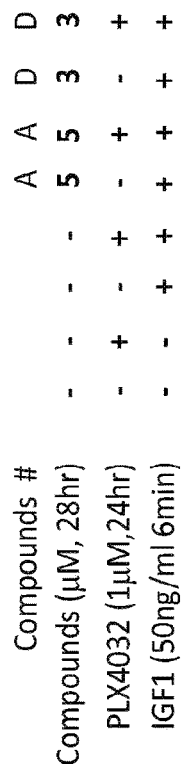
Figure 8C
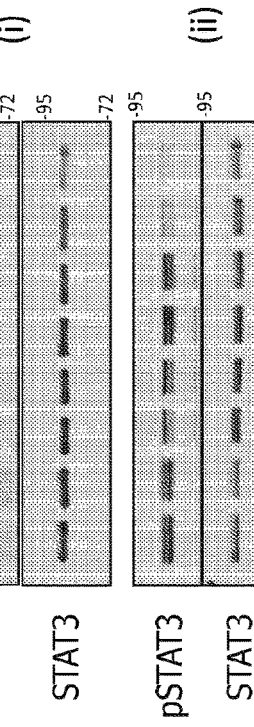

COMBINATIONS OF IRS/STAT3 DUAL MODULATORS AND ANTI-CANCER AGENTS FOR TREATING CANCER

CROSS REFERENCE TO RELATED APPLICATION(S)

This application is a Continuation of U.S. application Ser. No. 15/548,915 filed on Aug. 4, 2017, which a 35 U.S.C. 371 National Phase Entry Application from PCT/IL2016/050134, filed Feb. 4, 2016, which claims priority to U.S. Provisional Application No. 62/136,530, filed Mar. 22, 2015 and U.S. Provisional Application No. 62/112,257, filed Feb. 5, 2015. The entirety of the disclosure of the above-referenced applications are incorporated herein by reference.

FIELD OF THE INVENTION

The present invention relates to the treatment of cancer using combination therapy comprising a dual modulator of Insulin Receptor Substrate (IRS) and signal transducer and activator of transcription 3 (Stat3), in combination with (i) a modulator of a protein kinase (PK) selected from an Epidermal Growth Factor inhibitor (EGFR inhibitor) and EGFR antibody; (ii) an inhibitor of mammalian target of rapamycin (mTOR); (iii) a mitogen-activated protein kinase (MEK) inhibitor; (iv) a mutated B-Raf inhibitor; (v) a chemotherapeutic agent like Gemcitabine, 5-FU, Irinotecan and Oxaliplatin; and (vi) certain combinations thereof. The combination can be used to treat a tumor that has developed resistance to an EGFR inhibitor, EGFR antibody, mTOR inhibitor, MEK inhibitor, mutated B-Raf inhibitor, chemotherapeutic agents, and certain combinations thereof, or to prevent acquired resistance of a tumor to any of said inhibitors or agents, or to prevent tumor recurrence following cease of treatment with any of said inhibitors or agents or a combination thereof. The combination provides a therapeutic effect which is at least additive, and is preferably synergistic. The present invention further relates to the treatment of cancer using combination therapy comprising a dual modulator of IRS and Stat3, in combination with an immunotherapy agent. The combination can be used to sensitize a tumor to immunotherapy.

BACKGROUND OF THE INVENTION

Tyrphostins are a family of protein tyrosine kinase inhibitors, designed to mimic the tyrosine substrate, the ATP and can inhibit allosterically the enzyme (Levitzki et al., *Science* (1995), 267:1782-88; Levitzki et al., *Biochem. Pharm.* (1990), 40:913-920; Levitzki et al., *FASEB J.* (1992), 6:3275-3282; U.S. Pat. Nos. 5,217,999 and 5,773,476, Posner et al., *Mol. Pharmacol.* (1994), 45:673-683). The pharmacophores of these tyrphostins, and in particular tyrphostins of the benzylidene malonitril type, are the hydrophilic catechol ring and the more lipophilic substituted cyano-vinyl radical. Kinetic studies have shown that some tyrphostin compounds are pure competitive inhibitors vis-à-vis tyrosine substrates whereas for the ATP binding site they act as non-competitive inhibitors (Yaish et al., *Science* (1988), 242:933-935; Gazit et al., *J. Med. Chem.* (1989), 32:2344-2352). Nonetheless, many tyrphostins have shown competitive inhibition against both the substrate and ATP binding site or mixed competitive (Posner et al., *Mol. Pharmacol.* (1994), 45:673-683).

In a related group of tyrphostins, the hydrophilic catechol ring was exchanged by lipophilic dichloro- or dimethoxy-phenyl groups, to yield EGFR kinase inhibitors, effective in the low micromolar range (Yoneda et al., *Cancer Res.* (1991), 51: 4430-4435). These tyrphostins were further administered to tumor-bearing nude mice together with anti-EGFR monoclonal antibodies at a suboptimal dose to afford markedly enhanced inhibition of tumor growth.

WO 2008/068751 to some of the inventors of the present invention, discloses compounds having increased inhibitory properties of insulin-like growth factor 1 receptor (IGF1R), platelet derived growth factor receptor (PDGFR), epidermal growth factor receptor (EGFR), and IGF1R-related insulin receptor (IR) activation and signaling.

WO 2009/147682 to some of the inventors of the present invention discloses compounds acting as protein kinase (PK) and receptor kinase (RK) signaling modulators. Further disclosed in WO 2009/147682 are methods of preparation of the such compounds, pharmaceutical compositions including such compounds, and methods of using these compounds and compositions, especially as chemotherapeutic agents for preventions and treatments of PK and RK related disorders such as metabolic, inflammatory, fibrotic, and cell proliferative disorders, in particular cancer.

WO 2012/117396 to some of the inventors of the present invention describes combinations of the compounds of WO 2008/068751 or WO 2009/147682 with anti-cancer agents for the treatment of cancer.

Cancers treated with conventional radio- or chemotherapy or other anti-cancer agents frequently develop resistance to these treatments, ultimately leading to recurrent disease that often has a more aggressive phenotype than that observed at the time of the original diagnosis (Li et al., *J. Med. Chem.* (2009), 52(16): 4981-5004).

In accordance with principles for selecting agents for use in combination chemotherapy regimens, drugs with different mechanisms of action and with additive or synergistic cytotoxic effects on the tumor can be combined (Pazdur et al., *Chapter 3: Principles of Oncologic Pharmacotherapy* (2005), 9$^{th}$ Edition: 23-42). Multi-agent therapy has three important theoretical advantages over single-agent therapy. First, it can maximize cell death while minimizing host toxicities by using agents with non-overlapping dose-limiting toxicities. Second, it may increase the range of drug activity against tumor cells with endogenous resistance to specific types of therapy. Finally, it may also prevent or slow the development of newly resistant tumor cells. Virtually, almost all curative chemotherapy regimens for cancer employ multi-agent drug combinations (Frei and Eder, *Cancer medicine* (2003), 11:817-837).

A family of relatively new anti-cancer agents are inhibitors (e.g. antibodies and small molecules) of specific kinases or other signaling enzymes involved in the mitogenic, antiapoptotic, angiogenic or metastatic pathways in the cancerous cells. Examples of approved drugs included in this family are the EGFR and/or HER2 blockers (e.g. the small molecules gefitinib, erlotinib, lapatinib or antibodies like trastuzumab (Herceptin®) and cetuximab (Erbitux®)), B-Raf inhibitors (e.g. PLX-4032, sorafenib), BCR-ABL and/or Src family kinase inhibitors (e.g. imatinib, dasatinib, nilotinib), VEGFR/PDGFR and/or multi kinase inhibitors (e.g. bevacizumab (Avastin®), sorafenib, sunitinib, and pazopanib), and proteasome inhibitors (e.g. bortezomib (Velcade®)) etc. Several EGFR inhibitors were approved by the FDA like Tarceva (Erlotinib) in 2004, Iressa (Gefitinib) in 2003, and Lapatinib in 2010, as well as antibodies against EGFR.

Another family of anti-cancer agents are inhibitors of the mammalian target of rapamycin (mTOR). mTOR (also called FRAP (FKBP-rapamycin associated protein), RAFT (rapamycin and FKBP target), RAPT1, or SEP) is a serine/threonine kinase, which belongs to phosphatidylinositol-3 kinase (PI3K) related kinases (PIKKs) family mTOR functions as a central controller of growth, proliferation, metabolism and angiogenesis, but its signaling is deregulated in various human diseases especially certain cancers like renal cell carcinoma and breast cancer. In cancer, mTOR is frequently hyperactivated which promotes cancer development and progression. Recent development has made cancer treatment move on from conventional cytotoxic drugs to agents that target specific proteins like mTOR called mTOR inhibitors. A common mTOR inhibitor, rapamycin (Sirolimus), is a bacterial product that inhibits mTOR by associating with its intracellular receptor. Two mTOR inhibitors, Temsirolimus (CCI-779) and Everolimus (Afinitor, RAD-001) which are derivatives of rapamycin, are approved for the treatment of patients with advanced renal cell carcinoma (RCC) and mantle cell lymphoma. Other examples of mTOR inhibitors include Ridaforolimus (Deforolimus, AP23573), and NVP-BEZ235 which is a dual inhibitor of PI3K and mTOR.

The first generation of mTOR inhibitors like rapamycin, show certain limitations by blocking only C1 isoform, inducing feedback activation of AKT and showing resistance to the second isoform mTORC2. A panel of second generation agents that can inhibit both mTORC1 and mTORC2 by targeting kinase domains with high degree of selectivity are being developed. Examples of second generation mTOR inhibitors include OSI-027 (OSI Pharmaceuticals), XL765 (Exelixis), INK128, MLN0128, AZD2014, DS-3078a and Palomid529.

In the last few decades immunotherapy has become an important part of treating some types of cancer. The goal of cancer immunotherapy is to enable the patient's immune system to specifically recognize and kill cancer cells. Signal transducer and activator of transcription 3 (Stat3) is often activated in cancer and directly involved in the implementation and maintenance of the cancer immunosuppressive microenvironment and plays a central role in tumor immune evasion.

There is an unmet need for combinations that are useful for treating cancer, preferably providing at least additive therapeutic effects. Combinations of drugs from different categories are useful to prevent or overcome emergence of drug resistant tumors.

SUMMARY OF THE INVENTION

The present invention relates to compositions and methods for treating cancer, by administering a combination comprising at least one compound which is a dual modulator of Insulin Receptor Substrate (IRS) and signal transducer and activator of transcription 3 (Stat3), e.g., a compound of formula (III) or (IV), or any of the compounds covered by these formulae, in combination with (i) a modulator of a protein kinase (PK) selected from an Epidermal Growth Factor inhibitor (EGFR inhibitor) and EGFR antibody; (ii) an inhibitor of mammalian target of rapamycin (mTOR); (iii) a mitogen-activated protein kinase (MEK) inhibitor; (iv) a mutated B-Raf inhibitor; (v) a chemotherapeutic agent like Gemcitabine, 5-FU, Irinotecan and Oxaliplatin; and (vi) certain combinations thereof. The present invention further relates to the treatment of cancer using combination therapy comprising a dual modulator of IRS and Stat3, e.g., a compound of formula (III) or (IV), or any of the compounds covered by these formulae, in combination with an immunotherapy agent.

The compounds described herein are modulators of Insulin Receptor Substrate 1 (IRS1) and/or Insulin Receptor Substrate 2 (IRS2) signaling. Accordingly, these compounds are referred to herein as "modulators of IRS". In some embodiments, the compounds are inhibitors of IRS1 and/or IRS2. In further embodiments, the compounds of the invention are inhibitors of insulin-like growth factor 1 receptor (IGF-1R). As such, these compounds are useful in inhibiting, treating or preventing IGF-1R and/or IRS1 and/or IRS2 signaling related disorders, for example cancer. In some embodiments, the compounds trigger any one or more of the following, in any order: (i) dissociation of IRS1 and/or IRS2 from the cell membrane; (ii) serine phosphorylation of the IGF-1R direct substrates IRS1 and/or IRS2; and/or (iii) degradation of IRS1 and/or IRS2, thus providing long-lasting effects which enhance the inhibitory activity of these compounds. In other embodiments, the compounds are also inhibitors of IGF1R-related insulin receptor (IR), or proteins affected by or mediated by these PTKs or that are part of the PTK-mediated signal transduction pathway.

IRS are negatively regulated by EGFR downstream elements as well as by mTOR/S6K. Therefore, treating patients with drugs that inhibit these targets may result, as a side effect, in upregulating IRS and activating a central survival pathway to AKT. According to the principles of the present invention, this feedback mechanism leading to drug resistance may be overwhelmed by combining IRS destructor to the treatment, as demonstrated herein.

The compounds described herein are also modulators of signal transducer and activator of transcription 3 (Stat3). Accordingly, these compounds are also referred to herein as "modulators of Stat3". In some embodiments, the compounds lead to the inhibition of Stat3 phosphorylation in cancer cells. Increased levels of Stat3 phosphorylation are detected in various cancers and drug-resistant cancers, leading to enhanced cancer survival. Moreover, treatment of cancers with PK inhibitor drugs surprisingly leads to the induction of Stat3 phosphorylation, as demonstrated herein. Without wishing to be bound by any particular theory or mechanism of action, it is contemplated that inhibiting Stat3 activity with the compounds of the present invention may synergize with such PK inhibitor drugs, which as a side effect upregulate Stat3, may prevent acquired resistance to such drugs, and may be effective for drug-resistant cancers.

Due to their dual effect on IRS and Stat3, the compounds are further described herein as "IRS/Stat3 dual modulators".

Thus, in one embodiment, the present invention relates to a method of treating a tumor that has developed resistance to an Epidermal Growth Factor Receptor (EGFR) inhibitor and/or EGFR antibody, the method comprising the step of contacting the tumor with an EGFR inhibitor and/or EGFR antibody in combination with a compound represented by the structure of formula (III) or (IV).

In another embodiment, the present invention relates to a method of preventing acquired resistance of a tumor to an Epidermal Growth Factor Receptor (EGFR) inhibitor and/or EGFR antibody, the method comprising the step of contacting the tumor with an EGFR inhibitor and/or EGFR antibody in combination with a compound represented by the structure of formula (III) or (IV).

In another embodiment, the present invention relates to a method of preventing or delaying tumor recurrence following cease of treatment with a EGFR inhibitor and/or EGFR antibody, the method comprising the step of contacting the tumor with an EGFR inhibitor and/or EGFR antibody in combination with a compound represented by the structure of formula (III) or (IV).

In another embodiment, the present invention relates to a pharmaceutical combination comprising a compound represented by the structure of formula (III) or (IV), in combination with an Epidermal Growth Factor (EGFR) inhibitor, and/or EGFR antibody.

In another embodiment, the present invention relates to pharmaceutical combination comprising a compound represented by the structure of formula (III), in combination with an Epidermal Growth Factor (EGFR) inhibitor and/or EGFR antibody, wherein the EGFR inhibitor is selected from the group consisting of erlotinib, gefitinib, lapatinib, vandetanib, neratinib, icotinib, afatinib, dacomitinib, poziotinib, AZD9291, CO-1686, HM61713 and AP26113, and wherein the EGFR antibody is selected from the group consisting of trastuzumab, necitumumab, cetuximab and panitumumab, preferably wherein the EGFR inhibitor is erlotinib or afatinib, and/or wherein the EGFR antibody is cetuximab.

In other embodiments, the present invention relates to pharmaceutical combination comprising a compound represented by the structure of formula (IV), in combination with an Epidermal Growth Factor (EGFR) inhibitor and/or EGFR antibody.

In other embodiments, the present invention further relates to the pharmaceutical combinations as described above for use in treating a tumor that is resistant to an EGFR inhibitor and/or EGFR antibody, or for preventing acquired resistance to an EGFR inhibitor and/or EGFR antibody, or for preventing or delaying tumor recurrence following cease of treatment with a EGFR inhibitor and/or EGFR antibody.

In other embodiments, the present invention further relates to the use of the combinations described above for the preparation of a medicament for the treatment of a tumor that is resistant to an EGFR inhibitor and/or EGFR antibody, or for preventing acquired resistance to an EGFR inhibitor and/or EGFR antibody, or for preventing or delaying tumor recurrence following cease of treatment with a EGFR inhibitor and/or EGFR antibody.

In one embodiment, the compound is represented by the structure of formula (III). In another embodiment, the compound is represented by the structure of formula (IV). Each possibility represents a separate embodiment of the present invention.

In some embodiments, the tumor is present in a cancer patient having tumors with acquired resistance to EGFR inhibitor and/or EGFR antibody treatment. In other embodiments, the tumor is present in a cancer patient who is receiving treatment with an EGFR inhibitor and/or EGFR antibody or is a candidate for receiving such treatment. In other embodiments, the treatment results in attenuation or regression in the growth of the resistant tumors.

In some embodiments, the EGFR inhibitor is selected from the group consisting of erlotinib, gefitinib, lapatinib, vandetanib, neratinib, icotinib, afatinib, dacomitinib, poziotinib, AZD9291, CO-1686, HM61713 and AP26113. In one currently preferred embodiment, the EGFR inhibitor is erlotinib. In another currently preferred embodiment, the EGFR inhibitor is afatinib. Each possibility represents a separate embodiment of the present invention.

In some embodiments, the EGFR antibody is selected from the group consisting of trastuzumab, necitumumab, cetuximab and panitumumab. In one currently preferred embodiment, the EGFR antibody is cetuximab.

In some embodiments, the compound is a compound of formula (III), represented by the structure of formula D in combination with erlotinib or afatinib.

In other embodiments, the compound is a compound of formula (III), represented by the structure of formula D, in combination with cetuximab.

In other embodiments, the compound is a compound of formula (III), represented by the structure of formula D, in combination with afatinib and cetuximab.

In some embodiments, the combination treatment includes a compound of formula (III) or (IV), and either an EGFR antibody, or EGFR inhibitor. In other embodiments, the combination treatment includes a compound of formula (III) or (IV), and both an EGFR antibody and an EGFR inhibitor. In some currently preferred embodiments, the EGFR inhibitor is erlotinib or afatinib, and the EGFR antibody is cetuximab.

In one specific embodiment, the present invention relates to a pharmaceutical combination comprising a compound represented by the structure of formula D in combination with erlotinib. In one specific embodiment, the present invention relates to a pharmaceutical combination comprising a compound represented by the structure of formula D in combination with afatinib. In another specific embodiment, the present invention relates to a pharmaceutical combination comprising a compound represented by the structure of formula D in combination with cetuximab. In another specific embodiment, the present invention relates to a pharmaceutical combination comprising a compound represented by the structure of formula D in combination with afatinib and cetuximab.

In other aspects, it has now unexpectedly been found that a combination of a dual modulator of Insulin Receptor Substrate (IRS) and signal transducer and activator of transcription 3 (Stat3), as described herein, and an inhibitor of mammalian target of rapamycin (mTOR), provides a therapeutic effect that is at least additive, and is preferably synergistic as compared with the treatment effect of each agent alone. Furthermore, the combination can be used to treat a tumor that has developed resistance to an mTOR inhibitor, and/or to prevent acquired resistance of a tumor to the mTOR inhibitor and/or to prevent or delay tumor recurrence following cease of treatment with an inhibitor of mammalian target of rapamycin (mTOR).

Accordingly, in one embodiment, the present invention relates to a pharmaceutical combination comprising a compound represented by the structure of formula (III) or (IV), and at least one inhibitor of mammalian target of rapamycin (mTOR), wherein the compound and the at least one mTOR inhibitor together provide a synergistic therapeutic anticancer effect.

In other embodiments, the present invention relates to a method of treating cancer, comprising the step of administering to the subject in need thereof a therapeutically effective amount of a pharmaceutical combination comprising a compound represented by the structure of formula (III) or (IV), and at least one inhibitor of mammalian target of rapamycin (mTOR), wherein the compound and the at least one mTOR inhibitor together provide a synergistic therapeutic effect.

In other embodiments, the present invention relates to a method of treating a tumor that has developed resistance to an inhibitor of mammalian target of rapamycin (mTOR), the method comprising the step of contacting the tumor with an mTOR inhibitor in combination with a compound represented by the structure of formula (III) or (IV).

In other embodiments, the present invention relates to a method of preventing acquired resistance of a tumor to an inhibitor of mammalian target of rapamycin (mTOR), the method comprising the step of contacting the tumor with an mTOR inhibitor in combination with a compound represented by the structure of formula (III) or (IV).

In other embodiments, the present invention relates to a method of preventing or delaying tumor recurrence following cease of treatment with an inhibitor of mammalian target of rapamycin (mTOR), the method comprising the step of contacting the tumor with an mTOR inhibitor in combination with a compound represented by the structure of formula (III) or (IV).

In other embodiments, the present invention further relates to the pharmaceutical combination as described above for use in treating a tumor that is resistant to an mTOR inhibitor, or for preventing acquired resistance to an mTOR inhibitor, or for preventing or delaying tumor recurrence following cease of treatment with an inhibitor of mTOR.

In other embodiments, the present invention further relates to the use of the combination described above for the preparation of a medicament for the treatment of a tumor that is resistant to an mTOR inhibitor, or for preventing acquired resistance to an mTOR inhibitor, or for preventing or delaying tumor recurrence following cease of treatment with an inhibitor of mTOR.

In one embodiment, the compound is represented by the structure of formula (III). In another embodiment, the compound is represented by the structure of formula (IV). Each possibility represents a separate embodiment of the present invention.

In some embodiment, the tumor is present in a cancer patient having tumors with acquired resistance to mTOR inhibitor treatment. In other embodiments, the tumor is present in a cancer patient who is receiving treatment with an mTOR inhibitor or is a candidate for receiving such treatment. In other embodiments, the treatment results in attenuation or regression in the growth of the resistant tumors.

Any mTOR inhibitor known to a person of skill in the art may be used in the combinations of the present invention. In some embodiments, the mTOR inhibitor is selected from the group consisting of rapamycin (Sirolimus), Ridaforolimus (Deforolimus, AP23573), NVP-BEZ235, Everolimus (Afinitor, RAD-001), Temsirolimus (CCI-779), OSI-027, XL765, INK128, MLN0128, AZD2014, DS-3078a and Palomid529. In a currently preferred embodiment, the mTOR inhibitor is Everolimus.

In one specific embodiment, the compound is represented by the structure of formula D and the mTOR inhibitor is Everolimus (Afinitor).

In some embodiments, the subject or cancer patient is a human.

In other aspects, it has unexpectedly been found that dual modulators of IRS and Stat3 can be used to sensitize a tumor to immunotherapy. It is known that Stat3 is often activated in cancer and is directly involved in the implementation and maintenance of the cancer immunosuppressive microenvironment and plays a central role in tumor immune evasion. Without wishing to be bound by any particular theory or mechanism of action, it is contemplated that inhibition of Stat3 phosphorylation with the compounds of the present invention un-masks the tumor from the local immune system and sensitizes them to immunotherapy e.g. antibodies against PDLs, PD1, CTLA4 or any other immunotherapy agents.

Thus, in one embodiment, the present invention relates to a method of sensitizing a tumor to immunotherapy, the method comprising the step of contacting the tumor with a compound represented by the structure of formula (III) or (IV) in combination with an immunotherapy agent.

In another embodiment, the present invention further relates to a pharmaceutical combination comprising a compound represented by the structure of formula (III) or (IV), in combination with an immunotherapy agent.

In other embodiments, the present invention further relates to a combination comprising a compound of formula (III) or (IV) with an immunotherapy agent, for use in sensitizing a tumor to immunotherapy.

In other embodiments, the present invention further relates to the use of a combination comprising a compound of formula (III) or (IV) with an immunotherapy agent, for the preparation of a medicament for the treatment of a tumor by sensitizing the tumor to immunotherapy.

In one embodiment, the compound is represented by the structure of formula (III). In another embodiment, the compound is represented by the structure of formula (IV). Each possibility represents a separate embodiment of the present invention.

In some embodiments, the immunotherapy agent used in combination with the compound described above is an antibody against a target selected from the group consisting of PDL, PD1, CTLA4, CD20, CD30, CD33, CD52, VEGF, CD30, EGFR and ErbB2. In some embodiments, the antibody is selected from the group consisting of Alemtuzumab, Bevacizumab, Brentuximab vedotin, Cetuximab, Gemtuzumab ozogamicin, Ibritumomab tiuxetan, Ipilimumab, Ofatumumab, Panitumumab, Rituximab, Tositumomab and Tratuzumab. Each possibility represents a separate embodiment of the present invention.

In some embodiments, the tumor is present in a cancer patient who is receiving immunotherapy or a candidate for receiving immunotherapy.

In other aspects, it has now unexpectedly been found that a combination of a dual modulator of Insulin Receptor Substrate (IRS) and signal transducer and activator of transcription 3 (Stat3), as described herein, and a mitogen-activated protein kinase (MEK) inhibitor and/or a mutated B-Raf inhibitor, provides a therapeutic effect that is at least additive, and is preferably synergistic as compared with the treatment effect of each agent alone. Furthermore, the combination can be used to treat a tumor that has developed resistance to a MEK inhibitor and/or mutated B-Raf inhibitor, and/or to prevent acquired resistance of a tumor to a MEK inhibitor and/or mutated B-Raf inhibitor and/or to prevent or delay tumor recurrence following cease of treatment with a MEK inhibitor and/or mutated B-Raf inhibitor.

Thus, in some embodiments, the present invention relates to a method of treating a tumor that has developed resistance to a mitogen-activated protein kinase (MEK) inhibitor and/or a mutated B-Raf inhibitor, the method comprising the step of contacting the tumor with a MEK inhibitor and/or mutated B-Raf inhibitor, in combination with a compound represented by the structure of formula (III) or (IV).

In other embodiments, the present invention relates to method of preventing acquired resistance of a tumor to a MEK inhibitor and/or mutated B-Raf inhibitor, the method comprising the step of contacting the tumor with a MEK inhibitor and/or mutated B-Raf inhibitor, in combination with a compound represented by the structure of formula (III) or (IV).

In other embodiments, the present invention relates to a method of preventing or delaying tumor recurrence following cease of treatment with a MEK inhibitor and/or a mutated B-Raf inhibitor, the method comprising the step of contacting the tumor with a MEK inhibitor and/or mutated B-Raf inhibitor, in combination with a compound represented by the structure of formula (III) or (IV).

In other embodiments, the present invention relates to a pharmaceutical combination comprising a compound represented by the structure of formula (III), in combination with a mitogen-activated protein kinase (MEK) inhibitor, and optionally a mutated B-Raf inhibitor.

In some embodiments, the combination comprises a compound of formula (III), a MEK inhibitor and a mutated B-Raf inhibitor preferably, wherein the MEK inhibitor is Trametinib, and the mutated B-Raf inhibitor is Vemurafenib.

In other embodiments, the present invention relates to a compound represented by the structure of formula (IV), in combination with a mitogen-activated protein kinase (MEK) inhibitor, and/or a mutated B-Raf inhibitor.

In some embodiments, the tumor is present in a cancer patient having tumors with acquired resistance to MEK inhibitor and/or mutated B-Raf inhibitor treatment. In other embodiments, the treatment results in attenuation or regression in the growth of the resistant tumors. In other embodiments, the tumor is present in a cancer patient who is receiving treatment with an MEK inhibitor and/or a mutated B-Raf inhibitor or is a candidate for receiving such treatment.

Any MEK inhibitor known to a person of skill in the art may be used in the combinations of the present invention. In some embodiments, the MEK inhibitor is selected from the group consisting of Trametinib (GSK1120212), Selumetinib, Binimetinib (MEK162), PD-325901, Cobimetinib, CI-1040 and PD035901, preferably, wherein the MEK inhibitor is Trametinib.

Any mutated B-Raf inhibitor known to a person of skill in the art may be used in the combinations of the present invention. In some embodiments, the mutated B-Raf inhibitor is selected from the group consisting of Vemurafenib (PLX-4032), PLX4720, Sorafenib (BAY43-9006), and Dabrafenib, preferably, wherein the mutated B-Raf inhibitor is Vemurafenib.

In one embodiment, the compound is represented by the structure of formula (III). In another embodiment, the compound is represented by the structure of formula (IV). Each possibility represents a separate embodiment of the present invention.

In some embodiments, the compound is represented by the structure of formula D and the MEK inhibitor is Trametinib.

In other embodiments, the compound is represented by the structure of formula D and the mutated B-Raf inhibitor is Vemurafenib.

In some embodiments, the combination treatment includes a compound of formula (III) or (IV), and either a MEK inhibitor or a mutated B-Raf inhibitor. In other embodiments, the combination treatment includes a compound of formula (III) or (IV), and both a MEK inhibitor and a mutated B-Raf inhibitor.

In some embodiments, the subject or cancer patient is a human.

In some embodiments, the present invention relates to a pharmaceutical combination comprising a compound represented by the structure of formula D in combination with Trametinib.

In other embodiments, the present invention relates to a pharmaceutical combination comprising a compound represented by the structure of formula D in combination with Trametinib and Vemurafenib.

In other embodiments, the present invention relates to the combinations described above, for use in treating a tumor that is resistant to a MEK inhibitor and/or a mutated B-Raf inhibitor, or for preventing acquired resistance to a MEK inhibitor and/or a mutated B-Raf inhibitor, or for preventing or delaying tumor recurrence following cease of treatment with a MEK inhibitor and/or a mutated B-Raf inhibitor.

In other embodiments, the present invention relates to the use of the combinations described above, for the preparation of a medicament for the treatment of a tumor that is resistant to a MEK inhibitor and/or a mutated B-Raf inhibitor, or for preventing acquired resistance to a MEK inhibitor and/or a mutated B-Raf inhibitor, or for preventing or delaying tumor recurrence following cease of treatment with a MEK inhibitor and/or a mutated B-Raf inhibitor.

In other aspects, it has now unexpectedly been found that a combination of a dual modulator of Insulin Receptor Substrate (IRS) and signal transducer and activator of transcription 3 (Stat3), as described herein, and a chemotherapeutic agent such as Gemcitabine, 5-FU, Irinotecan, Oxaliplatin and any combination thereof (e.g., the combination treatment FOLFIRI or FOLFOX), provides a therapeutic effect that is at least additive, and is preferably synergistic as compared with the treatment effect of each agent alone. Furthermore, the combination can be used to treat a tumor that has developed resistance to any of these chemotherapeutic agents or their combination and/or to prevent acquired resistance of a tumor to any of these chemotherapeutic agents or their combination, and/or to prevent or delay tumor recurrence following cease of treatment with any of these therapeutic agents or their combination.

FOLFIRI is a combination treatment for cancer containing Leucovorin (Folinic Acid), 5-FU and Irinotecan. FOLFOX is a combination treatment for cancer containing Leucovorin calcium (Folinic Acid), 5-FU and Oxaliplatin.

Thus, according to some embodiments, the present invention relates to a pharmaceutical combination comprising a compound represented by the structure of formula (III) or (IV) and at least one chemotherapeutic agent selected from Gemcitabine, 5-FU, Irinotecan, Oxaliplatin and any combination thereof, wherein the compound and the chemotherapeutic agent(s) together provide a synergistic therapeutic anti-cancer effect.

In some embodiments, the present invention relates to a method of treating cancer, comprising the step of administering to the subject in need thereof a therapeutically effective amount of a combination comprising a compound represented by the structure of formula (III) or (IV) and at least one chemotherapeutic agent selected from Gemcitabine, 5-FU, Irinotecan, Oxaliplatin and any combination thereof, wherein the compound and the chemotherapeutic agent(s) together provide a synergistic therapeutic anti-cancer effect.

In other embodiments, the present invention provides a method of treating a tumor that has developed resistance to at least one chemotherapeutic agent, e.g., Gemcitabine, 5-FU, Irinotecan, Oxaliplatin and any combination thereof, the method comprising the step of contacting the tumor with at least one of said chemotherapeutic agent(s) in combination with a compound represented by the structure of formula (III) or (IV).

In other embodiments, the present invention provides a method of preventing acquired resistance of a tumor to at least one chemotherapeutic agent, e.g., Gemcitabine, 5-FU, Irinotecan, Oxaliplatin and any combination thereof, the method comprising the step of contacting the tumor with at least one of said chemotherapeutic agent(s) in combination with a compound represented by the structure of formula (III) or (IV).

In other embodiments, the present invention provides a method of preventing or delaying tumor recurrence following cease of treatment with at least one chemotherapeutic agent, e.g., Gemcitabine, 5-FU, Irinotecan, Oxaliplatin and any combination thereof, the method comprising the step of contacting the tumor with at least one of said chemotherapeutic agent(s) in combination with a compound represented by the structure of formula (III) or (IV).

In some embodiments, the tumor is present in a cancer patient having tumors with acquired resistance to any one or more of said chemotherapeutic agent(s). In other embodiments, the treatment results in attenuation or regression in the growth of the resistant tumors. In other embodiments, the tumor is present in a cancer patient who is receiving treatment with said chemotherapeutic agent(s), or is a candidate for receiving such treatment.

In other embodiments, the present invention provides a pharmaceutical combination comprising a compound represented by the structure of formula (III) or (IV) and at least one chemotherapeutic agent selected from Gemcitabine, 5-FU, Irinotecan, Oxaliplatin and any combination thereof, for use in treating a tumor that is resistant to any one or more of said chemotherapeutic agent(s), or for preventing acquired resistance to said chemotherapeutic agent(s), or for delaying tumor recurrence following cease of treatment with any one or more of such chemotherapeutic agent(s).

In other embodiments, the present invention relates to the use of a pharmaceutical combination comprising a compound represented by the structure of formula (III) or (IV) and at least one chemotherapeutic agent selected from Gemcitabine, 5-FU, Irinotecan, Oxaliplatin and any combination thereof, for the preparation of a medicament for the treatment of a tumor that is resistant to said chemotherapeutic agent(s), or for preventing acquired resistance to said chemotherapeutic agent(s), or for of preventing or delaying tumor recurrence following cease of treatment with such chemotherapeutic agent(s).

As contemplated herein, the present invention provides several examples where tumors with activated K-RAS that did not respond to an anti-cancer drug, demonstrated impressive tumor regression when the anti-cancer agent was combined with compound D. For example, the combination of anti-cancer agents with compound D converted "Non-responding" tumors to "Responder" to the anti-cancer agent. In example 1 (FIG. 1) genomic analysis of the Erlotinib-treated group at the end point, meaning—the Erlotinib-resistant clones, revealed several alterations as compared to the control. Among these novel genomic variations was KRAS, known to generate resistance to EGFR inhibitors. Genomic alternations related to KRAS included amplification of KRAS and NF-1 loss, which results in the activation of K-Ras. In contrast to the Erlotinib-treated tumors, the tumors that were treated with both Erlotinib and compound D did not have the KRAS alterations. In these tumors (treated by both Erlotinib and compound D)- resistance to Erlotinib was not acquired and tumors did not progress while on treatment. In addition, treatment of the Erlotinib-resistant tumors with the compound D+ Erlotinib re-sensitized these tumors to Erlotinib and induced tumor regression. This suggests that compound D inclusion antagonized the resistance imposed by KRAS amplification and/or activation. In another example, the Gemcitabine-resistant pancreatic tumors (FIG. 13A,B), bearing mutated KRAS, were re-sensitized to the treatment with Gemcitabine by combining it with compound D. Furthermore, supporting data from the literature show that many drug-treated "oncogene-addicted" cancer cells engage a positive feedback loop leading to STAT5 activation, consequently promoting cell survival and limiting overall drug response. This was observed in cancer cells driven by diverse activated kinases, including EGFR, HER2, ALK, and MET, as well as mutant KRAS.

Accordingly, in some aspects, the present invention relates to a method of treating a tumor, comprising the step of contacting the tumor with combinations of a compound of formula (III) or (IV) with an anti-cancer drug, to which the tumors developed resistance due to mutations and/or amplification in KRAS. Any of the anti-cancer agents described herein (e.g., EGFR inhibitor/EGFR antibody/mTOR inhibitor/immunotherapy agent/MEK inhibitor/mutated B-Raf inhibitor/chemotherapeutic agent/combinations of the foregoing) can be used in in such methods, by treating tumors that have developed resistance to such agents due to mutations and/or amplification of KRAS.

The compound of formula (III) is represented by the structure

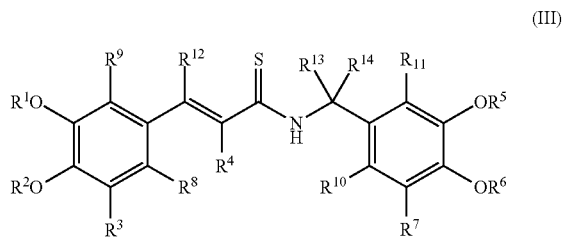

(III)

wherein
$R^1$, $R^2$, $R^5$ and $R^6$ are independently selected from H, $C_1$-$C_4$ alkyl, $(CH_2CH_2O)_nH$ wherein n is an integer of 1 to 20, acyl and a functional group that gives rise to hydroxyl upon hydrolysis;
$R^3$, $R^7$, $R^8$, $R^9$, $R^{10}$, $R^{11}$, $R^{12}$, $R^{13}$ and $R^{14}$ are independently selected from H, halogen, $C_1$-$C_4$ alkyl, $C_1$-$C_4$ haloalkyl, $CH_2SR^a$ wherein $R^a$ is selected from H, $C_1$-$C_4$ alkyl, aryl, heterocyclyl, heteroaryl, $C_1$-$C_4$ alkylaryl, $C_1$-$C_4$ alkylheterocyclyl and $C_1$-$C_4$ alkyl-hereroaryl, and $OR^{16}$ wherein $R^{16}$ is H, $C_1$-$C_4$ alkyl, $(CH_2CH_2O)_nH$, acyl or a functional group that gives rise to hydroxyl upon hydrolysis; and
$R^4$ is H or CN;
including salts, hydrates, solvates, polymorphs, optical isomers, geometrical isomers, enantiomers, diastereomers, and mixtures thereof.

In some embodiments, the compound of formula (III) is selected from the group consisting of compounds A, B, C, D, E, F, G, H, I and J:

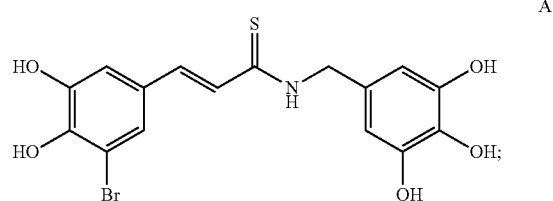

A

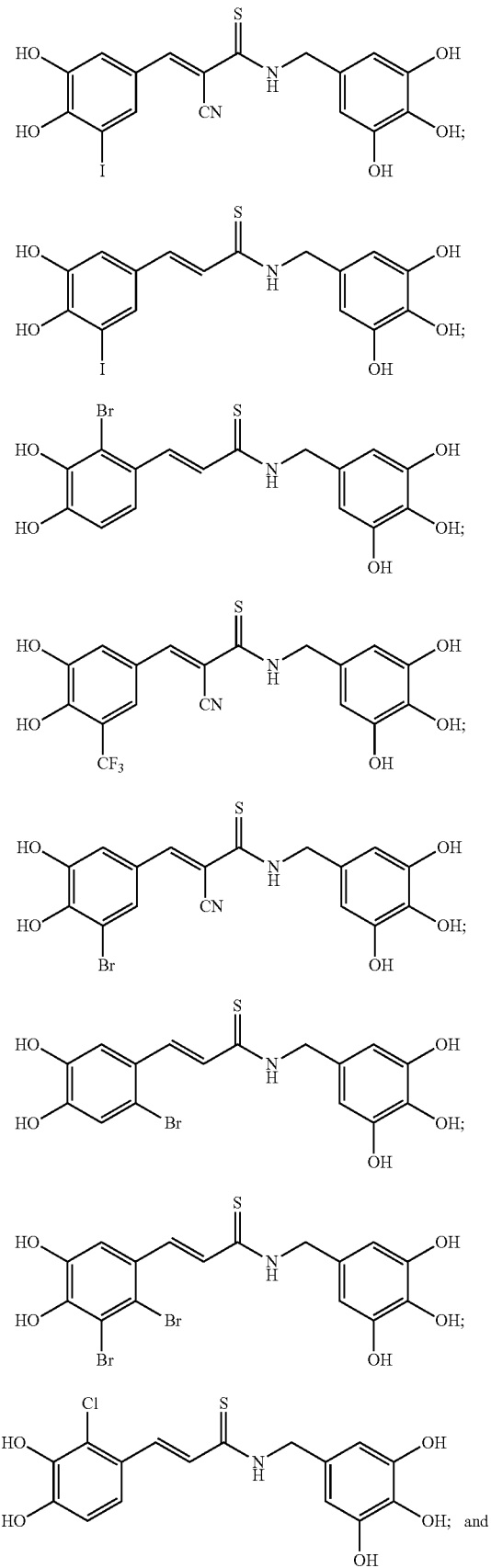

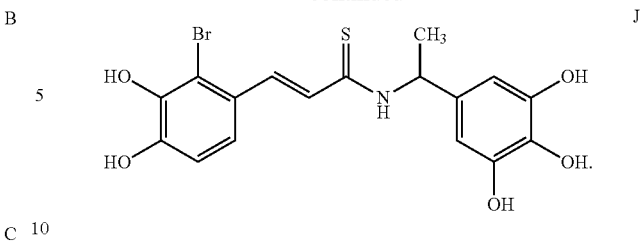

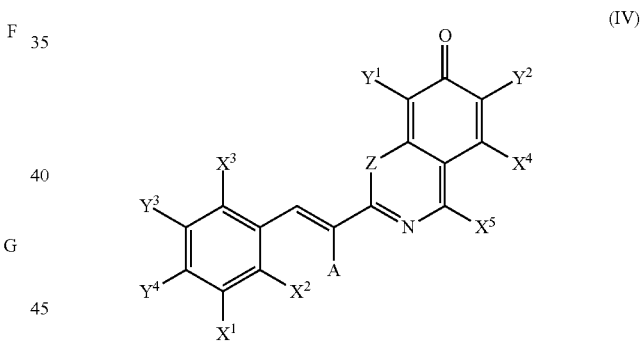

In one embodiment, the compound is a compound of formula A. In another embodiment, the compound is a compound of formula B. In another embodiment, the compound is a compound of formula C. In another embodiment, the compound is a compound of formula D. In another embodiment, the compound is a compound of formula E. In another embodiment, the compound is a compound of formula F. In another embodiment, the compound is a compound of formula G. In another embodiment, the compound is a compound of formula H. In another embodiment, the compound is a compound of formula I. In another embodiment, the compound is a compound of formula J. In one currently preferred embodiment, the compound is represented by the structure of formula D.

The compound of formula (IV) is represented by the structure (IV)

wherein

A is H or CN;

Z is S, SO or $SO_2$;

$X^1$, $X^2$, $X^3$, $X^4$, $X^5$, $Y^1$ and $Y^2$ are each independently selected from H, halogen, alkyl, haloalkyl and $OR^1$; and $Y^3$ and $Y^4$ are each $OR^1$, wherein each $R^1$ is independently H, $C_1$-$C_4$ alkyl, —$(CH_2CH_2O)_n$H wherein n is an integer of 1 to 20, acyl or a functional group that gives rise to hydroxyl upon hydrolysis, including salts, hydrates, solvates, polymorphs, optical isomers, geometrical isomers, enantiomers, diastereomers, and mixtures thereof.

In some embodiments, the compound of formula (IV) is represented by the structure of formula (IV-4)

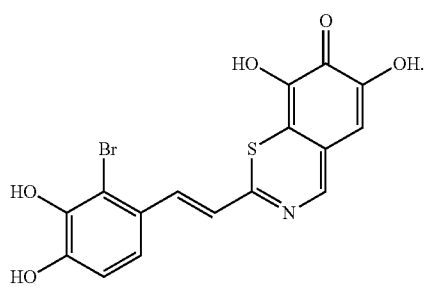

IV-4

It is further apparent to a person of skill in the art that any other compounds of formula (I) or (IV) described herein can be used for any of the combination treatments described by the present invention.

The combinations of the present invention are suitable for treating various types of cancers. In particular, the combinations of the present invention are active against head and neck (H&N) cancer, sarcoma, multiple myeloma, ovarian cancer, breast cancer, kidney cancer, stomach cancer, hematopoietic cancers, lymphoma, leukemia, including lymphoblastic leukemia, lung carcinoma, melanoma, glioblastoma, hepatocarcinoma, prostate cancer and colon cancer. Each possibility represents a separate embodiment of the present invention.

The term "combination" or "combined treatment" as used herein denotes any form of concurrent or parallel treatment with at least two distinct therapeutic agents. This term is intended to encompass both concomitant administration of the two treatment modalities, i.e., using substantially the same treatment schedule, as well as overlapping administration in sequential or alternating schedules of each treatment. Each possibility represents a separate embodiment of the present invention.

The combination therapy is particularly advantageous, since the dosage of each agent in a combination therapy can be reduced as compared to mono-therapy with each agent, while still achieving an overall anti-cancer effect. Accordingly, reducing the dosage of each agent may result in decreased side effects. The combination therapy may reduce the development of resistance to a specific anti-cancer treatment and/or lead to regression of the tumor after it has acquired resistance, as demonstrated herein.

The compound of formula (III) or (IV) and the EGFR inhibitor/EGFR antibody/mTOR inhibitor/immunotherapy agent/MEK inhibitor/mutated B-Raf inhibitor/chemotherapeutic agent/combinations of the foregoing can be administered simultaneously (in the same or in separate dosage forms), or they can be administered sequentially, in any order. The administration can also take place according to alternating dosing schedules, e.g., compound of formula (III) or (IV) followed by the additional agent(s), then an additional dose of the compound of formula (III) or (IV), followed by the same or yet another agent(s) and so forth. All administration schedules, including simultaneous, sequential and alternating, are contemplated by the present invention, wherein each possibility represents a separate embodiment of the present invention.

The pharmaceutical compositions of the present invention can be provided in any form known in the art, for example in a form suitable for oral administration (e.g., a solution, a suspension, a syrup, an emulsion, a dispersion, a tablet, a pill, a capsule, a pellet, granules and a powder), for parenteral administration (e.g., intravenous, intramuscular, intra-arterial, transdermal, subcutaneous or intra-peritoneal), for topical administration (e.g., an ointment, a gel, a cream), for administration by inhalation or for administration via suppository. Each possibility represents a separate embodiment of the present invention.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 5A. The Afinitor-treated group was divided to responders (open squares, group A, n=8) vs. non-responders (grey squares, group B, n=7). Afinitor treatment of group A initially induced tumor regression, but while on treatment all tumors developed resistance to Afinitor and aggressively progressed. Combined treatment of Afinitor and Compound D from day0 (treatment initiation) induced tumor regression and their average tumor volume remained low till the end of the experiment (○). FIG. 5B. Following resistance to Afinitor has been acquired, the mice of group A were divided into two groups, the first remained on Afinitor alone (□) and the second received combined treatment of Afinitor+Compound D starting on day 6 of treatment (●). While tumors significantly progressed under treatment with Afinitor alone (□), the combined treatment of Compound D and Afinitor induced tumor regression (●). The graph in FIG. 5B represents growth rates in %, while the 100% for each tumor was defined as its volume at day 6. FIG. 5C Combined treatment with Afinitor+Compound D of highly aggressive Uterine Adenosarcoma cancer with no available medical treatment delayed acquired resistance to Afinitor and achieved complete response in 40% of the group.

FIG. 7A. Highly increased levels of pStat3 in the BRAFi-resistant melanoma clone (R) as compared to the parental melanoma cells (P). Human metastatic melanoma 451-Lu cells (P) and the PLX4032-resistant clone, both possess mutated BRAF, were grown in a serum-free medium and immunoblotted with anti-pStat3 Ab followed by anti-Stat3 Ab. FIG. 7B. Highly increased levels of pStat3 in melanoma cells with mutated BRAF, derived from patients that acquired resistance to the BRAFi PLX4032 (R) compared to melanoma cells with mutated BRAF from naive patients that were not treated with PLX4032 (N). Cells from patients were grown in complete medium and immunoblotted as described above. FIGS. 7C-E. Treatment with PLX4032 of BRAF-mutated human melanoma cells surprisingly induces a dramatic increase in pStat3. Compounds A/D block the basal and the PLX4032-induced pStat3. Treatment of PLX4032-sensitive human melanoma A375 (C), 451-Lu (D) or Mel1617 (E) cells with 1 µM PLX4032 for 18-24 hr induces a dramatic increase in pStat3. Compounds A (FIG. 7C, D) or D (FIG. 7E) block both the basal and the PLX4032-induced pStat3. OSI-906, an ATP-competitive inhibitor of IGF1R, has no effect on pStat3.

FIGS. 8A-8D. Dual modulators of IRS/Stat3 efficiently inhibit pStat3 in BRAFi-resistant melanoma cells, which acquired resistance in culture or in patients. Their ability to inhibit pStat3 was exemplified in various cancer types. FIG. 8A-B. Compound A, as opposed to the IGF1R inhibitor OSI-906, potently inhibits pStat3 in BRAFi-resistant clones of melanoma, 451-BR (FIG. 8A) and Mel1617-BR (FIG. 8B). FIG. 8C. Compound A, and more potently compound D, inhibit pStat3 in melanoma cells from patients (i and ii) who acquired resistance to PLX4032 following treatment. FIG. 8D. Cells of various cancer types were treated with compound D for 4 hr in serum-free medium, and 20 hr in medium with or without 10% serum. Asterisks indicate 10 µM concentration for RPMI8226 and HepG2 cells.

FIG. 9A. Chemotaxis of PBMCs towards Compound A was examined 24 hrs later by Cell Titer Glo analysis of the lower plate. FIG. 9B. PBMC calibration curve of 10-10,000 cells/well.

DETAILED DESCRIPTION OF THE PRESENT INVENTION

Figure 1:
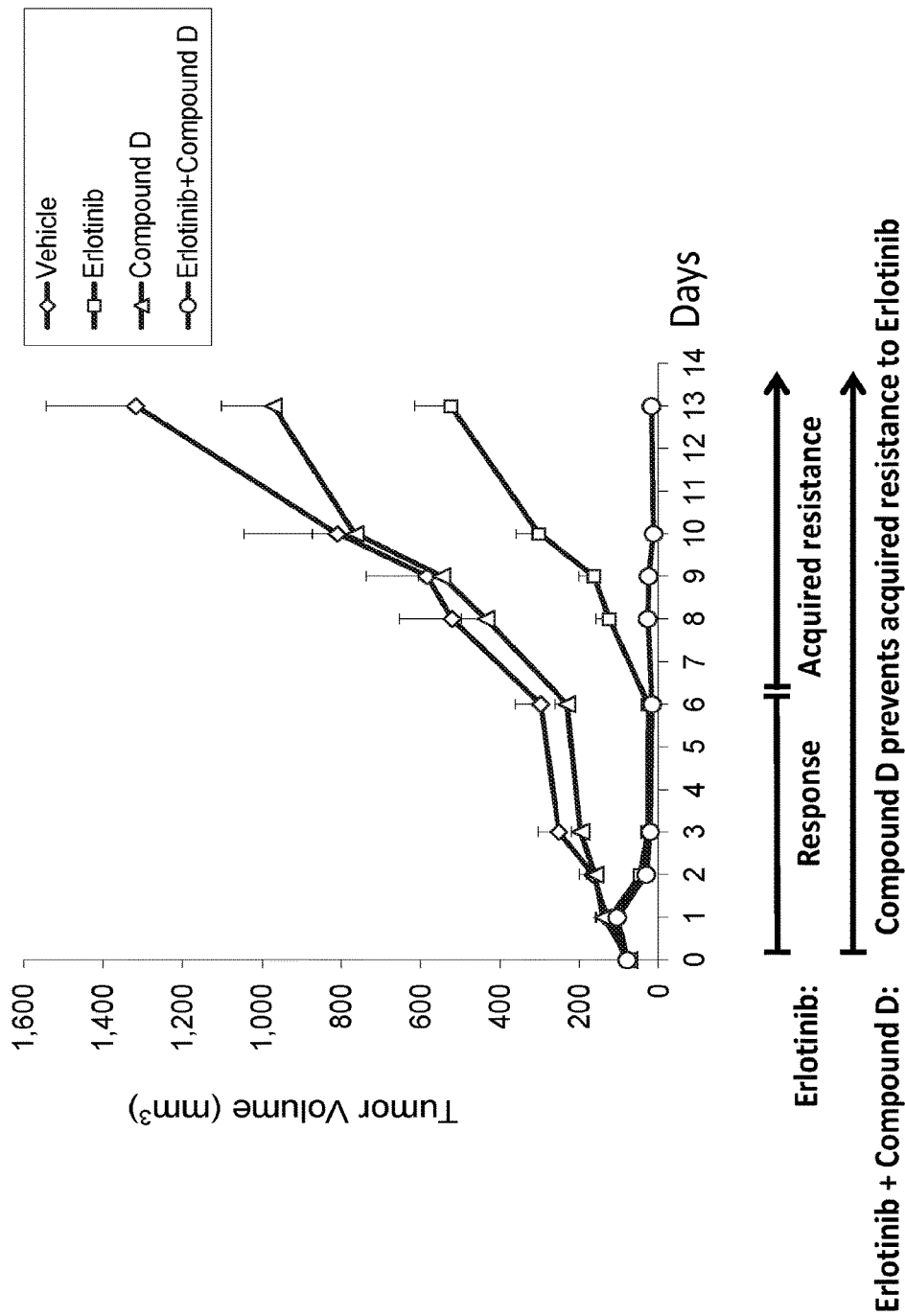
FIG. 1. Compound D prevents acquired resistance to Erlotinib in mice implanted with a tumor from a Head & Neck (H&N) cancer patient. Mice were treated with (a) vehicle (◇); (b) Erlotinib (□); (c) Compound D (Δ); or (d) Erlotinib+Compound D (○). Treatments were initiated when average tumor size was ~80 mm$^3$. Treatment with Erlotinib induced significant tumor regression, but while on treatment all Erlotinib-treated mice developed resistance to Erlotinib and their tumors aggressively regrew. Combined treatment of Erlotinib and Compound D induced tumor regression and none of them regrew while on treatment. P values (vs. Erlotinib)=0.0001.

The present invention relates to the treatment of cancer using combination therapy comprising a dual modulator of Insulin Receptor Substrate (IRS) and signal transducer and activator of transcription 3 (Stat3), in combination with (i) a modulator of a protein kinase (PK) selected from an Epidermal Growth Factor inhibitor (EGFR inhibitor) and EGFR antibody; (ii) an inhibitor of mammalian target of rapamycin (mTOR); (iii) a mitogen-activated protein kinase (MEK) inhibitor; (iv) a mutated B-Raf inhibitor; (v) a chemotherapeutic agent like Gemcitabine, 5-FU, Irinotecan and Oxaliplatin; and (vi) certain combinations thereof. The combination can be used to treat a tumor that has developed resistance to an EGFR inhibitor, EGFR antibody, mTOR inhibitor, MEK inhibitor, mutated B-Raf inhibitor, chemotherapeutic agents, and certain combinations thereof, or to prevent acquired resistance of a tumor to any of said inhibitors or agents, or to prevent tumor recurrence following cease of treatment with any of said inhibitors or agents or a combination thereof. The combination provides a therapeutic effect which is at least additive, and is preferably synergistic. The present invention further relates to the treatment of cancer using combination therapy comprising a dual modulator of IRS and Stat3, in combination with an immunotherapy agent. The combination can be used to sensitize a tumor to immunotherapy.

Insulin Receptor Substrate (IRS)/Signal Transducer and Activator of Transcription 3 (Stat3) Dual Modulators Any compound of the general structure of formula (I) can be used in the compositions of the present invention:

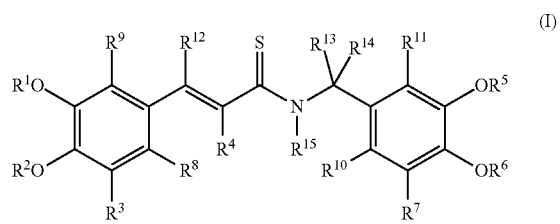

wherein
R$^1$, R$^2$, R$^5$ and R$^6$ are each independently selected from H, C$_1$-C$_4$ alkyl, C$_2$-C$_6$ alkenyl, C$_2$-C$_6$ alkynyl, C$_1$-C$_4$ alkyl-C$_2$-C$_6$ alkenyl, C$_1$-C$_4$ alkyl-C$_2$-C$_6$ alkynyl, (CH$_2$CH$_2$O)$_n$H, C$_3$-C$_7$ cycloalkyl, aryl, heterocyclyl, heteroaryl, (C$_1$-C$_4$)-alkylaryl, (C$_1$-C$_4$)-alkylheterocyclyl, (C$_1$-C$_4$)-alkylheteroaryl, haloalkyl, acyl and a functional group that gives rise to hydroxyl upon hydrolysis;
R$^3$, R$^4$, R$^7$, R$^8$, R$^9$, R$^{10}$, R$^{11}$, R$^{12}$, R$^{13}$ and R$^{14}$ are each independently selected from H, C$_1$-C$_4$ alkyl, C$_2$-C$_6$ alkenyl, C$_2$-C$_6$ alkynyl, C$_1$-C$_4$ alkyl-C$_2$-C$_6$ alkenyl, C$_1$-C$_4$ alkyl-C$_2$-C$_6$ alkynyl, C$_3$-C$_7$ cycloalkyl, aryl, heterocyclyl, heteroaryl, (C$_1$-C$_4$)-alkylaryl, (C$_1$-C$_4$)-alkylheterocyclyl, (C$_1$-C$_4$)-alkylheteroaryl, halogen, haloalkyl, NO$_2$, CN, N$_3$, SO$_2$R$^a$, COOR$^a$, CSNR$^a$R$^b$, CSOR$^a$, OR$^a$, CONR$^a$R$^b$, NR$^a$R$^b$, SR$^a$, and CH$_2$SR$^a$, wherein R$^a$ and R$^b$ are each independently H, C$_1$-C$_4$ alkyl, C$_2$-C$_6$ alkenyl, C$_2$-C$_6$ alkynyl, C$_1$-C$_4$ alkyl-C$_2$-C$_6$ alkenyl, C$_1$-C$_4$ alkyl-C$_2$-C$_6$ alkynyl, C$_3$-C$_7$ cycloalkyl, aryl, heterocyclyl, heteroaryl, (C$_1$-C$_4$)-alkylaryl, (C$_1$-C$_4$)-alkylheterocyclyl, (C$_1$-C$_4$)-alkylheteroaryl, haloalkyl, (CH$_2$CH$_2$O)$_n$H, acyl or a functional group that gives rise to hydroxyl upon hydrolysis; and
R$^{15}$ is H, C$_1$-C$_4$ alkyl, C$_2$-C$_6$ alkenyl, C$_2$-C$_6$ alkynyl, C$_1$-C$_4$ alkyl-C$_2$-C$_6$ alkenyl, C$_1$-C$_4$ alkyl-C$_2$-C$_6$ alkynyl, haloalkyl, or OR$^b$ wherein R$^b$ is independently H or C$_1$-C$_4$ alkyl;
including salts, hydrates, solvates, polymorphs, optical isomers, geometrical isomers, enantiomers, diastereomers, and mixtures thereof. Each possibility represents a separate embodiment of the invention.

In an exemplary embodiment, the compound is a compound represented by formula A:

[Structure A]

In another exemplary embodiment, the compound is a compound represented by formula B:

[Structure B]

In another exemplary embodiment, the compound is a compound represented by formula C:

[Structure C]

In another exemplary embodiment, the compound is a compound represented by formula D:

[Structure D]

In another exemplary embodiment, the compound is a compound represented by formula E:

[Structure E]

In another exemplary embodiment, the compound is a compound represented by formula F:

[Structure F]

In another exemplary embodiment, the compound is a compound represented by formula G:

[Structure G]

In another exemplary embodiment, the compound is a compound represented by formula H:

[Structure H]

In another exemplary embodiment, the compound is a compound represented by formula I:

[Structure I]

In another exemplary embodiment, the compound is a compound represented by formula J:

[Structure J]

In another embodiment, the compound is a compound of formula I wherein $R^1$, $R^2$, $R^4$, $R^5$, $R^6$, $R^{10}$, $R^{12}$, $R^{13}$, $R^{14}$ and $R^{15}$ are each H; $R^7$ is OH; and at least one of $R^3$, $R^8$, $R^9$ and $R^{11}$ is halogen.

In another embodiment, the compound is a compound of formula I wherein $R^1$, $R^2$, $R^4$, $R^5$, $R^6$, $R^8$, $R^{10}$, $R^{12}$, $R^{13}$, $R^{14}$ and $R^{15}$ are each H; $R^7$ is OH; and at least one of $R^3$, $R^9$ and $R^{11}$ is halogen.

In another embodiment, the compound is a compound of formula I wherein $R^1$, $R^2$, $R^5$ and $R^6$ are each H or a functional group that gives rise to hydroxyl upon hydrolysis.

In another embodiment, the compound is a compound of formula I wherein $R^7$ is H or $OR^a$ and $R^1$, $R^2$, $R^5$, $R^6$, and $R^a$ are each H or a functional group that gives rise to hydroxyl upon hydrolysis.

In another embodiment, the compound is a compound of formula I wherein $R^{13}$ and $R^{14}$ are each independently H, $C_1$-$C_4$ alkyl, $C_2$-$C_6$ alkenyl, $C_2$-$C_6$ alkynyl, $C_1$-$C_4$ alkyl-$C_2$-$C_6$ alkenyl or $C_1$-$C_4$ alkyl-$C_2$-$C_6$ alkynyl.

In another embodiment, the compound is a compound of formula I wherein at least one of $R^{13}$ and $R^{14}$ is H or $C_1$-$C_4$ alkyl.

In another embodiment, the compound is a compound of formula I wherein $R^3$, $R^4$, $R^7$, $R^8$, $R^9$, $R^{10}$, $R^{11}$, $R^{12}$, $R^{13}$, and $R^{14}$ are each independently H, halogen, haloalkyl, OH, $NO_2$, CN, or $CH_2SR^a$, wherein $R^a$ is as defined hereinabove.

In another embodiment, the compound is a compound of formula I wherein $R^4$ is H.

In another embodiment, the compound is a compound of formula I wherein $R^4$ is CN.

In another embodiment, the compound is a compound of formula I wherein $R^4$, $R^{11}$, $R^{12}$, $R^{13}$, $R^{14}$ and $R^{15}$ are each H.

In another embodiment, the compound is a compound of formula I wherein $R^{13}$, $R^{14}$ and $R^{15}$ are each H.

In another embodiment, the compound is a compound of formula I wherein $R^3$, $R^7$, $R^8$, $R^9$, $R^{10}$ and $R^{11}$ are each independently H, halogen, haloalkyl, $CH_2SR^a$ or OH; $R^4$, $R^{12}$, $R^{13}$ and $R^{14}$ are each independently H, $C_1$-$C_4$ alkyl, $C_2$-$C_6$ alkenyl, $C_2$-$C_6$ alkynyl, $C_1$-$C_4$ alkyl-$C_2$-$C_6$ alkenyl, $C_1$-$C_4$ alkyl-$C_2$-$C_6$ alkynyl, aryl, halogen, haloalkyl, $NO_2$, or CN; and $R^{15}$ is H.

In another embodiment, the compound is a compound of formula I wherein $R^3$, $R^7$, $R^8$, $R^9$, $R^{10}$ and $R^{11}$ are each independently H, halogen, haloalkyl, OH or $CH_2SR^a$; and $R^4$, $R^{12}$, $R^{13}$, $R^{14}$ and $R^{15}$ are each H, or a $C_1$-$C_4$ alkyl.

In another embodiment, the compound is a compound of formula I wherein $R^1$, $R^2$, $R^5$ and $R^6$ are each H or a functional group that gives rise to hydroxyl upon hydrolysis; $R^3$, $R^8$, and $R^9$ are each independently H, halogen, haloalkyl, or $CH_2SR^a$; $R^7$, $R^{10}$ and $R^{11}$ are each independently H, halogen, haloalkyl, OH or a functional group that gives rise to hydroxyl upon hydrolysis; and $R^4$, $R^{12}$, $R^{13}$, $R^{14}$ and $R^{15}$ are each H, or $C_1$-$C_4$ alkyl.

In another embodiment, the compound is a compound of formula I wherein the compound is represented by any one of the structures:

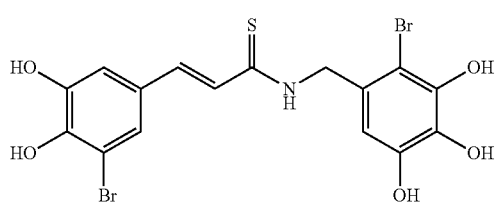

I-4

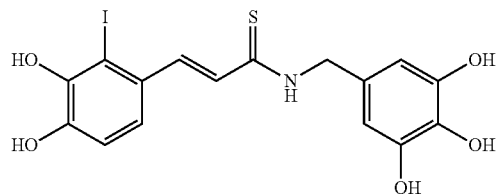

I-7

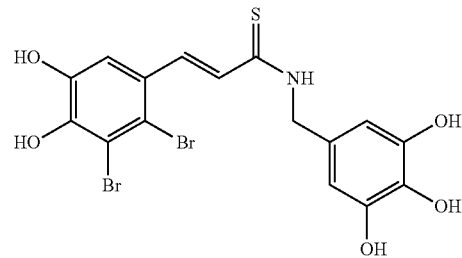

I-8b

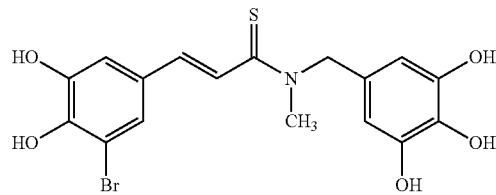

I-9a

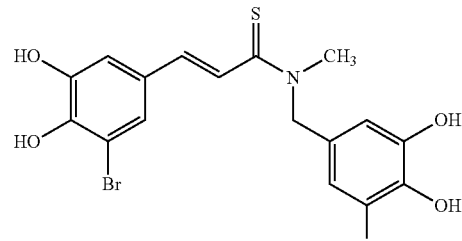

I-9b

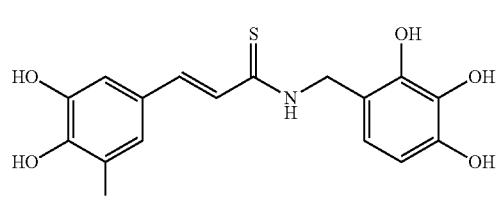

I-10

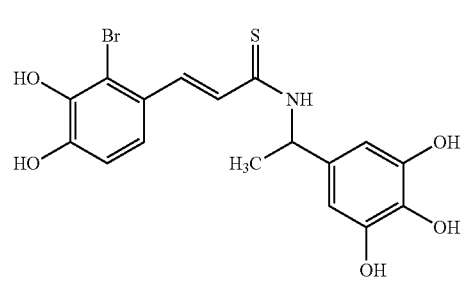

I-12b

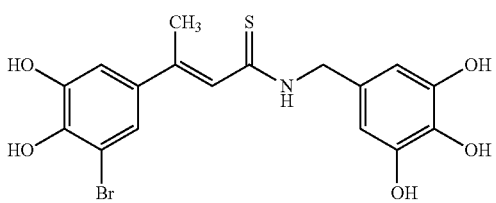

I-13a

-continued

I-13b

[Chemical structure]

I-14

[Chemical structure]

I-15

[Chemical structure]

I-16

[Chemical structure]

Each possibility represents a separate embodiment of the present invention.

In other embodiments, the compound is a compound represented by the structure of formula II:

(II)

[Chemical structure of formula II]

wherein $R^1$, $R^2$, $R^5$ and $R^6$ are independently selected from H, $C_1$-$C_4$ alkyl, acyl and a functional group that gives rise to hydroxyl upon hydrolysis;

$R^3$ and $R^7$ are independently selected from H, halogen, haloalkyl and $OR^8$ wherein $R^8$ is H, $C_1$-$C_4$ alkyl, acyl or a functional group that gives rise to hydroxyl upon hydrolysis; and $R^4$ is H or CN, including salts, hydrates, solvates, polymorphs, optical isomers, geometrical isomers, enantiomers, diastereomers, and mixtures thereof.

In other embodiments, the compound is a compound represented by the structure of formula II, wherein $R^1$, $R^2$, $R^5$ and $R^6$ are independently selected from H, $C_1$-$C_4$ alkyl, $(CH_2CH_2O)_nH$ wherein n is an integer of 1 to 20, acyl and a functional group that gives rise to hydroxyl upon hydrolysis;

$R^3$ and $R^7$ are independently selected from H, halogen, $C_1$-$C_4$ alkyl, haloalkyl and $OR^{16}$ wherein $R^{16}$ is H, $C_1$-$C_4$ alkyl, $(CH_2CH_2O)_nH$, acyl or a functional group that gives rise to hydroxyl upon hydrolysis; and $R^4$ is H or CN, including salts, hydrates, solvates, polymorphs, optical isomers, geometrical isomers, enantiomers, diastereomers, and mixtures thereof.

Each possibility represents a separate embodiment of the present invention.

In another embodiment, the compound is a compound of formula II wherein $R^4$ is CN.

In other embodiments, the compound is a compound of formula II wherein $R^1$, $R^2$, $R^5$ and $R^6$ are each hydrogen.

In other embodiments, the compound is a compound of formula II wherein $R^1$, $R^2$, $R^5$ and $R^6$ are each $CH_3$.

In other embodiments, the compound is a compound of formula II wherein $R^3$ and $R^7$ are each a hydrogen, halogen, halomethyl, OH or $OCH_3$.

In other embodiments, the compound is a compound of formula II wherein $R^1$, $R^2$, $R^5$ and $R^6$ are each H, $R^3$ is halogen and $R^7$ is OH.

In other embodiments, the compound is a compound of formula II wherein $R^1$, $R^2$, $R^5$ and $R^6$ are each H, and $R^3$ and $R^7$ are each halogen.

In other embodiments, the compound is a compound of formula II wherein $R^1$, $R^2$, $R^5$ and $R^6$ are each H, $R^3$ is halomethyl and $R^7$ is OH.

In other embodiments, the compound is a compound of formula II wherein $R^1$, $R^2$, $R^5$ and $R^6$ are each H, $R^3$ is halogen and $R^7$ is H.

In other embodiments, the compound is a compound of formula II wherein $R^1$, $R^2$, $R^5$ and $R^6$ are each H, $R^3$ is OH and $R^7$ is halogen.

In other embodiments, the compound is a compound of formula II wherein $R^1$, $R^2$, $R^5$ and $R^6$ are each $CH_3$, $R^3$ is halogen and $R^7$ is $OCH_3$.

In other embodiments, the compound is a compound of formula II wherein $R^1$, $R^2$, $R^5$ and $R^6$ are each $CH_3$, and $R^3$ and $R^7$ are each halogen.

In other embodiments, the compound is a compound of formula II wherein $R^4$ is hydrogen.

In other embodiments, the compound is a compound of formula II wherein $R^1$, $R^2$, $R^5$ and $R^6$ are each hydrogen.

In other embodiments, the compound is a compound of formula II wherein $R^1$, $R^2$, $R^5$ and $R^6$ are each $CH_3$.

In other embodiments, the compound is a compound of formula II wherein $R^3$ and $R^7$ are each hydrogen, halogen, halomethyl, OH or $OCH_3$.

In other embodiments, the compound is a compound of formula II wherein $R^1$, $R^2$, $R^5$ and $R^6$ are each H, $R^3$ is halogen and $R^7$ is OH.

In other embodiments, the compound is a compound of formula II wherein $R^1$, $R^2$, $R^5$ and $R^6$ are each H, and $R^3$ and $R^7$ are each halogen.

In other embodiments, the compound is a compound of formula II wherein $R^1$, $R^2$, $R^5$ and $R^6$ are each H, $R^3$ is halomethyl and $R^7$ is OH.

In other embodiments, the compound is a compound of formula II wherein $R^1$, $R^2$, $R^5$ and $R^6$ are each H, $R^3$ is halogen and $R^7$ is H.

In other embodiments, the compound is a compound of formula II wherein $R^1$, $R^2$, $R^5$ and $R^6$ are each H, $R^3$ is OH and $R^7$ is halogen.

In other embodiments, the compound is a compound of formula II wherein $R^3$ is halogen and $R^7$ is $OCH_3$.

In other embodiments, the compound is a compound of formula II wherein $R^1$, $R^2$, $R^5$ and $R^6$ are each $CH_3$, and $R^3$ and $R^7$ are each halogen.

In other embodiments, the compound of formula (II) is represented by any of the following compounds:

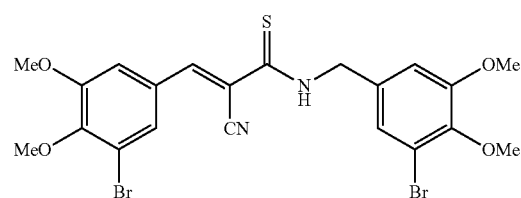

II-2

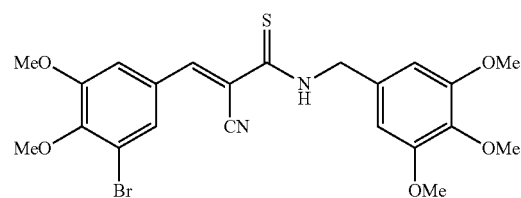

II-3

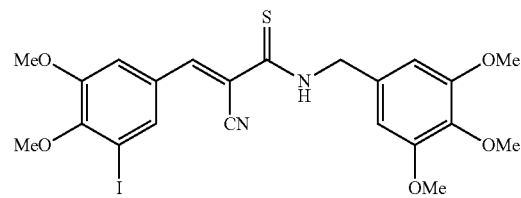

II-4

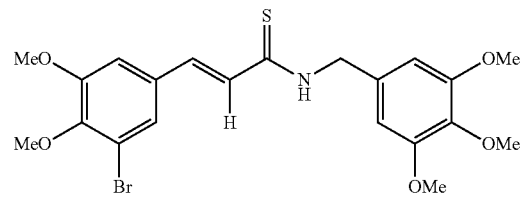

II-5

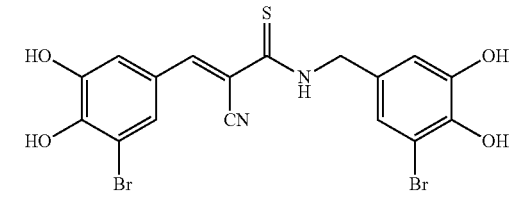

II-6

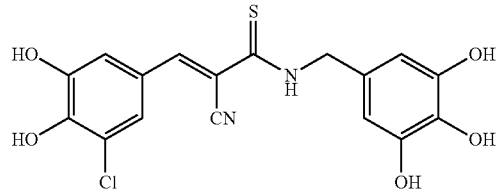

II-11

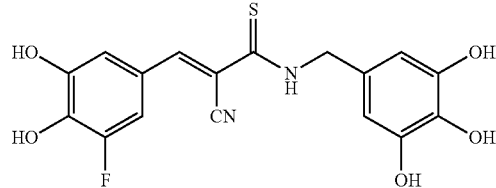

II-12

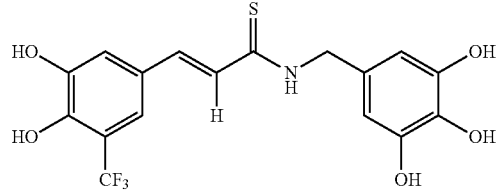

II-14

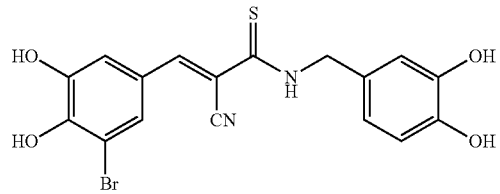

II-15

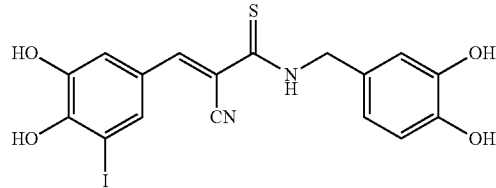

II-16

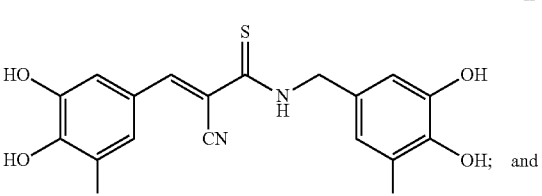

II-17 and

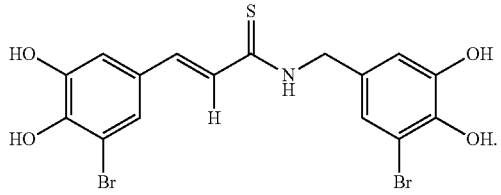

II-18

Each possibility represents a separate embodiment of the present invention. In another embodiment, the compound is represented by the structure of formula III:

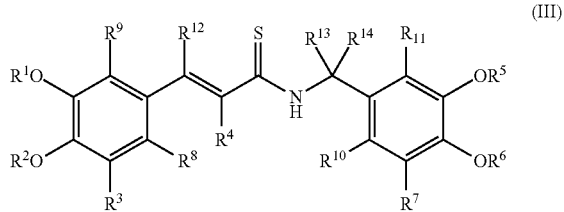

(III)

wherein
$R^1$, $R^2$, $R^5$ and $R^6$ are independently selected from H, $C_1$-$C_4$ alkyl, $(CH_2CH_2O)_nH$ wherein n is an integer of 1 to 20, acyl and a functional group that gives rise to hydroxyl upon hydrolysis;
$R^3$, $R^7$, $R^8$, $R^9$, $R^{10}$, $R^{11}$, $R^{12}$, $R^{13}$ and $R^{14}$ are independently selected from H, halogen, $C_1$-$C_4$ alkyl, haloalkyl and $OR^{16}$ wherein $R^{16}$ is H, $C_1$-$C_4$ alkyl, $(CH_2CH_2O)_n$H, acyl or a functional group that gives rise to hydroxyl upon hydrolysis; and
$R^4$ is H or CN.

In other embodiments, the compound is represented by the structure of formula IV:

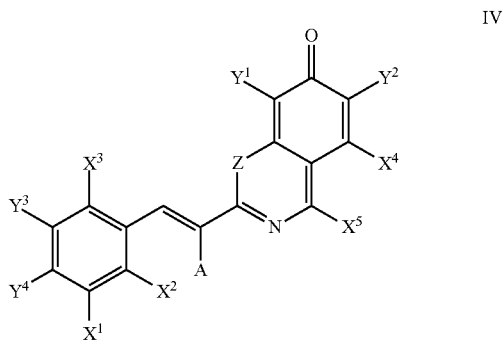

IV wherein
A is H or CN;
Z is S, SO or $SO_2$;
$X^1$, $X^2$, $X^3$, $X^4$, $X^5$, $Y^1$ and $Y^2$ are each independently selected from H, halogen, alkyl, haloalkyl and $OR^1$; and
$Y^3$ and $Y^4$ are each $OR^1$, wherein each IV is independently H, $C_1$-$C_4$ alkyl, —$(CH_2CH_2O)_n$H wherein n is an integer of 1 to 20, acyl or a functional group that gives rise to hydroxyl upon hydrolysis, including salts, hydrates, solvates, polymorphs, optical isomers, geometrical isomers, enantiomers, diastereomers, and mixtures thereof.

In some embodiments, the compound is a compound of formula IV wherein A is H.
In other embodiments, the compound is a compound of formula IV wherein A is CN.
In other embodiments, the compound is a compound of formula IV wherein Z is S.
In other embodiments, the compound is a compound of formula IV wherein Z is $SO_2$.
In other embodiments, the compound is a compound of formula IV wherein at least one of $X^1$, $X^2$, $X^3$, $X^4$, $Y^1$ and $Y^2$ is a halogen.
In other embodiments, the compound is a compound of formula IV wherein at least one of $X^1$, $X^2$, $X^3$, $X^4$, $Y^1$ and $Y^2$ is Br.
In other embodiments, the compound is a compound of formula IV wherein at least one of $X^1$, $X^2$, $X^3$, $X^4$, $Y^1$ and $Y^2$ is I.
In other embodiments, the compound is a compound of formula IV wherein $X^1$, $X^2$, $X^3$, and $X^4$ are each selected from H or a halogen, wherein the halogen is preferably Br or I.
In other embodiments, the compound is a compound of formula IV wherein $X^2$ is H.
In other embodiments, the compound is a compound of formula IV wherein $X^5$ is H.
In other embodiments, the compound is a compound of formula IV wherein $X^5$ is alkyl, preferably methyl.
In other embodiments, the compound is a compound of formula IV wherein $Y^3$ and $Y^4$ are each OH.
In other embodiments, the compound is a compound of formula IV wherein $Y^1$ and $Y^2$ are each OH.
In other embodiments, the compound is a compound of formula IV wherein A is H, Z is S, $Y^3$ and $Y^4$ are each OH, and $X^1$ is a halogen selected from Br and I.

Each possibility represents a separate embodiment of the present invention.

In other embodiments, the compound of formula (IV) is represented by any of the following compounds:

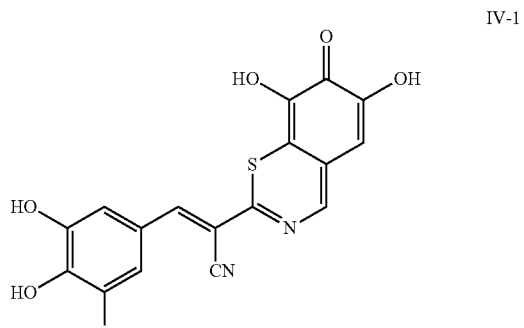

IV-1

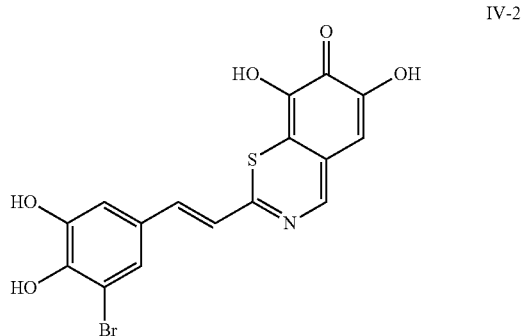

IV-2

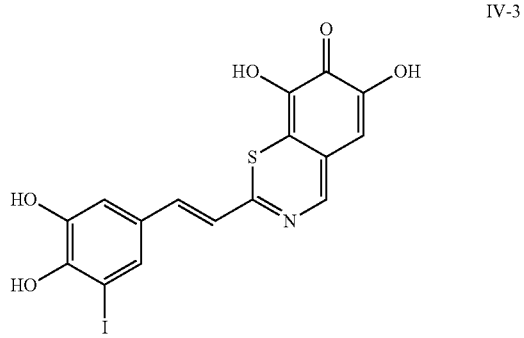

IV-3

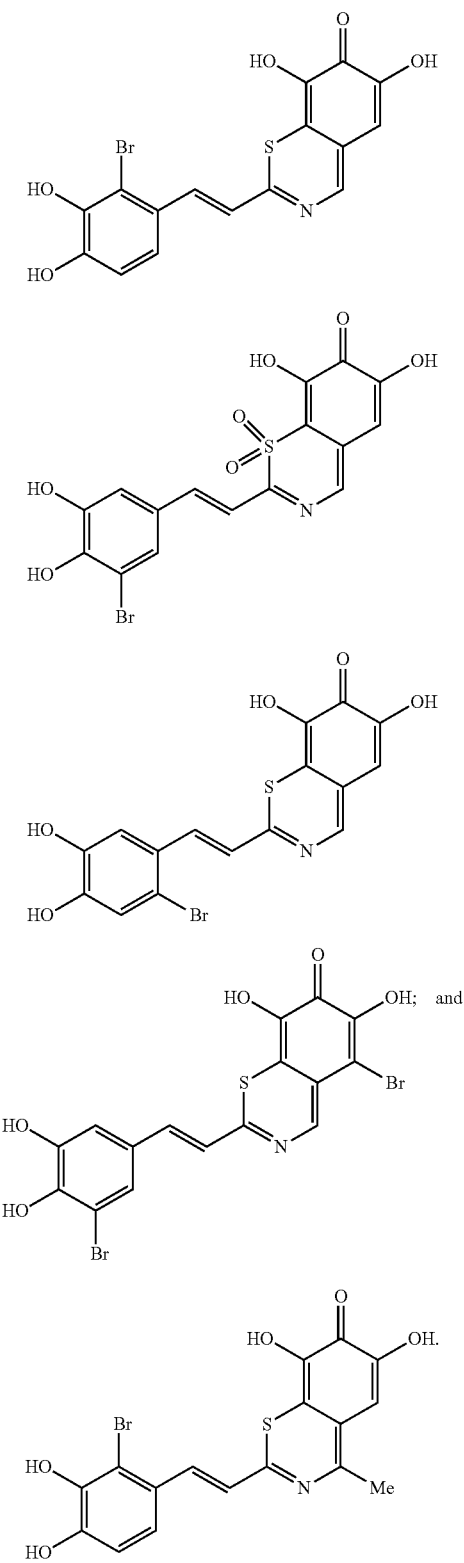

A currently preferred compound of formula IV is a compound of formula IV-4.

In other embodiments, the compound is any of the derivatives described in A) PCT International Patent Application Publication No. WO 2008/068751; B) PCT International Patent Application Publication No. WO 2009/147682; or C) PCT International patent Application No. WO 2012/090204. The contents of each of the aforementioned references are incorporated by reference herein in their entirety as if fully set forth herein.

It is understood that all conformers, geometrical isomers, stereoisomers, enantiomers and diastereomers of any of the compounds described herein, are encompassed and may be used in the combinations and methods described by the present application.

Without being bound to any particular theory or mechanism of action, it is contemplated that the compounds of the present invention are inhibitors of PK signaling, such as IGF-1R. It has now been surprisingly found that these compounds, in addition to being inhibitors of IGF-1R, also lead to the dissociation of the IGF-1R substrates IRS1/2 from the cell membrane, inhibitory serine phosphorylation and/or degradation of the IRS1/2 proteins. This activity leads to long lasting inhibition of the IGF-1R and IR pathways, growth inhibition of a wide range of cancer cell types, and potent anti-tumor effects. These compounds are therefore referred to as "modulators of IRS". Thus, in another embodiment, the present invention provides a method of inhibiting, treating or preventing an insulin-like growth factor 1 receptor (IGF-1R) and/or insulin receptor substrate 1 (IRS1) and/or insulin receptor substrate 2 (IRS2) signaling related disorder in a subject comprising the step of administering to the subject a pharmaceutical composition comprising a therapeutically effective amount of at least one compound represented by the structure of formula I or any of the compounds covered by such formula, together with an anti-cancer agent selected from EGFR inhibitor, EGFR antibody, mTOR inhibitor and/or immunotherapy agent, wherein the compound of formula I and the anti-cancer agent together provide an anti-cancer effect which is at least additive, and is preferably synergistic. In some embodiments, the compound of formula I is an inhibitor of an insulin receptor or an insulin-like growth factor-1 receptor (IGF-1R) signaling, and/or the compound of formula I interacts with, affects or inhibits a substrate protein in the IGF-1R mediated pathway. In some embodiments, the substrate protein is Insulin Receptor Substrate 1 (IRS1), Insulin Receptor Substrate 2 (IRS2), or a combination thereof. In one particular embodiment, the compound of formula I is an IGF-1R kinase inhibitor that leads to at least one of the dissociation of IRS1 or IRS2 from the cell membrane, phosphorylation of IRS1 or IRS2, and/or degradation of IRS1 or IRS2, in any order.

IGF1R and specifically IRS1 are one of the key mechanisms for resistance to EGFR inhibition (Buck E. et al. Feedback mechanisms promote cooperativity for small molecule inhibitors of epidermal and insulin-like growth factor receptors. *Cancer Res.* 2008 Oct. 15; 68(20):8322-32).

The compounds described herein are also modulators of signal transducer and activator of transcription 3 (Stat3). In some embodiments, the compounds lead to the inhibition of Stat3 phosphorylation in cancer cells. Increased levels of Stat3 phosphorylation are detected in various cancers and drug-resistant cancers, leading to enhanced cancer survival. Without wishing to be bound by any particular theory or mechanism of action it is contemplated that inhibiting Stat3 activity may synergize with such PK inhibitor drugs, which as a side effect upregulate Stat3, may prevent acquired resistance to such drugs and may be effective for drug-resistant cancers. Furthermore, Stat3 is often activated in cancer and directly involved in the implementation and maintenance of the cancer immunosuppressive microenvironment and plays a central role in tumor immune evasion. Without wishing to be bound by any particular theory or mechanism of action, it is contemplated that inhibition of Stat3 phosphorylation un-masks the tumor from the local immune system and sensitize them to immunotherapy e.g. antibodies against PDLs, PD1, CTLA4 or any other immunotherapy agents.

Chemical Definitions

An "alkyl" group refers to any saturated aliphatic hydrocarbon, including straight-chain and branched-chain alkyl groups. In one embodiment, the alkyl group has 1-12 carbons designated here as $C_1$-$C_{12}$-alkyl. In another embodiment, the alkyl group has 1-6 carbons designated here as $C_1$-$C_6$-alkyl. In another embodiment, the alkyl group has 1-4 carbons designated here as $C_1$-$C_4$-alkyl. The alkyl group may be unsubstituted or substituted by one or more groups selected from halogen, hydroxy, alkoxy carbonyl, amido, alkylamido, dialkylamido, nitro, amino, alkylamino, dialkylamino, carboxyl, thio and thioalkyl.

An "alkenyl" group refers to an aliphatic hydrocarbon group containing at least one carbon-carbon double bond including straight-chain, branched-chain and cyclic alkenyl groups. In one embodiment, the alkenyl group has 2-8 carbon atoms designated here as $C_2$-$C_8$-alkenyl. In another embodiment, the alkenyl group has 2-6 carbon atoms in the chain designated here as $C_2$-$C_6$-alkenyl. Exemplary alkenyl groups include ethenyl, propenyl, n-butenyl, i-butenyl, 3-methylbut-2-enyl, n-pentenyl, heptenyl, octenyl, cyclohexyl-butenyl and decenyl. The alkenyl group can be unsubstituted or substituted through available carbon atoms with one or more groups defined hereinabove for alkyl.

An "alkynyl" group refers to an aliphatic hydrocarbon group containing at least one carbon-carbon triple bond including straight-chain and branched-chain. In one embodiment, the alkynyl group has 2-8 carbon atoms in the chain designated here as $C_2$-$C_8$-alkynyl. In another embodiment, the alkynyl group has 2-6 carbon atoms in the chain designated here as $C_2$-$C_6$-alkynyl. Exemplary alkynyl groups include ethynyl, propynyl, n-butynyl, 2-butynyl, 3-methylbutynyl, n-pentynyl, heptynyl, octynyl and decynyl. The alkynyl group can be unsubstituted or substituted through available carbon atoms with one or more groups defined hereinabove for alkyl.

The term "$C_3$-$C_7$ cycloalkyl" used herein alone or as part of another group refers to any saturated or unsaturated (e.g., cycloalkenyl, cycloalkynyl) monocyclic or polycyclic group. Non-limiting examples of cycloalkyl groups are cyclopropyl, cyclobutyl, cyclopentyl, cyclohexyl or cycloheptyl. Non-limiting examples of cycloalkenyl groups include cyclopentenyl, cyclohexenyl and the like. The cycloalkyl group can be unsubstituted or substituted with any one or more of the substituents defined above for alkyl. Similarly, the term "cycloalkylene" means a bivalent cycloalkyl, as defined above, where the cycloalkyl radical is bonded at two positions connecting together two separate additional groups.

The term "aryl" used herein alone or as part of another group refers to an aromatic ring system containing from 6-14 ring carbon atoms. The aryl ring can be a monocyclic, bicyclic, tricyclic and the like. Non-limiting examples of aryl groups are phenyl, naphthyl including 1-naphthyl and 2-naphthyl, and the like. The aryl group can be unsubstituted or substituted through available carbon atoms with one or more groups defined hereinabove for alkyl.

The term "heteroaryl" used herein alone or as part of another group refers to a heteroaromatic system containing at least one heteroatom ring wherein the atom is selected from nitrogen, sulfur and oxygen. The heteroaryl contains 5 or more ring atoms. The heteroaryl group can be monocyclic, bicyclic, tricyclic and the like. Also included in this definition are the benzoheterocyclic rings. If nitrogen is a ring atom, the present invention also contemplates the N-oxides of the nitrogen containing heteroaryls. Non-limiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, naphthyridinyl, quinoxalinyl, quinazolinyl, cinnolinyl, pteridinyl, carbolinyl, thiazolyl, oxazolyl, isothiazolyl, isoxazolyl and the like. The heteroaryl group can be unsubstituted or substituted through available atoms with one or more groups defined hereinabove for alkyl.

The term "heterocyclic ring" or "heterocyclyl" used herein alone or as part of another group refers to a five-membered to eight-membered rings that have 1 to 4 heteroatoms, such as oxygen, sulfur and/or nitrogen, in particular nitrogen, either alone or in conjunction with sulfur or oxygen ring atoms. These five-membered to eight-membered rings can be saturated, fully unsaturated or partially unsaturated, with fully saturated rings being preferred. Preferred heterocyclic rings include piperidinyl, pyrrolidinyl pyrrolinyl, pyrazolinyl, pyrazolidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl, tetrahydropyranyl, dihydrothiazolyl, and the like. The heterocyclyl group can be unsubstituted or substituted through available atoms with one or more groups defined hereinabove for alkyl.

The term "acyl" as used herein encompasses groups such as, but not limited to, formyl, acetyl, propionyl, butyryl, pentanoyl, pivaloyl, hexanoyl, heptanoyl, octanoyl, nonanoyl, decanoyl, undecanoyl, dodecanoyl, benzoyl and the like. Currently preferred acyl groups are acetyl and benzoyl.

A "hydroxy" group refers to an OH group. An "alkoxy" group refers to an —O-alkyl group wherein R is alkyl as defined above.

A "thio" group refers to an —SH group. An "alkylthio" group refers to an —SR group wherein R is alkyl as defined above.

An "amino" group refers to an $NH_2$ group. An alkylamino group refers to an —NHR group wherein R is alkyl is as defined above. A dialkylamino group refers to an —NRR' group wherein R and R' are alkyl as defined above.

An "amido" group refers to a —C(O)$NH_2$ group. An alkylamido group refers to an —C(O)NHR group wherein R is alkyl is as defined above. A dialkylamido group refers to an —C(O)NRR' group wherein R and R' are alkyl as defined above.

A "thioamide" group refers to a —C(S)NHR group, where R is either alkyl, aryl, alkylaryl or H.

A "polyoxyalkylene" group refers to a $(CH_2CH_2O)_nH$ group wherein n=1-20. Currently preferred polyoxyalkylene groups are polyethyleneglycol (PEG) and polypropyleneglycol.

The term "halogen" or "halo" as used herein alone or as part of another group refers to chlorine, bromine, fluorine, and iodine. The term "haloalkyl" refers to an alkyl group having some or all of the hydrogens independently replaced by a halogen group including, but not limited to, trichloromethyl, tribromomethyl, trifluoromethyl, triiodomethyl, difluoromethyl, chlorodifluoromethyl, pentafluoroethyl, 1,1-difluoroethyl bromomethyl, chloromethyl, fluoromethyl, iodomethyl, and the like.

Examples of functional groups that give rise to hydroxyl upon hydrolysis include, but are not limited to, esters, anhydrides, carbamates, carbonates and the like. For example, when any of $R^1$, $R^2$, $R^5$ or $R^6$ is an acyl group (COR), the resulting functional group is an ester (OCOR). When any of $R^1$, $R^2$, $R^5$ or $R^6$ is an amide group (CONHR), the resulting functional group is a carbamate (OCONHR). When any of $R^1$, $R^2$, $R^5$ or $R^6$ is a carboxylate group (COOR), the resulting functional group is a carbonate (OCOOR).

Within the scope of the present invention are prodrugs of the compounds disclosed herein. The term "prodrug" represents compounds which are rapidly transformed in vivo to any of compounds represented by formula I, for example by hydrolysis in the blood. Thus, the term "prodrug" refers to a precursor of any of the compounds of the present invention that is pharmaceutically acceptable. A prodrug may be inactive when administered to a subject, but is converted in vivo to an active compound. The use of prodrugs is particularly advantageous for facilitating the administration of the compounds. The prodrug compound often offers benefits of solubility, tissue compatibility or delayed release in a mammalian organism. For example the prodrug, according to the principles of the present invention, can be a compound represented by the structure of formula I wherein $R^1$, $R^2$, $R^5$ and $R^6$ are a functional group that gives rise to hydroxyl upon hydrolysis as defined hereinabove.

All stereoisomers of the above compounds are contemplated, either in admixture or in pure or substantially pure form. The compounds can have asymmetric centers at any of the atoms. Consequently, the compounds can exist in enantiomeric or diastereomeric forms or in mixtures thereof. The present invention contemplates the use of any racemates (i.e. mixtures containing equal amounts of each enantiomers), enantiomerically enriched mixtures (i.e., mixtures enriched for one enantiomer), pure enantiomers or diastereomers, or any mixtures thereof. The chiral centers can be designated as R or S or R,S or d,D, l,L or d,l, D,L. Compounds comprising amino acid residues include residues of D-amino acids, L-amino acids, or racemic derivatives of amino acids. Compounds comprising sugar residues include residues of D-sugars, L-sugars, or racemic derivatives of sugars. Residues of D-sugars, which appear in nature, are preferred. In addition, several of the compounds of the invention contain one or more double bonds. The present invention intends to encompass all structural and geometrical isomers including cis, trans, E and Z isomers, independently at each occurrence.

One or more of the compounds of the invention, may be present as a salt. The term "salt" encompasses both basic and acid addition salts, including but not limited to, carboxylate salts or salts with amine nitrogens, and include salts formed with the organic and inorganic anions and cations discussed below. Furthermore, the term includes salts that form by standard acid-base reactions with basic groups (such as amino groups) and organic or inorganic acids. Such acids include hydrochloric, hydrofluoric, trifluoroacetic, sulfuric, phosphoric, acetic, succinic, citric, lactic, maleic, fumaric, palmitic, cholic, pamoic, mucic, D-glutamic, D-camphoric, glutaric, phthalic, tartaric, lauric, stearic, salicylic, methanesulfonic, benzenesulfonic, sorbic, picric, benzoic, cinnamic, and like acids. Each possibility represents a separate embodiment of the invention.

The term "organic or inorganic cation" refers to counter-ions for the anion of a salt. The counter-ions include, but are not limited to, alkali and alkaline earth metals (such as lithium, sodium, potassium, barium, aluminum and calcium); ammonium and mono-, di- and tri-alkyl amines such as trimethylamine, cyclohexylamine; and the organic cations, such as dibenzylammonium, benzylammonium, 2-hydroxyethylammonium, bis(2-hydroxyethyl)ammonium, phenylethylbenzylammonium, dibenzylethylenediammonium, and like cations. See, for example, Berge et al., *J. Pharm. Sci.* (1977), 66:1-19, which is incorporated herein by reference.

The present invention also includes solvates of the compounds of the present invention and salts thereof. "Solvate" means a physical association of a compound of the invention with one or more solvent molecules. This physical association involves varying degrees of ionic and covalent bonding, including hydrogen bonding. In certain instances the solvate will be capable of isolation. "Solvate" encompasses both solution-phase and isolatable solvates. Non-limiting examples of suitable solvates include ethanolates, methanolates and the like. "Hydrate" is a solvate wherein the solvent molecule is water.

The present invention also includes polymorphs of the compounds of the present invention and salts thereof. The term "polymorph" refers to a particular crystalline or amorphous state of a substance, which can be characterized by particular physical properties such as X-ray diffraction, IR or Raman spectra, melting point, and the like.

IRS/Stat3 Dual Modulators and EGFR Inhibitors/Antibody Combinations

In one embodiment, the present invention relates to a method of treating a tumor that has developed resistance to an Epidermal Growth Factor Receptor (EGFR) inhibitor and/or EGFR antibody, the method comprising the step of contacting the tumor with an EGFR inhibitor and/or EGFR antibody in combination with a compound of any of formulae (I), (II), (III), (IV), or any of the individual compounds covered by such formulae.

In another embodiment, the present invention relates to a method of preventing acquired resistance of a tumor to an Epidermal Growth Factor Receptor (EGFR) inhibitor and/or EGFR antibody, the method comprising the step of contacting the tumor with an EGFR inhibitor and/or EGFR antibody in combination with a compound of any of formulae (I), (II), (III), (IV), or any of the individual compounds covered by such formulae.

In another embodiment, the present invention relates to a pharmaceutical combination comprising a compound represented by the structure of any of formulae (I), (II), (III), (IV), or any of the individual compounds covered by such formulae, in combination with an Epidermal Growth Factor (EGFR) inhibitor and/or EGFR antibody.

In other embodiments, the present invention further relates to the combination as described above for use in treating a tumor that is resistant to an EGFR inhibitor and/or EGFR antibody, or for preventing acquired resistance to an EGFR inhibitor and/or EGFR antibody.

In other embodiments, the present invention further relates to the use of the combination described above for the preparation of a medicament for the treatment of a tumor that is resistant to an EGFR inhibitor and/or EGFR antibody, or for preventing acquired resistance to an EGFR inhibitor and/or EGFR antibody.

In some embodiments, the tumor is present in a cancer patient having tumors with acquired resistance to EGFR inhibitor and/or EGFR antibody treatment. In other embodiments, the treatment results in attenuation or regression in the growth of the resistant tumors. In other embodiments, the tumor is present in a cancer patient who is receiving treatment with an EGFR inhibitor and/or EGFR antibody or is a candidate for receiving such treatment.

Any EGFR inhibitor or antibody known to a person of skill in the art may be used in the combinations of the present invention. In some embodiments, the EGFR inhibitor is selected from the group consisting of erlotinib, gefitinib, lapatinib, vandetanib, neratinib, icotinib, afatinib, dacomitinib, poziotinib, AZD9291, CO-1686, HM61713 and AP26113. In one currently preferred embodiment, the EGFR inhibitor is erlotinib. In one specific embodiment, the compound is represented by the structure of formula D and the EGFR inhibitor is erlotinib. Each possibility represents a separate embodiment of the present invention.

In some embodiments, the EGFR antibody is selected from the group consisting of trastuzumab, necitumumab. cetuximab and panitumumab. Each possibility represents a separate embodiment of the present invention.

In one embodiment, the compound is a compound of formula A. In another embodiment, the compound is a compound of formula B. In another embodiment, the compound is a compound of formula C. In another embodiment, the compound is a compound of formula D. In another embodiment, the compound is a compound of formula E. In another embodiment, the compound is a compound of formula F. In another embodiment, the compound is a compound of formula G. In another embodiment, the compound is a compound of formula H. In another embodiment, the compound is a compound of formula I. In another embodiment, the compound is a compound of formula J. In another embodiment, the compound is a compound of formula IV-4. In one currently preferred embodiment, the compound is represented by the structure of formula D. However, it is apparent to one of skill in the art that any of the compounds described herein may be used in the combinations of the present invention.

IRS/Stat3 Dual Modulators and mTOR Inhibitor Combinations

In further aspects of the present invention, it has now unexpectedly been found that a combination of an IRS/Stat3 dual modulator of any of formulae (I), (II), (III), (IV), or any of the individual compounds covered by such formulae as described herein, and an inhibitor of mammalian target of rapamycin (mTOR), provides a therapeutic effect that is at least additive, and is preferably synergistic as compared with the treatment effect of each agent alone. Furthermore, the combination can be used to treat a tumor that has developed resistance to an mTOR inhibitor, and/or to prevent acquired resistance of a tumor to the mTOR inhibitor.

Accordingly, in one embodiment, the present invention relates to a pharmaceutical combination comprising a compound represented by the structure of any of formulae (I), (II), (III), (IV), or any of the individual compounds covered by such formulae and at least one inhibitor of mammalian target of rapamycin (mTOR), wherein the compound and the at least one mTOR inhibitor together provide a synergistic therapeutic anti-cancer effect In another embodiment, the present invention relates to a method of treating cancer, comprising the step of administering to the subject in need thereof a therapeutically effective amount of a pharmaceutical combination comprising a compound represented by the structure of any of formulae (I), (II), (III), (IV), and at least one inhibitor of mammalian target of rapamycin (mTOR), wherein the compound and the at least one mTOR inhibitor together provide a synergistic therapeutic effect.

In another embodiment, the present invention relates to a method of treating a tumor that has developed resistance to an inhibitor mammalian target of Rapamycin (mTOR), the method comprising the step of contacting the tumor with mTOR inhibitor in combination with a Compound of any of formulae (I), (II), (III), (IV), or any of the individual compounds covered by such formulae.

In another embodiment, the present invention relates to a method of preventing acquired resistance of a tumor to an inhibitor mammalian target of Rapamycin (mTOR), the method comprising the step of contacting the tumor with an mTOR inhibitor in combination with a Compound of any of formulae (I), (II), (III), (IV), or any of the individual compounds covered by such formulae.

In other embodiments, the present invention further relates to the combination as described above for use in treating a tumor that is resistant to an mTOR inhibitor, or for preventing acquired resistance to an mTOR inhibitor.

In other embodiments, the present invention further relates to the use of the combination described above for the preparation of a medicament for the treatment of a tumor that is resistant to an mTOR inhibitor, or for preventing acquired resistance to an mTOR inhibitor.

In other embodiments, the present invention further relates to a combination as described above, for use in treating a tumor that is resistant to an mTOR inhibitor, or for preventing acquired resistance to an mTOR inhibitor.

In some embodiments, the tumor is present in a cancer patient having tumors with acquired resistance to mTOR inhibitor treatment. In other embodiments, the treatment results in attenuation or regression in the growth of the resistant tumors. In other embodiments, the tumor is present in a cancer patient who is receiving treatment with an mTOR inhibitor or is a candidate for receiving such treatment.

Any mTOR inhibitor known to a person of skill in the art may be used in the combinations of the present invention. In some embodiments, the mTOR inhibitor is a first generation inhibitor selected from the group consisting of rapamycin (Sirolimus); Ridaforolimus (Deforolimus, AP23573, MK-8669); NVP-BEZ235 (2-Methyl-2-{4-[3-methyl-2-oxo-8-(quinolin-3-yl)-2,3-dihydro-1H-imidazo[4,5-c]quinolin-1-yl]phenyl}propanenitrile); Everolimus (Afinitor, RAD-001, the 40-O-(2-hydroxyethyl) derivative of sirolimus); and Temsirolimus (CCI-779). In a currently preferred embodiment, thee mTOR inhibitor is Everolimus.

In other embodiments, the mTOR inhibitor is a second generation compound (inhibitor of mTORC1 and mTORC2), such as OSI-027 (trans-4-[4-Amino-5-(7-methoxy-1H-indol-2-yl)imidazo[5,1-f][1,2,4]triazin-7-yl]cyclohexanecarboxylic acid); XL765 (SAR245409); INK128 (3-(2-amino-5-benzoxazolyl)-1-(1-methylethyl)-1H-pyrazolo[3,4-d]pyrimidin-4-amine); MLN0128, AZD2014 (3-(2,4-bis((S)-3-methylmorpholino)pyrido[2,3-d]pyrimidin-7-yl)-N-methylbenzamide); DS-3078a and Palomid529 (3-(4-methoxybenzyloxy)-8-(1-hydroxyethyl)-2-methoxy-6H-benzo[c]chromen-6-one).

In one specific embodiment, the compound is represented by the structure of formula D and the mTOR inhibitor is Everolimus (Afinitor).

In one embodiment, the compound is a compound of formula A. In another embodiment, the compound is a compound of formula B. In another embodiment, the compound is a compound of formula C. In another embodiment, the compound is a compound of formula D. In another embodiment, the compound is a compound of formula E. In another embodiment, the compound is a compound of formula F. In another embodiment, the compound is a compound of formula G. In another embodiment, the compound is a compound of formula H. In another embodiment, the compound is a compound of formula I. In another embodiment, the compound is a compound of formula J. In another embodiment, the compound is a compound of formula IV-4. In one currently preferred embodiment, the compound is represented by the structure of formula D. However, it is apparent to one of skill in the art that any of the compounds described herein may be used in the combinations of the present invention.

IRS/Stat3 Dual Modulators and Immunotherapy Agent Combinations

In one embodiment, the present invention relates to a method of sensitizing a tumor to immunotherapy, the method comprising the step of contacting the tumor with a compound of any of formulae (I), (II), (III), (IV), or any of the individual compounds covered by such formulae in combination with an immunotherapy agent.

In another embodiment, the present invention relates to a pharmaceutical combination comprising a compound represented by the structure of any of formulae (I), (II), (III), (IV), or any of the individual compounds covered by such formulae, in combination with an immunotherapy agent.

In other embodiments, the present invention further relates to the combination as described above for use in the treatment of a tumor by sensitizing the tumor to immunotherapy.

In other embodiments, the present invention further relates to the use of the combination described above for the preparation of a medicament for the treatment of a tumor by sensitizing the tumor to immunotherapy.

In some embodiments, the tumor is present in a cancer patient who is receiving immunotherapy or is a candidate for receiving immunotherapy.

Any immunotherapy agent that is known to a person of skill in the art can be used in the combination of the present invention. In some embodiments, the immunotherapy agent is an antibody against a target selected from the group consisting of PDL, PD1, CTLA4, CD20, CD30, CD33, CD52, VEGF, CD30, EGFR and ErbB2. In some embodiments, the antibody is selected from the group consisting of Alemtuzumab (Campath®), Bevacizumab (Avastin®), Brentuximab vedotin (Adcetris®), Cetuximab (Erbitux®), Gemtuzumab ozogamicin (Mylotarg®), Ibritumomab tiuxetan (Zevalin®), Ipilimumab (Yervoy®), Ofatumumab (Arzerra®), Panitumumab (Vectibix®), Rituximab (Rituxan®), Tositumomab (Bexxar®) and Tratuzumab (Herceptin®). Each possibility represents a separate embodiment of the present invention.

In one embodiment, the compound is a compound of formula A. In another embodiment, the compound is a compound of formula B. In another embodiment, the compound is a compound of formula C. In another embodiment, the compound is a compound of formula D. In another embodiment, the compound is a compound of formula E. In another embodiment, the compound is a compound of formula F. In another embodiment, the compound is a compound of formula Ga. In another embodiment, the compound is a compound of formula H. In another embodiment, the compound is a compound of formula I. In another embodiment, the compound is a compound of formula J. In another embodiment, the compound is a compound of formula IV-4. In one currently preferred embodiment, the compound is represented by the structure of formula D. However, it is apparent to one of skill in the art that any of the compounds described herein may be used in the combinations of the present invention.

IRS/Stat3 Dual Modulators and Mitogen-Activated Protein Kinase (MEK) Inhibitor and/or a Mutated B-Raf Inhibitor Combinations In other aspects, it has now unexpectedly been found that a combination of a dual modulator of Insulin Receptor Substrate (IRS) and signal transducer and activator of transcription 3 (Stat3), as described herein, and a mitogen-activated protein kinase (MEK) inhibitor and/or a mutated B-Raf inhibitor, provides a therapeutic effect that is at least additive, and is preferably synergistic as compared with the treatment effect of each agent alone. Furthermore, the combination can be used to treat a tumor that has developed resistance to a MEK inhibitor and/or mutated B-Raf inhibitor, and/or to prevent acquired resistance of a tumor to a MEK inhibitor and/or mutated B-Raf inhibitor and/or to prevent or delay delaying tumor recurrence following cease of treatment with a MEK inhibitor and/or mutated B-Raf inhibitor.

Thus, in some embodiments, the present invention relates to a method of treating a tumor that has developed resistance to a mitogen-activated protein kinase (MEK) inhibitor and/or a mutated B-Raf inhibitor, the method comprising the step of contacting the tumor with a MEK inhibitor and/or mutated B-Raf inhibitor, in combination with a compound represented by the structure of formula (III) or (IV).

In other embodiments, the present invention relates to method of preventing acquired resistance of a tumor to a MEK inhibitor and/or mutated B-Raf inhibitor, the method comprising the step of contacting the tumor with a MEK inhibitor and/or mutated B-Raf inhibitor, in combination with a compound represented by the structure of formula (III) or (IV).

In other embodiments, the present invention relates to a method of preventing or delaying tumor recurrence following cease of treatment with a MEK inhibitor and/or a mutated B-Raf inhibitor, the method comprising the step of contacting the tumor with a MEK inhibitor and/or mutated B-Raf inhibitor, in combination with a compound represented by the structure of formula (III) or (IV).

In other embodiments, the present invention relates to a pharmaceutical combination comprising a compound represented by the structure of formula (III), in combination with a mitogen-activated protein kinase (MEK) inhibitor, and optionally a mutated B-Raf inhibitor. In some embodiments, the combination comprises a compound of formula (III), a MEK inhibitor and a mutated B-Raf inhibitor preferably, wherein the MEK inhibitor is Trametinib, and the mutated B-Raf inhibitor is Vemurafenib.

In other embodiments, the present invention relates to a compound represented by the structure of formula (IV), in combination with a mitogen-activated protein kinase (MEK) inhibitor, and/or a mutated B-Raf inhibitor.

In some embodiments, the tumor is present in a cancer patient having tumors with acquired resistance to MEK inhibitor and/or mutated B-Raf inhibitor treatment. In other embodiments, the treatment results in attenuation or regression in the growth of the resistant tumors. In other embodiments, the tumor is present in a cancer patient who is receiving treatment with an MEK inhibitor and/or a mutated B-Raf inhibitor or is a candidate for receiving such treatment.

Any MEK inhibitor known to a person of skill in the art may be used in the combinations of the present invention. In some embodiments, the MEK inhibitor is selected from the group consisting of Trametinib (GSK1120212), Selumetinib, Binimetinib (MEK162), PD-325901, Cobimetinib, CI-1040 and PD035901, preferably, wherein the MEK inhibitor is Trametin.

Any mutated B-Raf inhibitor known to a person of skill in the art may be used in the combinations of the present invention. In some embodiments, the mutated B-Raf inhibitor is selected from the group consisting of Vemurafenib (PLX-4032), PLX4720, Sorafenib (BAY43-9006), and Dabrafenib, preferably, wherein the mutated B-Raf inhibitor is Vemurafenib.

In one embodiment, the compound is represented by the structure of formula (III). In another embodiment, the compound is represented by the structure of formula (IV). Each possibility represents a separate embodiment of the present invention.

In some embodiments, the compound is represented by the structure of formula D and the MEK inhibitor is Trametinib.

In other embodiments, the compound is represented by the structure of formula D and the mutated B-Raf inhibitor is Vemurafenib.

In some embodiments, the combination treatment includes a compound of formula (III) or (IV), and either a MEK inhibitor or a mutated B-Raf inhibitor. In other embodiments, the combination treatment includes a compound of formula (III) or (IV), and both a MEK inhibitor and a mutated B-Raf inhibitor.

In some embodiments, the present invention relates to a pharmaceutical combination comprising a compound represented by the structure of formula D in combination with Trametinib.

In other embodiments, the present invention relates to a pharmaceutical combination comprising a compound represented by the structure of formula D in combination with Trametinib and Vemurafenib.

In other embodiments, the present invention relates to the combinations described above, for use in treating a tumor that is resistant to a MEK inhibitor and/or a mutated B-Raf inhibitor, or for preventing acquired resistance to a MEK inhibitor and/or a mutated B-Raf inhibitor.

In other embodiments, the present invention relates to the use of the combinations described above, for the preparation of a medicament for the treatment of a tumor that is resistant to a MEK inhibitor and/or a mutated B-Raf inhibitor, or for preventing acquired resistance to a MEK inhibitor and/or a mutated B-Raf inhibitor.

In one embodiment, the compound is a compound of formula A. In another embodiment, the compound is a compound of formula B. In another embodiment, the compound is a compound of formula C. In another embodiment, the compound is a compound of formula D. In another embodiment, the compound is a compound of formula E. In another embodiment, the compound is a compound of formula F. In another embodiment, the compound is a compound of formula Ga. In another embodiment, the compound is a compound of formula H. In another embodiment, the compound is a compound of formula I. In another embodiment, the compound is a compound of formula J. In another embodiment, the compound is a compound of formula IV-4. In one currently preferred embodiment, the compound is represented by the structure of formula D. However, it is apparent to one of skill in the art that any of the compounds described herein may be used in the combinations of the present invention.

IRS/Stat3 Dual Modulators and Chemotherapeutic Agent Combinations

In other aspects, it has now unexpectedly been found that a combination of a dual modulator of Insulin Receptor Substrate (IRS) and signal transducer and activator of transcription 3 (Stat3), as described herein, and a chemotherapeutic agent such as Gemcitabine, 5-FU, Irinotecan, Oxaliplatin and any combination thereof (e.g., the combination treatment FOLFIRI or FOLFOX), provides a therapeutic effect that is at least additive, and is preferably synergistic as compared with the treatment effect of each agent alone. Furthermore, the combination can be used to treat a tumor that has developed resistance to any of these chemotherapeutic agents or their combination and/or to prevent acquired resistance of a tumor to any of these chemotherapeutic agents or their combination, and/or to prevent or delay delaying tumor recurrence following cease of treatment with any of these therapeutic agents or their combination.

FOLFIRI is a combination treatment for cancer containing Leucovorin (Folinic Acid), 5-FU and Irinotecan. FOLFOX is a combination treatment for cancer containing Leucovorin calcium (Folinic Acid), 5-FU and Oxaliplatin.

Thus, according to some embodiments, the present invention relates to a pharmaceutical combination comprising a compound represented by the structure of formula (III) or (IV) and at least one chemotherapeutic agent selected from Gemcitabine, 5-FU, Irinotecan, Oxaliplatin and any combination thereof, wherein the compound and the chemotherapeutic agent(s) together provide a synergistic therapeutic anti-cancer effect.

In some embodiments, the present invention relates to a method of treating cancer, comprising the step of administering to the subject in need thereof a therapeutically effective amount of a combination comprising a compound represented by the structure of formula (III) or (IV) and at least one chemotherapeutic agent selected from Gemcitabine, 5-FU, Irinotecan, Oxaliplatin and any combination thereof, wherein the compound and the chemotherapeutic agent(s) together provide a synergistic therapeutic anti-cancer effect.

In other embodiments, the present invention provides a method of treating a tumor that has developed resistance to at least one chemotherapeutic agent, e.g., Gemcitabine, 5-FU, Irinotecan, Oxaliplatin and any combination thereof, the method comprising the step of contacting the tumor with at least one of said chemotherapeutic agent(s) in combination with a compound represented by the structure of formula (III) or (IV).

In other embodiments, the present invention provides a method of preventing acquired resistance of a tumor to at least one chemotherapeutic agent, e.g., Gemcitabine, 5-FU, Irinotecan, Oxaliplatin and any combination thereof, the method comprising the step of contacting the tumor with at least one of said chemotherapeutic agent(s) in combination with a compound represented by the structure of formula (III) or (IV).

In other embodiments, the present invention provides a method of preventing or delaying tumor recurrence following cease of treatment with at least one chemotherapeutic agent, e.g., Gemcitabine, 5-FU, Irinotecan, Oxaliplatin and any combination thereof, the method comprising the step of contacting the tumor with at least one of said chemotherapeutic agent(s) in combination with a compound represented by the structure of formula (III) or (IV).

In some embodiments, the tumor is present in a cancer patient having tumors with acquired resistance to said chemotherapeutic agent(s). In other embodiments, the treatment results in attenuation or regression in the growth of the resistant tumors. In other embodiments, the tumor is present in a cancer patient who is receiving treatment with said chemotherapeutic agent(s), or is a candidate for receiving such treatment.

In other embodiments, the present invention provides a pharmaceutical combination comprising a compound represented by the structure of formula (III) or (IV) and at least one chemotherapeutic agent, e.g., Gemcitabine, 5-FU, Irinotecan, Oxaliplatin and any combination thereof, for use in treating a tumor that is resistant to said chemotherapeutic agent(s), or for preventing acquired resistance to said chemotherapeutic agent(s), or for delaying tumor recurrence following cease of treatment with such chemotherapeutic agent(s).

In other embodiments, the present invention relates to the use of a pharmaceutical combination comprising a compound represented by the structure of formula (III) or (IV) and at least one chemotherapeutic agent, e.g., Gemcitabine, 5-FU, Irinotecan, Oxaliplatin and any combination thereof, for the preparation of a medicament for the treatment of a tumor that is resistant to said chemotherapeutic agent(s), or for preventing acquired resistance to said chemotherapeutic agent(s), or for of preventing or delaying tumor recurrence following cease of treatment with such chemotherapeutic agent(s).

It is apparent to a person of skill in the art that other chemotherapeutic agents related to the above non-limiting examples can be used in the combinations of the present invention. For example, the present invention contemplates the use of other platinum compounds (e.g., carboplatin and cisplatin), SN-38 (a metabolite of Irinotecan) and other fluoropyrimidines (analogs of 5-FU).

In one embodiment, the compound is a compound of formula A. In another embodiment, the compound is a compound of formula B. In another embodiment, the compound is a compound of formula C. In another embodiment, the compound is a compound of formula D. In another embodiment, the compound is a compound of formula E. In another embodiment, the compound is a compound of formula F. In another embodiment, the compound is a compound of formula Ga. In another embodiment, the compound is a compound of formula H. In another embodiment, the compound is a compound of formula I. In another embodiment, the compound is a compound of formula J. In another embodiment, the compound is a compound of formula IV-4. In one currently preferred embodiment, the compound is represented by the structure of formula D. However, it is apparent to one of skill in the art that any of the compounds described herein may be used in the combinations of the present invention.

Treatment of Cancer

The term "cancer" as used herein refers to a disorder in which a population of cells has become, in varying degrees, unresponsive to the control mechanisms that normally govern proliferation and differentiation. Cancer refers to various types of malignant neoplasms and tumors, including primary tumors, and tumor metastasis. Non-limiting examples of cancers which can be treated by the combinations of the present invention are brain, ovarian, colon, prostate, kidney, bladder, breast, lung, oral, and skin cancers. Specific examples of cancers are: carcinomas, sarcomas, myelomas, leukemias, lymphomas and mixed type tumors. Particular categories of tumors include lymphoproliferative disorders, breast cancer, ovarian cancer, prostate cancer, cervical cancer, endometrial cancer, bone cancer, liver cancer, stomach cancer, colon cancer, pancreatic cancer, cancer of the thyroid, head and neck cancer, cancer of the central nervous system, cancer of the peripheral nervous system, skin cancer, kidney cancer, as well as metastases of all the above. Particular types of tumors include hepatocellular carcinoma, hepatoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, Ewing's tumor, leimyosarcoma, rhabdotheliosarcoma, invasive ductal carcinoma, papillary adenocarcinoma, melanoma, squamous cell carcinoma, basal cell carcinoma, adenocarcinoma (well differentiated, moderately differentiated, poorly differentiated or undifferentiated), renal cell carcinoma, hypernephroma, hypernephroid adenocarcinoma, bile duct carcinoma, choriocarcinoma, seminoma, embryonal carcinoma, Wilms' tumor, testicular tumor, lung carcinoma including small cell, non-small and large cell lung carcinoma, bladder carcinoma, glioma, astrocyoma, medulloblastoma, craniopharyngioma, ependymoma, pinealoma, retinoblastoma, neuroblastoma, colon carcinoma, rectal carcinoma, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma, and hepatocarcinoma. Each possibility represents a separate embodiment of the present invention.

In some representative embodiments, the cancer is selected from the group consisting of head and neck (H&N) cancer, sarcoma, multiple myeloma, ovarian cancer, breast cancer, kidney cancer, stomach cancer, hematopoietic cancers, lymphoma, leukemia, including lymphoblastic leukemia, lung carcinoma, melanoma, glioblastoma, hepatocarcinoma, prostate cancer and colon cancer. Each possibility represents a separate embodiment of the present invention.

The term "treatment of cancer" in the context of the present invention includes at least one of the following: a decrease in the rate of growth of the cancer (i.e. the cancer still grows but at a slower rate); cessation of growth of the cancerous growth, i.e., stasis of the tumor growth, and, in preferred cases, the tumor diminishes or is reduced in size. The term also includes reduction in the number of metastases, reduction in the number of new metastases formed, slowing of the progression of cancer from one stage to the other and a decrease in the angiogenesis induced by the cancer. In most preferred cases, the tumor is totally eliminated. Additionally included in this term is lengthening of the survival period of the subject undergoing treatment, lengthening the time of diseases progression, tumor regression, and the like. It is to be understood that the term "treating cancer" also refers to the inhibition of a malignant (cancer) cell proliferation including tumor formation, primary tumors, tumor progression or tumor metastasis. The term "inhibition of proliferation" in relation to cancer cells, may further refer to a decrease in at least one of the following: number of cells (due to cell death which may be necrotic, apoptotic or any other type of cell death or combinations thereof) as compared to control; decrease in growth rates of cells, i.e. the total number of cells may increase but at a lower level or at a lower rate than the increase in control; decrease in the invasiveness of cells (as determined for example by soft agar assay) as compared to control even if their total number has not changed; progression from a less differentiated cell type to a more differentiated cell type; a deceleration in the neoplastic transformation; or alternatively the slowing of the progression of the cancer cells from one stage to the next.

As used herein, the term "administering" refers to bringing in contact with the combination of the present invention. Administration can be accomplished to cells or tissue cultures, or to living organisms, for example humans. In one embodiment, the present invention encompasses administering the combinations of the present invention to a human subject.

A "therapeutic" treatment is a treatment administered to a subject who exhibits signs of pathology for the purpose of diminishing or eliminating those signs. A "therapeutically effective amount" is that amount of compound or a composition which is sufficient to provide a beneficial effect to the subject to which the compound or composition is administered.

The term "following cease of treatment" as used herein means after treatment with the drug of choice is stopped. For example, according to certain embodiments of the present invention, the IRS/Stat3 Dual Modulator (e.g., compound of formula (III) or (IV)) is administered together (sequentially or concurrently) with any of the combination treatments described herein, for a desired duration of time. Then, treatment (with all compounds) is stopped and the tumors are monitored for a desired period of time. As contemplated herein, the IRS/Stat3 Dual Modulators of the present invention are able to prevent or delay tumor recurrence following cease of treatment with the any of the combination drugs described herein, to a greater extent than any of these drugs administered alone.

The term "treating a tumor that has developed resistance" to a certain anti-cancer drug, or "preventing acquired resistance of a tumor" to a certain anti-cancer drug, means any one or more of the following: (i) the tumors acquire or develop resistance as a result of treatment to that anti-cancer drug; (ii) that the tumors acquire or develop resistance as a result of treatment with other anti-cancer drugs; or (iii) the tumors have a primary resistance to that anti-cancer drug.

The combination therapy can provide a therapeutic advantage in view of the differential toxicity associated with the two individual treatments. For example, treatment with one compound can lead to a particular toxicity that is not seen with the other compound, and vice versa. As such, this differential toxicity can permit each treatment to be administered at a dose at which the toxicities do not exist or are minimal, such that together the combination therapy provides a therapeutic dose while avoiding the toxicities of each of the constituents of the combination agents. Furthermore, when the therapeutic effects achieved as a result of the combination treatment are enhanced or synergistic, i.e., significantly better than additive therapeutic effects, the doses of each of the agents can be reduced even further, thus lowering the associated toxicities to an even greater extent.

The terms "synergistic", "cooperative" and "super-additive" and their various grammatical variations are used interchangeably herein. An interaction between an IRS/Stat3 dual modulator and another anti-cancer agent (e.g., mTOR inhibitor, EGFR inhibitor, EGFR antibody and/or immunotherapy agent) is considered to be synergistic, cooperative or super-additive when the observed effect (e.g., cytotoxicity) in the presence of the drugs together is higher than the sum of the individual effects of each drug administered separately. In one embodiment, the observed combined effect of the drugs is significantly higher than the sum of the individual effects. The term significant means that the observed $p<0.05$. A non-limiting manner of calculating the effectiveness of the combined treatment comprises the use of the Bliss additivism model (Cardone et al. *Science* (1998), 282: 1318-1321) using the following formula: $E_{bliss}=E_A+E_B-E_A \times E_B$, where $E_A$ and $E_B$ are the fractional inhibitions obtained by drug A alone and drug B alone at specific concentrations. When the experimentally measured fractional inhibition is equal to Ebliss, the combination provides an additive therapeutic effect. When the experimentally measured fractional inhibition is greater than Ebliss, the combination provides a synergistic therapeutic effect.

Pharmaceutical Compositions

Although the components of the combinations of the present invention can be administered alone, it is contemplated that the components are administered in pharmaceutical compositions further containing at least one pharmaceutically acceptable carrier or excipient. Each of the components can be administered in a separate pharmaceutical composition, or the combination can be administered in one pharmaceutical composition.

The pharmaceutical compositions of the present invention can be formulated for administration by a variety of routes including oral, rectal, transdermal, parenteral (subcutaneous, intraperitoneal, intravenous, intra-arterial, transdermal and intramuscular), topical, intranasal, or via a suppository. Each possibility represents a separate embodiment of the present invention. Such compositions are prepared in a manner well known in the pharmaceutical art and comprise as an active ingredient at least one compound of the present invention as described hereinabove, and a pharmaceutically acceptable excipient or a carrier. The term "pharmaceutically acceptable" means approved by a regulatory agency of the Federal or a state government or listed in the U.S. Pharmacopeia or other generally recognized pharmacopeia for use in animals and, more particularly, in humans.

During the preparation of the pharmaceutical compositions according to the present invention the active ingredient is usually mixed with a carrier or excipient, which may be a solid, semi-solid, or liquid material. The compositions can be in the form of tablets, pills, capsules, pellets, granules, powders, lozenges, sachets, cachets, elixirs, suspensions, dispersions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. Each possibility represents a separate embodiment of the present invention.

The carriers may be any of those conventionally used and are limited only by chemical-physical considerations, such as solubility and lack of reactivity with the compound of the invention, and by the route of administration. The choice of carrier will be determined by the particular method used to administer the pharmaceutical composition. Some examples of suitable carriers include lactose, glucose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water and methylcellulose. Each possibility represents a separate embodiment of the present invention. The formulations can additionally include lubricating agents such as talc, magnesium stearate, and mineral oil; wetting agents, surfactants, emulsifying and suspending agents; preserving agents such as methyl- and propylhydroxybenzoates; sweetening agents; flavoring agents, colorants, buffering agents (e.g., acetates, citrates or phosphates), disintegrating agents, moistening agents, anti-bacterial agents, anti-oxidants (e.g., ascorbic acid or sodium bisulfite), chelating agents (e.g., ethylenediaminetetraacetic acid), and agents for the adjustment of tonicity such as sodium chloride. Other pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerin, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions. Each possibility represents a separate embodiment of the present invention.

For preparing solid compositions such as tablets, the principal active ingredient(s) is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing, for example, from about 0.1 mg to about 2000 mg, from about 0.1 mg to about 500 mg, from about 1 mg to about 100 mg, from about 100 mg to about 250 mg, etc. of the active ingredient(s) of the present invention.

Any method can be used to prepare the pharmaceutical compositions. Solid dosage forms can be prepared by wet granulation, dry granulation, direct compression and the like. The solid dosage forms of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer, which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate. Each possibility represents a separate embodiment of the present invention.

The liquid forms in which the compositions of the present invention may be incorporated, for administration orally or by injection, include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles. Each possibility represents a separate embodiment of the present invention.

Compositions for inhalation or insulation include solutions and suspensions in pharmaceutically acceptable aqueous or organic solvents, or mixtures thereof, and powders. The liquid or solid compositions may contain suitable pharmaceutically acceptable excipients as described above. In one embodiment, the compositions are administered by the oral or nasal respiratory route for local or systemic effect. Compositions in pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, orally or nasally, from devices that deliver the formulation in an appropriate manner Another formulation suitable for the compositions and methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art.

In yet another embodiment, the composition is prepared for topical administration, e.g. as an ointment, a gel a drop or a cream. For topical administration to body surfaces using, for example, creams, gels, drops, ointments and the like, the compounds of the present invention can be prepared and applied in a physiologically acceptable diluent with or without a pharmaceutical carrier. The present invention may be used topically or transdermally to treat cancer, for example, melanoma. Adjuvants for topical or gel base forms may include, for example, sodium carboxymethylcellulose, polyacrylates, polyoxyethylene-polyoxypropylene-block polymers, polyethylene glycol and wood wax alcohols. Each possibility represents a separate embodiment of the present invention.

Alternative formulations include nasal sprays, liposomal formulations, slow-release formulations, pumps delivering the drugs into the body (including mechanical or osmotic pumps) controlled-release formulations and the like, as are known in the art.

The compositions are preferably formulated in a unit dosage form. The term "unit dosage forms" refers to physically discrete units suitable as unitary dosages for human subjects and other mammals, each unit containing a predetermined quantity of active material(s) calculated to produce the desired therapeutic effect, in association with a suitable pharmaceutical excipient.

In preparing a formulation, it may be necessary to mill the active ingredient to provide the appropriate particle size prior to combining with the other ingredients. If the active compound is substantially insoluble, it ordinarily is milled to a particle size of less than 200 mesh. If the active ingredient is substantially water soluble, the particle size is normally adjusted by milling to provide a substantially uniform distribution in the formulation, e.g. about 40 mesh.

It may be desirable to administer the pharmaceutical composition of the invention locally to the area in need of treatment; this may be achieved by, for example, and not by way of limitation, local infusion during surgery, infusion to the liver via feeding blood vessels with or without surgery, topical application, e.g., in conjunction with a wound dressing after surgery, by injection, by means of a catheter, by means of a suppository, or by means of an implant, the implant being of a porous, non-porous, or gelatinous material. According to some embodiments, administration can be by direct injection e.g., via a syringe, at the site of a tumor or neoplastic or pre-neoplastic tissue.

The compounds may also be administered by any convenient route, for example by infusion or bolus injection, by absorption through epithelial linings (e.g., oral mucosa, rectal and intestinal mucosa, etc.), and may be administered together with other therapeutically active agents. The administration may be localized or it may be systemic. In addition, it may be desirable to introduce the pharmaceutical compositions of the invention into the central nervous system by any suitable route, including intra-ventricular and intrathecal injection; intra-ventricular injection may be facilitated by an intra-ventricular catheter, for example, attached to a reservoir. Pulmonary administration can also be employed, e.g., by use of an inhaler or nebulizer, and formulation with an aerosolizing agent.

A compound of the present invention can be delivered in an immediate release or in a controlled release system. In one embodiment, an infusion pump may be used to administer a compound of the invention, such as one that is used for delivering chemotherapy to specific organs or tumors (see Buchwald et al., 1980, Surgery 88: 507; Saudek et al., 1989, N. Engl. J. Med. 321: 574). In one embodiment, a compound of the invention is administered in combination with a biodegradable, biocompatible polymeric implant, which releases the compound over a controlled period of time at a selected site. Examples of polymeric materials include, but are not limited to, polyanhydrides, polyorthoesters, polyglycolic acid, polylactic acid, polyethylene vinyl acetate, copolymers and blends thereof. In yet another embodiment, a controlled release system can be placed in proximity of the therapeutic target, thus requiring only a fraction of the systemic dose.

Furthermore, at times, the pharmaceutical compositions may be formulated for parenteral administration (subcutaneous, intravenous, intra-arterial, transdermal, intraperitoneal or intramuscular injection) and may include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that include suspending agents, solubilizers, thickening agents, stabilizers, and preservatives. Oils such as petroleum, animal, vegetable, or synthetic oils and soaps such as fatty alkali metal, ammonium, and triethanolamine salts, and suitable detergents may also be used for parenteral administration. The above formulations may also be used for direct intra-tumoral injection. Further, in order to minimize or eliminate irritation at the site of injection, the compositions may contain one or more nonionic surfactants. Suitable surfactants include polyethylene sorbitan fatty acid esters, such as sorbitan monooleate and the high molecular weight adducts of ethylene oxide with a hydrophobic base, formed by the condensation of propylene oxide with propylene glycol.

The parenteral formulations can be presented in unit-dose or multi-dose sealed containers, such as ampoules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described and known in the art. Each possibility represents a separate embodiment of the present invention.

Alternatively, the combinations of the present invention can be used in hemodialysis such as leukophoresis and other related methods, e.g., blood is drawn from the patient by a variety of methods such as dialysis through a column/hollow fiber membrane, cartridge etc., is treated with the IRS/Stat3 dual modulator and/or additional anti-cancer agent ex-vivo, and returned to the patient following treatment. Such treatment methods are well known and described in the art. See, e.g., Kolho et al. (J. Med. Virol. 1993, 40(4):318-21); Ting et al. (Transplantation, 1978, 25(1):31-3); the contents of which are hereby incorporated by reference in their entirety.

Doses and Dosing Schedules

The treatment with the IRS/Stat3 dual modulator and the other anti-cancer agent (i.e., EGFR inhibitor/EGFR antibody/mTOR inhibitor/immunotherapy agent/MEK inhibitor/mutated B-Raf inhibitor/chemotherapeutic agent or combination thereof) can take place sequentially in any order, simultaneously or a combination thereof. For example, administration of an IRS/Stat3 dual modulator can take place prior to, after or at the same time as administration of the other anti-cancer agent or combination thereof. For example, a total treatment period can be decided for the IRS/Stat3 dual modulator. The other anti-cancer agent can be administered prior to onset of treatment with the IRS/Stat3 dual modulator or following treatment with the IRS/Stat3 dual modulator. In addition, the other anti-cancer agent can be administered during the period of IRS/Stat3 dual modulator administration but does not need to occur over the entire treatment period. In another embodiment, the treatment regimen includes pre-treatment with one agent, either the IRS/Stat3 dual modulator or the EGFR inhibitor/EGFR antibody/mTOR inhibitor/immunotherapy agent/MEK inhibitor/mutated B-Raf inhibitor/chemotherapeutic agent or combination thereof followed by the addition of the other agent or agents. Alternating sequences of administration are also contemplated. Alternating administration includes administration of an IRS/Stat3 dual modulator and other anti-cancer agent in alternating sequences, e.g., IRS/Stat3 dual modulator, followed by the other anti-cancer agent, followed by IRS/Stat3 dual modulator, etc.

The amount of a compound that will be effective in the treatment of a particular disorder or condition, including cancer, will depend on the nature of the disorder or condition, and can be determined by standard clinical techniques. In addition, in vitro assays may optionally be employed to help identify optimal dosage ranges. The precise dose to be employed in the formulation will also depend on the route of administration, and the progression of the disease or disorder, and should be decided according to the judgment of the practitioner and each patient's circumstances. A preferred dosage will be within the range of 0.01-1000 mg/kg of body weight, 0.1 mg/kg to 100 mg/kg, 1 mg/kg to 100 mg/kg, 10 mg/kg to 75 mg/kg, 0.1-1 mg/kg, etc. Exemplary (non-limiting) amounts of the IRS/Stat3 dual modulator EGFR inhibitor/EGFR antibody/mTOR inhibitor/immunotherapy agent/MEK inhibitor/mutated B-Raf inhibitor/chemotherapeutic agent include 0.1 mg/kg, 0.2 mg/kg, 0.5 mg/kg, 1 mg/kg, 5 mg/kg, 10 mg/kg, 20 mg/kg, 50 mg/kg, 60 mg/kg, 75 mg/kg and 100 mg/kg. Alternatively, the amount administered can be measured and expressed as molarity of the administered compound. By way of illustration and not limitation, an IRS/Stat3 dual modulator (e.g. a compound of any of formulae I, II, III, IV) can be administered in a range of 0.1-10 mM, e.g., 0.1, 0.25, 0.5, 1 and 2 mM. Alternatively, the amount administered can be measured and expressed as mg/ml, μg/ml, or ng/ml. By way of illustration and not limitation, the EGFR inhibitor/EGFR antibody/mTOR inhibitor/immunotherapy agent/MEK inhibitor/mutated B-Raf inhibitor/chemotherapeutic agent can be administered in an amount of 1 ng/ml to 100 mg/ml, for example 1-1000 ng/ml, 1-100 ng/ml, 1-1000 μg/ml, 1-100 μg/ml, 1-1000 mg/ml, 1-100 mg/ml, etc. Effective doses may be extrapolated from dose-response curves derived from in vitro or animal model test bioassays or systems. When a synergistic effect is observed, the overall dose of each of the components may be lower, thus the side effects experienced by the subject may be significantly lower, while a sufficient anti-cancer effect is nevertheless achieved.

In one embodiment, the combination therapy reduces the amount of each of its component by a factor of 2, i.e., each component is given at half the dose as compared with single agent therapy, and still achieves the same or similar therapeutic effect. In another embodiment, the combination therapy reduces the amount of each of its component by a factor of 5, 10, 20, 50 or 100. As demonstrated herein, the IC$_{50}$ of chemotherapeutic agents as anti-proliferative agents in various cancer cells are reduced as compared to the IC$_{50}$ of the chemotherapeutic agent, when administered alone.

The administration schedule will depend on several factors such as the cancer being treated, the severity and progression, the patient population, age, weight etc. For example, the compositions of the invention can be taken once-daily, twice-daily, thrice daily, once-weekly or once-monthly. In addition, the administration can be continuous, i.e., every day, or intermittently. The terms "intermittent" or "intermittently" as used herein means stopping and starting at either regular or irregular intervals. For example, intermittent administration can be administration one to six days per week or it may mean administration in cycles (e.g. daily administration for two to eight consecutive weeks, then a rest period with no administration for up to one week) or it may mean administration on alternate days. The different components of the combination can, independently of the other, follow different dosing schedules.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXPERIMENTAL DETAILS SECTION

Example 1: Prevention of Acquired Resistance to Erlotinib with Compound D

Experimental system: Patient-derived xenograft (PDX) of Squamous Cell carcinoma of Head&Neck (SCCHN) tumor biopsy subcutaneous implanted into NodScid mice.

I. Animals and Biopsy

Biopsy: Fresh human primary SCCHN tumor biopsy.
Tumor Type: Salivary gland mucoepidermoid carcinoma.
Genomic analysis revealed amplified and mutated (activated) EGFR.
Implantation of tumor biopsy grafts (P0): Fresh human primary SCCHN tumor biopsy grafts were sub-cutaneously (SC) implanted into 5 female NOD.CB17-Prkdc$^{scid}$/J (NodScid mice), 5-6 weeks old (Harlan, IL), following 14 days of acclimation.
Implantation of tumor biopsy grafts (P1) into NodScid mice for efficacy study: 3.5 weeks following implantation of the biopsy (P0), tumors reached average size of about 1,200 mm$^3$, the mice were sacrificed by cervical dislocation and the tumors were excised. The tumors were measured, cut into small pieces of 2-4 mm and transferred into a gentleMACS Tube containing sterile saline. Tumor volume was adjusted with saline to get 1.5 mm$^3$ tumor volume/100 μl saline. The sample was dissociated using a gentleMACS Octo Dissociator. The dissociated tumor tissue was collected with 18G syringe and injected directly under the skin. 35 female NodScid mice 4-5 weeks old (Harlan, IL) were injected each subcutaneously into the nape area with 100 μl of the obtained cell solution (approximately 1.5 mm$^3$ tumor volume P1 in 100 μl saline per mouse) Animals were observed and monitored for any discomfort and immobility day by day, checked for inability to move or feed properly, being hunched and inactive, and ulcerations, defined as exposing of necrotic centers.
Onset of tumor growth (palpable tumor mass) was detected ten days following cell injection. After 8 days, 32 out of 35 injected mice developed tumors with an average size of about 80 mm$^3$. The mice were randomly divided into 4 treatment groups including 8 animals/group.

II. Treatments and Procedures

When tumor size was ~80 mm$^3$ (day0) the following treatments initiated:
1. Control (vehicle): Water 100 μl PO (5 times/week, daily)
2. Compound D 70 mg/kg in 20% 2-Hydroxypropyl-β-cyclodextrin (HPbCD), IV (3 times/week, qod)
3. Erlotinib 100 mg/kg PO (5 times/week, daily).
4. Erlotinib 100 mg/kg PO (5 times/week)+Compound D 70 mg/kg IV (3 times/week). Erlotinib was administered ~4 hr following Compound D, when administered on the same days.

All treatments for each of the treatment groups 1-4 were initiated simultaneously.

The length (l) and the width (w) of the tumors were measured 4 times a week and the volumes of the tumors were calculated as follows: v=lw$^2$/2. Graphs represent average tumor volumes with standard errors (standard deviations/square root of group size). Mice weight and behavior were examined at least once a week. After two weeks of treatment mice were sacrificed and the tumors were excised for biochemical and genomic analysis 14 hrs following last administration of drug/inhibitor. Three mice in the combined treatment group were not sacrificed at the end of treatment and were kept with no further treatment.

Results

As shown in FIG. 1, treatment with Erlotinib, an EGFR TK inhibitor, initially led to a significant tumor regression in all the treated mice (FIG. 1, open squares). However, after one week of treatment all the tumors developed resistance to Erlotinib and progressed aggressively. Combined treatment with Erlotinib and Compound D led to significant tumor regression in all the treated mice and none of the tumors regrew during the period of combined treatment (FIG. 1, open circles).

Two mice that achieved complete response were kept alive with no further treatment and remained free of disease after 3 months with no further treatment.

Although the initial tumor has not responded to Compound D alone, the acquired resistance to Erlotinib was completely abolished by Compound D. Evidence from the literature suggests that treatment with Erlotinib induces IRS up-regulation leading to resistance by the activation of IGF1R/IRS-to-AKT survival pathway. Other reports claim that Stat3 phosphorylation is induced by Erlotinib in H&N cancer, and the inhibition of Stat3 & EGFR has synergic inhibitory effect on H&N tumors. Without wishing to be bound by any particular theory or mechanism of action, Compound D and other compounds of formulae (I-IV) described herein are dual inhibitors of IRS1/2 and Stat3 and, therefore, should antagonize these Erlotinib-induced mechanisms and prevent resistance.

Example 2: Regression of Erlotinib-Resistant Tumors with Combined Treatment of Erlotinib and Compound D Experimental system: Patient-derived xenograft (PDX) of Squamous Cell carcinoma of Head&Neck (SCCHN) tumor biopsy subcutaneous implanted into NodScid mice.

I. Animals and Biopsy
  Implantation of SCCHN tumor biopsy graft (P8) into NodScid mice for efficacy study: Five months following implantation of SCCHN tumor biopsy graft (P1) described above, tumor cells (P8) were injected into NodScid mice from self-breeding, 9.5 weeks old, using the same procedure described for implantation of P1. The original biopsy is the same as described above and the P indicates passages (implantation number in mice).
  Onset of tumor growth (palpable tumor mass) was detected seven days following cell injection. 12 days later, mice which developed tumors sized around 70 mm$^3$. The mice were randomly divided into 4 treatment groups including 4 animals in the groups treated with Vehicle, Compound D or Compound D+ Erlotinib, and the rest treated with Erlotinib. Treatments initiated simultaneously (day 0).

Figure 2:
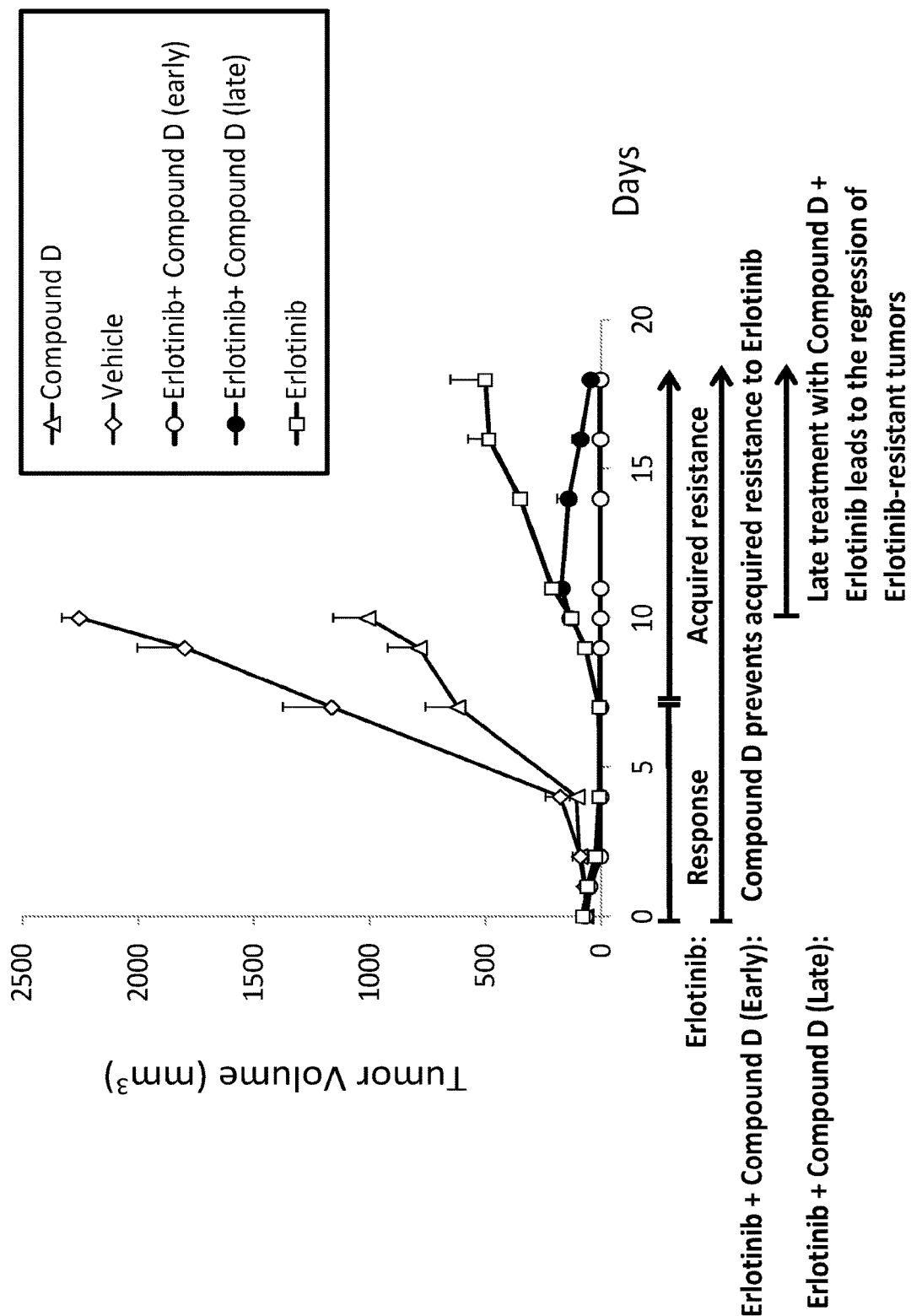
FIG. 2. Compound D prevents acquired resistance to Erlotinib and leads to regression of Erlotinib-resistant tumors in mice implanted with a tumor from a Head & Neck (H&N) cancer patient. Mice were treated with (a) vehicle (◇); (b) Erlotinib (□); (c) Compound D (Δ); or (d) Erlotinib+Compound D (○). Treatment with Erlotinib (group b) initially led to tumor regression. While on treatment, the tumors developed resistance to Erlotinib and regrew. Combined treatment of Erlotinib and Compound D induced tumor regression and none of the tumors regrew (group d), consistent with the results displayed in FIG. 1. Following resistance to Erlotinib has been acquired, the mice in group b whose tumors were ~130 mm$^3$ on day 10 were divided into two groups, the first remained on Erlotinib alone (□) and the second received a combined treatment of Erlotinib+Compound D starting on day 10 of treatment (●). While tumors significantly grew under treatment with Erlotinib alone (□), the combined treatment of Compound D and Erlotinib induced tumor regression (●).

II. Treatments and Procedures
  Treatment groups included:
  1. Vehicle-control: 20% 2-Hydroxypropyl-β-cyclodextrin (HPbCD) 50 µl/injection, IV (3 times/week, qod).
  2. Compound D 70 mg/kg in HPbCD, IV (3 times/week, qod).
  3. Erlotinib 100 mg/kg in HPbCD, PO (5 times/week).
  4. Erlotinib 100 mg/kg PO (5 times/week)+Compound D 70 mg/kg IV (3 times/week). Erlotinib was administered ~4 hr following Compound D, when administered at the same days.
  All these treatments were initiated simultaneously.
  Treatment with Erlotinib (Group 3) led to a dramatic tumor regression (FIG. 2, open squares). While on treatment, tumors developed resistance to Erlotinib after 1 week of treatment and aggressively progressed. Erlotinib-treated mice, which developed tumors around 130 mm$^3$ on day10 (n=7), were split to two groups:
  5. The first (n=3) continued to get Erlotinib (100 mg/kg PO, 5 times/week), and
  6. The second group (n=4) started a combined treatment with Erlotinib (100 mg/kg PO, 5 times/week)+Compound D (70 mg/kg IV, 3 times/week, qod) on day10 of treatment. Erlotinib was administered ~4 hr following Compound D, when administered at the same days.

The length (l) and the width (w) of the tumors were measured 4 times a week and the volumes of the tumors were calculated as follows: $v=lw^2/2$. Graphs represent average tumor volumes with standard errors (standard deviations/square root of group size). Mice weight and behavior were examined at least once a week. Mice were sacrificed and the tumors were excised for biochemical and genomic analysis.

Results

As shown in FIG. 2, treatment with Erlotinib (open square) led to tumor regression in 78% of treated mice (14 out of 18 mice responded). However while on treatment, tumors developed resistance to Erlotinib after 1 week and aggressively progressed. Erlotinib-treated mice whose tumors were ~130 mm$^3$ on day 10 (n=7) were split to two groups—the first (n=3) continued to get Erlotinib (open squares), and the second group (n=4) started a combined treatment with Erlotinib+Compound D (black circles) on day10 of treatment. Dramatic tumor regression was observed following initiation of the combined treatment (FIG. 2, late treatment, black circles) while tumors of mice treated with Erlotinib only, aggressively developed (FIG. 2, open squares). Combined treatment with Erlotinib+Compound D initiated on day 0 (FIG. 2, early treatment, open circles) led to a significant tumor regression in all treated mice and no tumors regrew, consistent with the results of Example 1.

Conclusion

In conclusion, combined treatment of Compound D+Erlotinib is highly effective and leads to a dramatic regression of tumors following resistance to Erlotinib has already acquired. Furthermore, in early treatment of established tumors Compound D prevents acquired resistance to Erlotinib.

Example 3: Compound D Prevents Acquired Resistance to Erlotinib Even when Initial Tumor Size is Very High (700 mm$^3$)

Experimental system: Patient-derived xenograft (PDX) of Squamous Cell carcinoma of SCCHN tumor biopsy subcutaneous implanted into NRG mice.

I. Animals and Biopsy
  Implantation of SCCHN tumor biopsy graft (P11) into NRG mice for efficacy study: Eight months following implantation of SCCHN tumor biopsy graft (P1) described above, tumor cells (P11) were injected into 20 male mice NOD.Cg-Rag1tm1Mom Il2rgtm1Wj1/SzJ mice (Common name: NRG), from self-breeding, using the same procedure described for implantation of P1. The original biopsy is the same as described above and the P indicates passages (implantation number in mice).
  Onset of tumor growth (palpable tumor mass) was detected six days following cell injection. 13 days later, 19 out of 20 injected mice developed tumors with an average size of 700-720 mm$^3$ (day0). The mice were randomly divided into 4 treatment groups including 4 animals in the group treated with Vehicle, and 5 mice/group in the groups treated with Erlotinib, Compound D or Compound D+Erlotinib. All treatments initiated simultaneously on day 0.

II. Treatments and Procedures
  Treatment groups included:
  1. Vehicle-control: 20% HPbCD 50 µl/injection, IV (3 times/week, qod), 4 mice.
  2. Compound D 70 mg/kg in HPbCD, IV (3 times/week, qod), 5 mice.
  3. Erlotinib 100 mg/kg in HPbCD, PO (5 times/week), 5 mice.
  4. Erlotinib 100 mg/kg PO (5 times/week)+Compound D 70 mg/kg IV (3 times/week), 5 mice. Erlotinib was administered ~4 hr following Compound D, when administered at the same days.

The length (l) and the width (w) of the tumors were measured 4 times a week and the volumes of the tumors were calculated as follows: $v=lw^2/2$. Graphs represent average tumor volumes with standard errors (standard deviations/square root of group size). Mice weight and behavior were examined routinely. Mice were sacrificed and the tumors were excised for biochemical and genomic analysis.

Results

Figure 3:
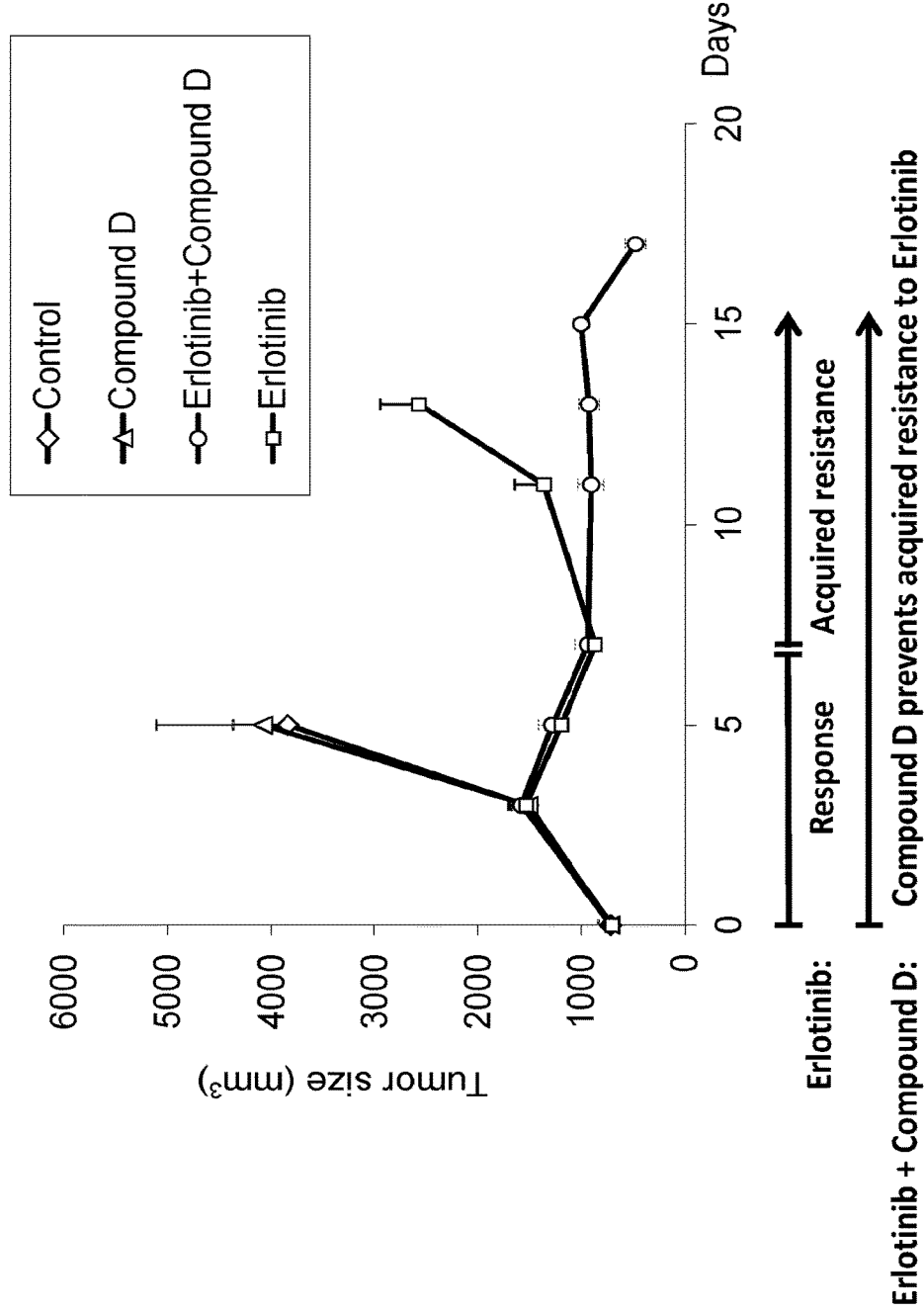
FIG. 3. Compound D prevents acquired resistance to Erlotinib in large tumors (700 mm$^3$). Mice were treated with vehicle (◇), Erlotinib (□), Compound D (Δ), or Erlotinib+Compound D (○). Treatments were initiated when average tumor size was ~700 mm$^3$.

As shown in FIG. 3, treatment with Erlotinib led to a significant response of the tumors, their growth was halted and they regressed. However while on treatment, tumors developed resistance to Erlotinib a week following treatment initiation and aggressively progressed (FIG. 3, open squares). Combined treatment with Erlotinib+Compound D initiated on day 0 (FIG. 3, open circles) showed the same response as to Erlotinib in the first week but the combined treatment with Compound D prevented acquired resistance to Erlotinib, prevented regrowth of tumors and induced tumor regression, consistent with the results of Example 1.

Conclusion

In conclusion, combined treatment of Compound D+Erlotinib is highly effective and prevents acquired resistance to Erlotinib, even if the initial size of the tumors was very high (700 mm$^3$) when treatments initiated.

Example 4: Combined Treatment of Compound D and Afinitor Efficiently Blocks the Growth of Sarcoma Patient-Derived Xenografts in Mice Experimental system: Patient-derived xenograft (PDX) of Uteral AdenoSarcoma biopsy subcutaneous implanted into NodScid mice.
I. Animals and Biopsy
  Biopsy: Frozen human primary Uteral AdenoSarcoma (sample ID: OT_001)
  Implantation of tumor biopsy grafts (P0): Frozen human primary Uteral AdenoSarcoma biopsy grafts were subcutaneous (SC) implanted (P0) into female NOD.CB17-Prkdc$^{scid}$/J (NodScid mice, Harlan IL). Three months later the tumors were excised, cut into small pieces and implanted in 38 NodScid mice (P1) for efficacy study.
  Eight days following implantation of the biopsy (P1) tumor onset was detected in 37 mice.
  A week later (day0), tumors in 33 mice reached an average size of 130 mm$^3$ and the mice were randomly divided into 4 treatment groups.
II. Treatments and Procedures
  Treatment groups included:
    1. Control: 20% HPbCD 50 ul IP, qod (6 mice).
    2. Compound D 70 mg/kg in 20% HPbCD, IV, qod (6 mice).
    3. Afinitor 5 mg/kg PO, qod (15 mice).
    4. Afinitor 5 mg/kg PO (qod)+Compound D 70 mg/kg IV (qod), 6 mice. Afinitor was administered ~4 hr following Compound D.
  All treatments were initiated simultaneously on day0.
  The length (l) and the width (w) of the tumors were measured every other day and the volumes of the tumors were calculated as follows: $v=lw^2/2$. Graphs represent average tumor volumes with standard errors (standard deviations/square root of group size). Four days following initiation of treatment the tumors of the control group and the Compound D group already reached the end point and mice were sacrificed.

Results

Figure 4:
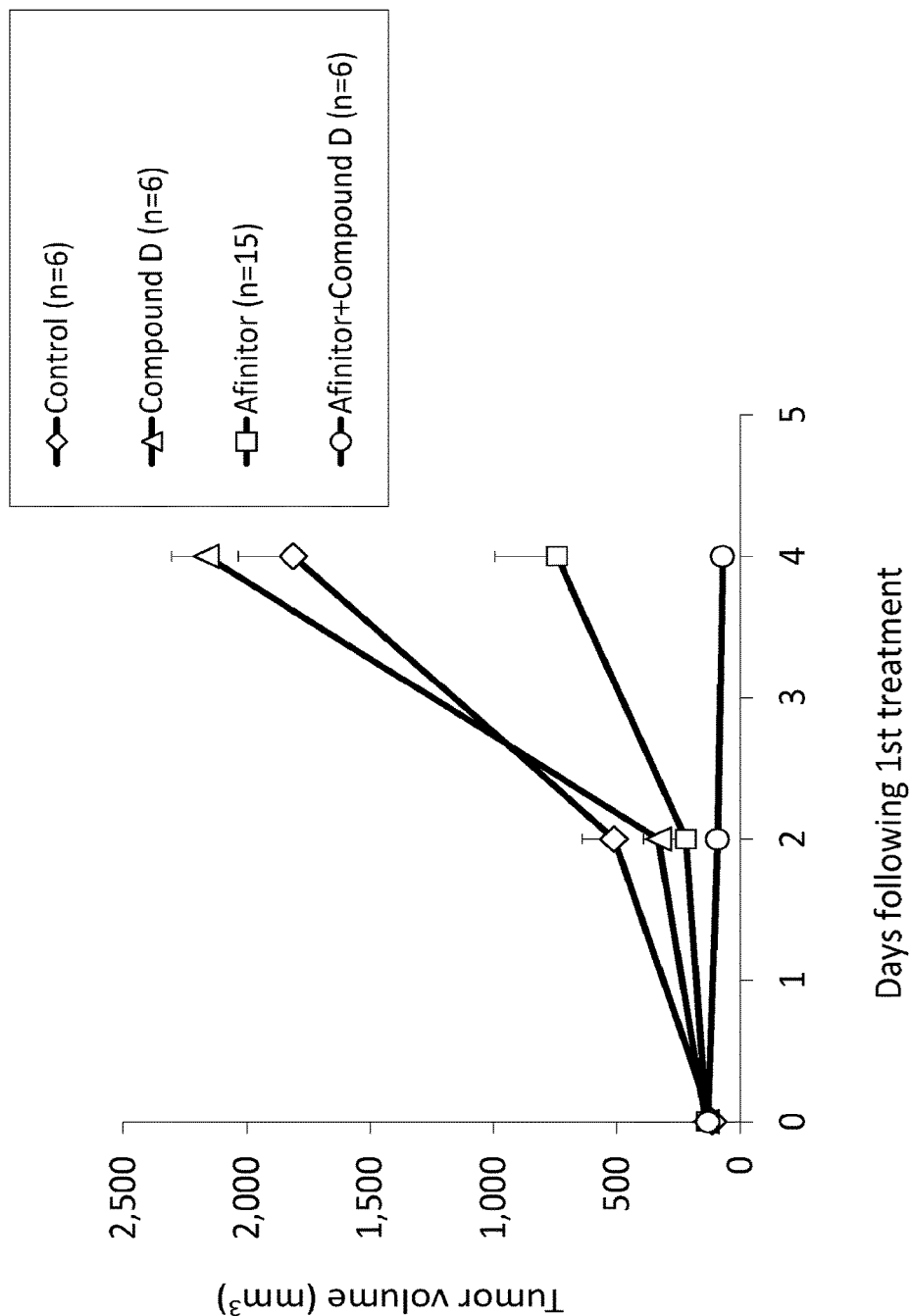
FIG. 4. Combined treatment with Afinitor and Compound D induces tumor regression of aggressive Uteral AdenoSarcoma in mice. Mice implanted with patient-derived xenografts of violent Uteral AdenoSarcoma were treated when average tumor size was ~130 mm$^3$ with either vehicle (◇), Afinitor (□), Compound D (Δ), or Afinitor+Compound D (○). The average tumor volume of the Afinitor-treated group (□) indicated tumor growth inhibition. While Compound D (Δ) alone had no significant effect on tumor growth as compared to the control, the combined treatment with Afinitor+Compound D (○) led to tumor regression. In alternative analysis of the results (demonstrated in FIG. 5)—while none of the mice responded to Compound D alone (Δ) and in the Afinitor-treated group (□) half of the group responded and the other half did not, the combined treatment with Afinitor+Compound D (○) led to positive response of all mice in the group.

As shown in FIG. 4, treatment with Afinitor (open squares), an mTOR/S6K inhibitor, led to growth inhibition of the tumors: while average tumor size in the control group increased 16-fold the average tumor size in the Afinitor group increased 5.5-fold.
Surprisingly, although Compound D alone (open triangles) had no significant effect on tumor growth, the combined treatment of Afinitor+Compound D (open circles) led to tumor regression. The average tumor size of the combined treatment regressed from 130 mm$^3$ to 70 mm$^3$ in four days and after only two treatments.
In terms of responders vs. non-responder mice, while no response to Compound D alone was detected, and only half of the mice in the Afinitor-treated group responded (group A, n=8) and half—not (group B, n=7), all the mice in the combined treatment responded and most tumors even significantly regressed.

Example 5: Compound D Prevents Acquired Resistance to Afinitor (A) and Leads to Regression of Afinitor-Resistant Tumors (B)

Figure 5A:
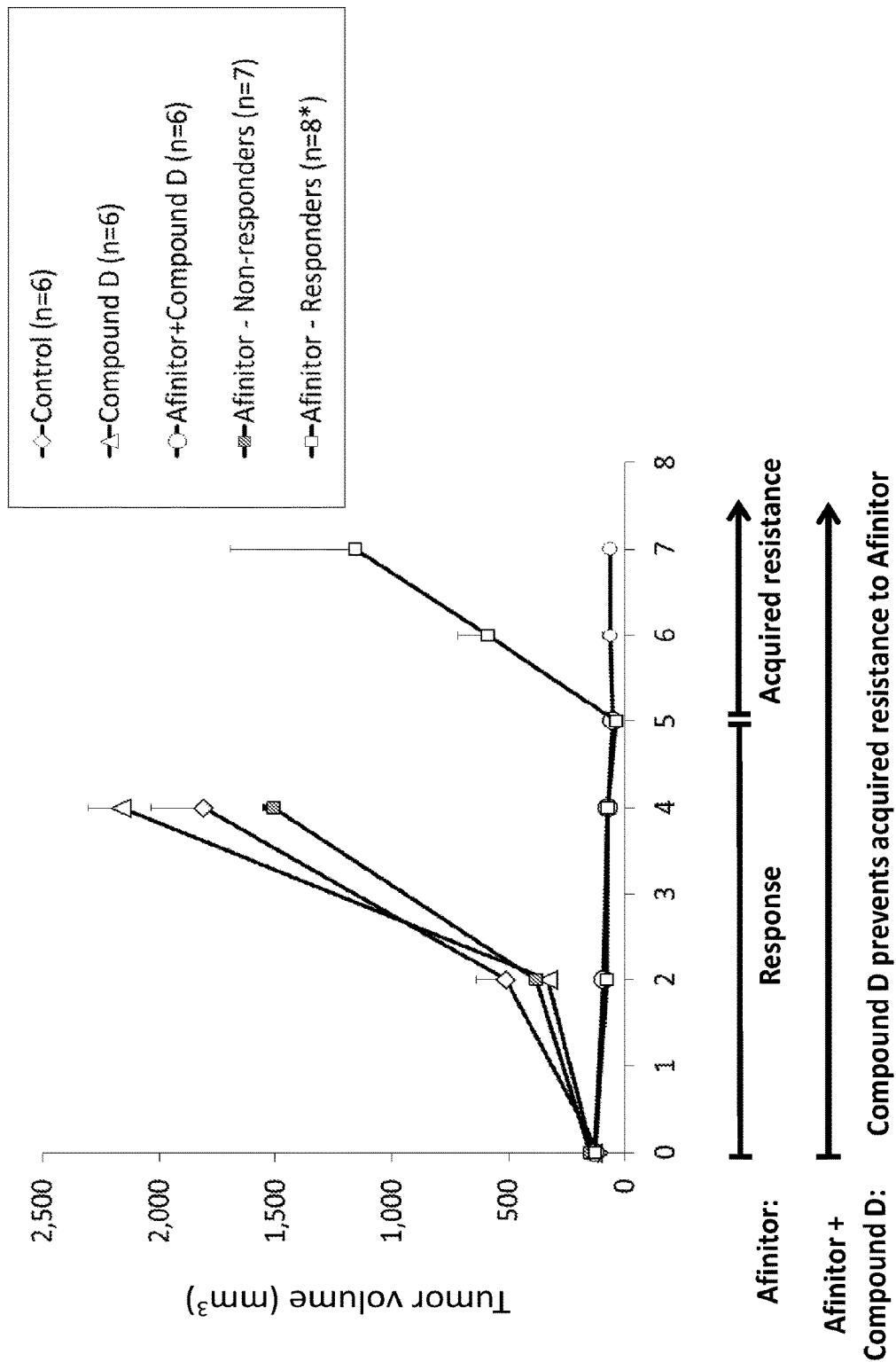
FIGS. 5A-5C. Compound D prevents acquired resistance to Afinitor (A) and leads to regression of Afinitor-resistant tumors (B). Mice implanted with patient-derived xenografts of aggressive Uteral AdenoSarcoma, were first treated when tumors were ~130 mm³ as described in FIG. 4. Mice were treated with either vehicle (diamonds); Afinitor (squares); Compound D (triangles); or Afinitor+Compound D (circles).
Figure 5B:
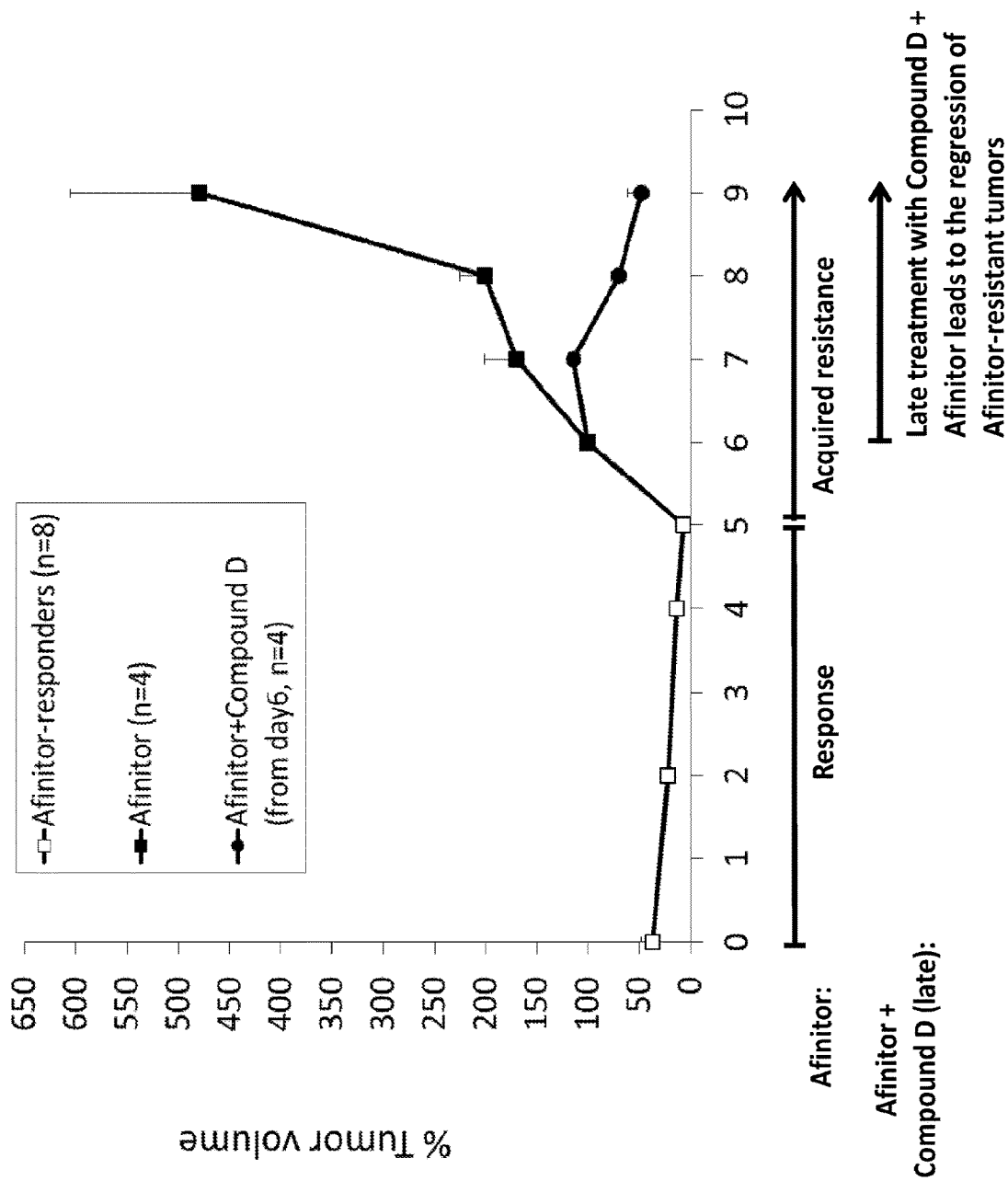

Experimental system: Patient-derived xenograft (PDX) of Uteral AdenoSarcoma biopsy subcutaneous implanted into NodScid mice, described in example 4.
The experiment described in Example 4 (phase I) was extended to phase II (FIG. 5A) and phase III (FIG. 5B) of the experiment. Following treatments described in phase I (example 4), the mice whose tumors reached the end point were sacrificed, and the following treatments were continued.
Phase II:
  1. The Afinitor-responder group (group A, open squares) was administered with Afinitor 5 mg/kg PO, qd (8 mice).
  2. The combined treatment group (open circles) continued to get the Afinitor 5 mg/kg PO (qod)+Compound D 70 mg/kg IV (qod) treatment (6 mice). Afinitor was administered ~4 hr following Compound D.
Phase III:
  The tumors in the Afinitor-responder group (group A) regressed, but while on treatment acquired resistance to Afinitor and aggressively progressed to average tumor size of 590 mm$^3$ on day6. The group was divided to two groups of 4 mice each which received the following treatments on day6 onwards:
    The first continued to get Afinitor 5 mg/kg PO, qd (4 mice)
    and the second got Afinitor 5 mg/kg PO (qod)+Compound D 70 mg/kg IV (qod) combined treatment (4 mice). Afinitor was administered ~4 hr following Compound D.
  The length (l) and the width (w) of the tumors were measured every other day and the volumes of the tumors were calculated as follows: $v=lw^2/2$. The graph in FIG. 5A represents average tumor volumes with standard errors (standard deviations/square root of group size). The graph in FIG. 5B represents growth rates in %, while the 100% for each tumor was defined as its volume at day 6.

Results

The Afinitor-treated group was split to responders (open squares, group A, n=8) vs. non-responders (grey squares, group B, n=7). Afinitor treatment of group A initially induced tumor regression (tumors regressed from average tumor size of 125 mm$^3$ on day0 to 37 mm$^3$ on day5), but while on treatment all tumors developed resistance to Afinitor and aggressively progressed (to average tumor size of 590 mm$^3$ on day6).
Combined treatment of Afinitor and Compound D from day0 (treatment initiation) induced tumor regression and their average tumor volume remained low till the end of the experiment (FIG. 5A, ○). Although the initial tumor has not responded to Compound D alone, the acquired resistance to Afinitor was completely abolished by Compound D. Evidence from the literature suggests that treatment with Afinitor induces IRS up-regulation leading to resistance by the activation of IGF1R/IRS-to-AKT survival pathway. mTOR/S6K is a negative regulator of the IRS proteins. It phosphorylates IRS on Serine residues and thereby down-regulates its levels and decreases its affinity to receptor tyrosine kinases (RTK) IGF1R and IR. Inhibition of mTOR/S6K should stabilize IRS1/2, increase their levels and enhance their complexation with IGF1R and IR, leading to the activation of AKT survival pathway and acquired resistance to mTOR inhibitors. This feedback loop was described in the literature (Crose L. E. S. and Linardic C. M. Sarcoma 2011, Keniry M. and Parsons R. *Cancer Discovery* 2011; 1:203-204) and it has been shown that AKT phosphorylation is a clinically observable phenomenon following treatment with the mTOR inhibitor Afinitor/Everolimus in women with breast cancer. Without wishing to be bound by any particular theory or mechanism of action, it is believed that that eliminating IRS1/2 from the cancer cell by IRS/Stat3 dual modulators such as Compound D and other compounds of formulae (I-IV) described herein will prevent acquired resistance to Afinitor or any other mTOR inhibitor, and may synergize with these inhibitors after resistance has already acquired to induce tumor regression.

Following resistance to Afinitor has been acquired, the mice of group A were divided into two groups, the first remained on Afinitor alone (□) and the second received combined treatment of Afinitor+Compound D starting on day 6 of treatment (●). While tumors significantly progressed under treatment with Afinitor alone (□), the combined treatment of Compound D and Afinitor induced tumor regression (●). The graph in FIG. 5B represents growth rates in %, while the 100% for each tumor was defined as its volume at day 6.

Example 5A: Combined Treatment with Afinitor+Compound D of Highly Aggressive Cancer with No Available Medical Treatment Delayed Acquired Resistance to Afinitor and Achieved Complete Response in 40% of the Group Experimental system: Patient-derived xenograft (PDX) of Uteral AdenoSarcoma biopsy subcutaneous implanted into NodScid mice, described in example 4.

The experiment described in Example 4 was repeated in purchased mice from Harlan.

Treatments:
1. Control: 20% HPbCD 50 ul IP, qod (3 mice).
2. Compound D 70 mg/kg in 20% HPbCD, IV, 3 time a week, qod (3 mice).
3. Afinitor 5 mg/kg PO, 4 times a week (17 mice).
4. Afinitor 5 mg/kg PO (qod)+Compound D 70 mg/kg IV (qod), 3 time a week (5 mice). Afinitor was administered ~4 hr following Compound D.

Treatments ceased on day17.

The length (l) and the width (w) of the tumors were measured every other day and the volumes of the tumors were calculated as follows: $v=lw^2/2$. Graphs represent average tumor volumes with standard errors (standard deviations/square root of group size). Five days following initiation of treatment the tumors of the control group and the Compound D group already reached the end point and mice were sacrificed.

Results

Figure 5C:
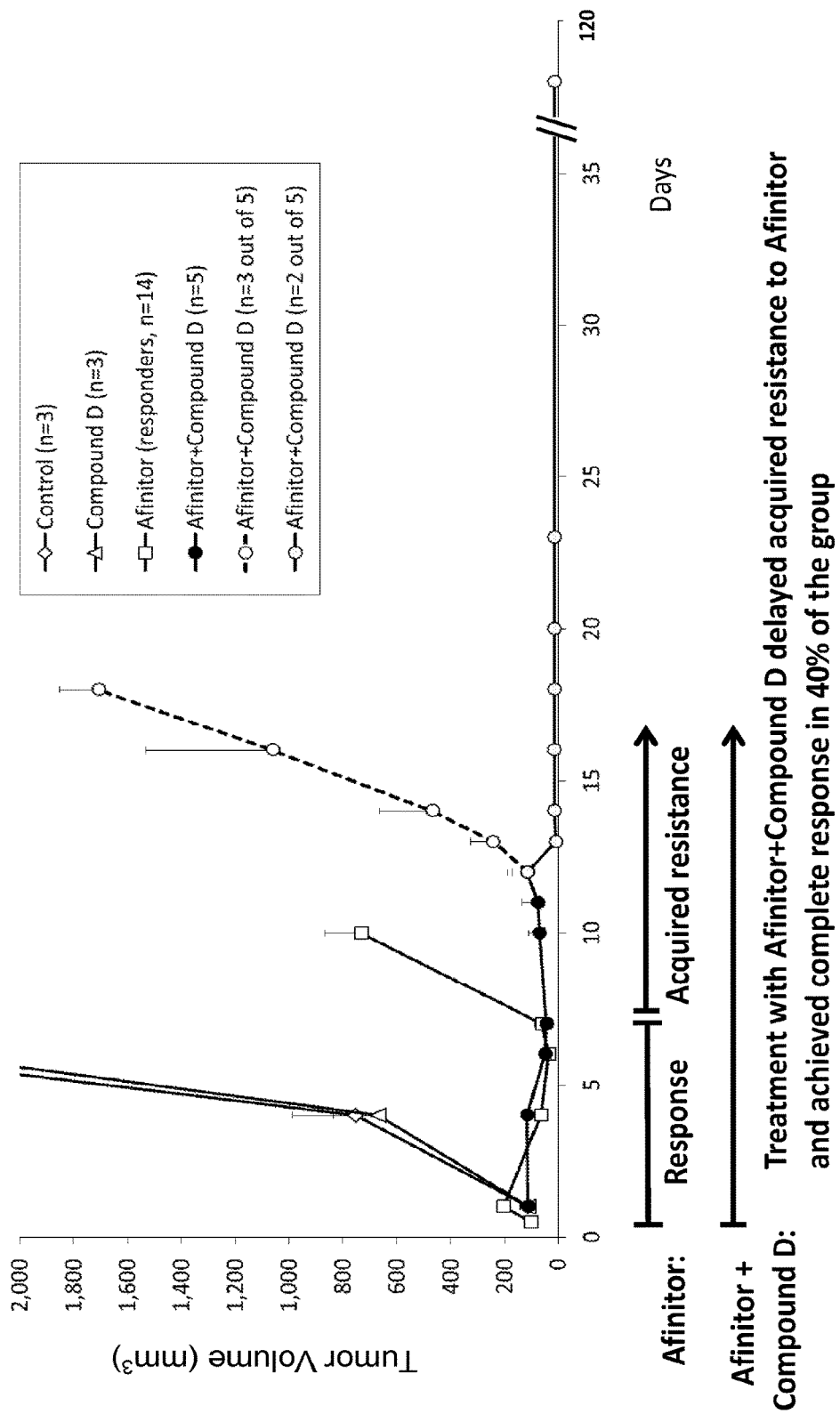

As shown in previous experiment, although Compound D alone (open triangles) had no effect on tumor growth, the combined treatment of Afinitor+Compound D (black circles) led to tumor regression. The tumors in the Afinitor-responder group (14 out of 17 treated mice) regressed, but while on treatment, after one week of treatment, acquired resistance to Afinitor and aggressively progressed (open squares). Combined treatment of Afinitor and Compound D significantly delayed acquired resistance to Afinitor in 60% of the group (3 out of 5 treated mice, open cycles dashed line) and completely erased the tumors in 40% of the group (2 out of 5 treated mice, open cycles continuous line). These two mice were kept alive with no further treatment and remained free of disease after more than 3 months with no further treatment (FIG. 5C).

Example 6

I. Cell Lines
 A375 (human melanoma), HCT15 (colon cancer), SK-ES.1 (Ewing sarcoma), NCI-H460 (lung cancer) and PC3 (prostate cancer) were cultured in RPMI with 10% fetal calf serum (FCS).
 HepG2 (hepatocarcinoma) were cultured in Dulbecco's Modified Eagle Medium (DMEM) and F12 (1:1) containing 10% FCS
 DU145 (prostate cancer) were cultured in RPMI containing 5% FCS and 5 mg/L insulin.
 All cell lines were obtained from the American Type Culture Collection. YUMAC, YURIF, YUSIK (all human melanoma, kindly provided by Prof. Ruth Halaban, Yale University, New Haven, Conn.) were cultured in OptiMEM containing 5% FCS. M571, M2068, M560n (all human melanoma, kindly provided by Dr. Michal Lotem, Hadassah Hospital, Jerusalem, Israel) were maintained in RPMI, DMEM and F12 (1:3:1) containing 10% FCS. 451-Lu (human melanoma) and 451-Lu-BR (PLX4032-resistant melanoma; ref. 32) were maintained in RPMI containing 5% FCS (media for resistant lines contained 1 mmol/L PLX4032). All media were supplemented with 100 U/mL penicillin and 100 mg/mL streptomycin and all cells were grown at 37° C./5% $CO_2$.
 All melanoma cells used and discussed in FIGS. 6-9 and table 1 are from human origin and bearing the mutated $BRAF^{600K/E}$.

II. Cell Proliferation
 Cells were grown in complete medium and treated with inhibitors one day following seeding. 72 hours later, the surviving cells were quantified by methylene blue staining or by WST-1 staining for nonadherent cells (Roche).

III. Immunoblots
 Cells were treated as indicated in FIGS. 6-9 and the corresponding figure legends, following overnight serum-starvation (unless indicated differently). When cells were treated with both PLX4032 and compounds A or D, PLX4032 was added 3-4 hr following the compounds.
 Cells were lysed with boiling sample buffer (10% glycerol, 50 mmol/L Tris-HCl, pH 6.8, 3% SDS, and 5% 2-mercaptoethanol). Western blot analysis was conducted in 8% SDS-PAGE, using antibodies described below.
 Aliquots of cell extracts containing equal amounts of protein were resolved by 8% SDS/PAGE and electroblotted onto nitrocellulose filters. The membranes were blocked with low-fat milk diluted 1:20 in TBST (NaCl/Tris containing 0.2% Tween-20) for 0.5 hr, incubated with Rabbit anti-phosphoY705-Stat3 antibody (Cell signaling cat #9131), Mouse anti-ERK-diphosphorylated-YT (Sigma Aldrich cat #M8159) or anti-PARP antibodies overnight at 4 C in 5% BSA in TBST containing 0.05% azid, washed extensively with TBST and then incubated with horseradish peroxidase-conjugated secondary antibodies for 45 min at room temperature in 5% BSA in TB ST.

Immunoreactive bands were visualized using enhanced chemiluminescence. Membranes were re-blotted with Mouse anti-Stat3 antibody (Transduction labs cat #21320) or with Rabbit anti AKT1/2 (Santa cruz cat #sc-8312) or Anti-Actin as described above.

IV. Chemotaxis of Peripheral Blood Mononuclear Cells (PBMCs)

A375 cells were seeded in 96-well plates (6000 cells/well) and grown overnight. Cells were treated with Compound A and washed twice with the medium 4 hrs after treatment where indicated (Wash). 30 hrs following treatment 150 ul of medium were transferred to lower plate of chemotaxis device. 10,000 PBMCs/75 ul medium/well were added to the upper plate. In addition, PBMCs were added into lower plate as positive control (FIG. 9B—Cell Titer Glo calibration graph, 10-10,000 cells/well). Chemotaxis was examined 24 hrs later by Cell Titer Glo analysis of the lower plate. In addition, survival of A375 cells was analyzed by Methylene blue 30 hrs after treatment with Compound A.

TABLE 1

The dual modulators of IRS/Stat3 potently inhibit the proliferation and viability of various cancer cells as compared to IGF1R inhibitor OSI-906.

| Indication | Cell line | IC$_{50}$ (UM) | | |
|---|---|---|---|---|
| | | Compound D | Compound A | OSI-906 |
| Prostate cancer | PC3 | 0.5 | 0.8 | >10 |
| Melanoma | Mel1617-Pa | 0.2 | 0.3 | >3 |
| | Mel1617-BR | 0.3 | 0.3 | >3 |
| | 451Lu-Pa | 0.3 | ND | >>3 |
| | 451Lu-BR | 0.6 | ~0.7 | >>3 |
| Colon cancer | HCT15 | 0.8 | ND | >>3 |
| Multiple Myeloma | MM1S | 0.2 | 0.3 | 0.2 |
| Hepatocarcinoma | HepG2 | 0.7 | 1 | 8.3 |

Cells were plated in 96-well plates in 5-10% FCS in medium; a day later exposed to various concentrations of compound A, compound D or OSI-906 and 3 days later stained with methylene-blue and the relative cell number was quantified.

Results

Compounds A and D which were previously shown to induce IRS1/2 serine phosphorylation, were found to efficiently induce a reduction in Y705-phosphorylation levels of Stat3 in cancer cells. These dual modulators of IRS/Stat3 potently inhibit Stat3 phosphorylation (pStat3) in a dose-dependent manner (FIG. 6A) without affecting Stat3 protein levels. The inhibitory effect demonstrated by compound A and D is potentiated with time: IC50 values of both compounds were ~2 µM 1.3 hr post-treatment and decreased to <1 µM 3 hr later. The described inhibitory effect on Stat3 phosphorylation levels is long-term (FIG. 6B) as it can be detected long after the modulators were washed out the cells (FIG. 6C). FIG. 6C also demonstrates that a short exposure of A375 melanoma cells to Compound D was sufficient to induce cell apoptosis 24 and 48 hr later. The blockage of Stat3 Y705-phosphorylation is exemplified for compounds A, B, C, D, F, IV-1, IV-2, IV-3 and IV-4.

Since Stat3 is reported to be involved both in survival and drug resistance and in immune evasion of various cancer types, the ability of the Stat3/IRS dual modulators to sensitize tumors to specific PK inhibitory drugs and immunotherapies, respectively, was tested.

Figure 7A:
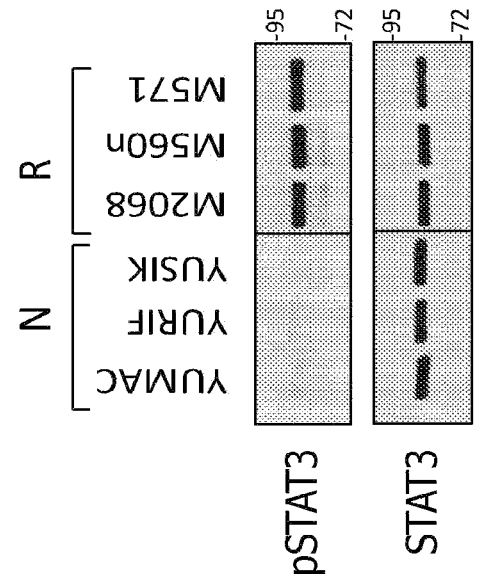
FIGS. 7A-7E. Acquired resistance to BRAF inhibitors (BRAFi) in melanoma is accompanied by enhanced Stat3 phosphorylation levels, and treatment with BRAFi of human melanoma cells surprisingly induces a dramatic increase in pStat3.
Figure 7B:
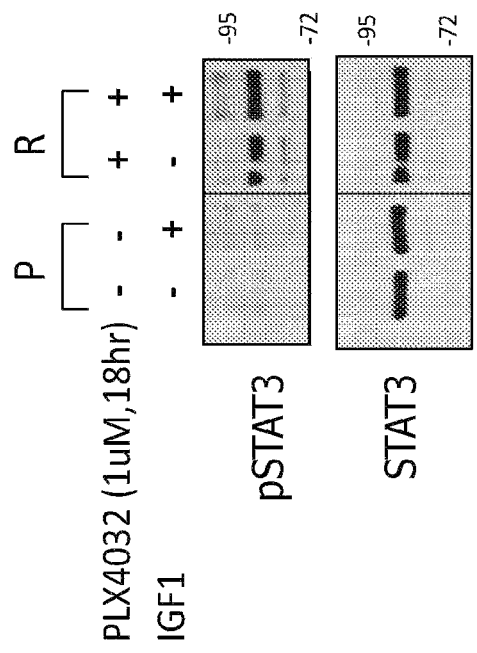

The phosphorylation levels of Stat3 in melanoma that acquired resistance to BRAF inhibitor (BRAFi) such as PLX4032 (also known as Vemurafenib or Zelboraf) is significantly higher as compared to the parent melanoma cells/tumors (FIGS. 7A and 7B). This is shown in a metastatic melanoma clone 451-LU-BR [Villanueva et al. *Cancer Cell* 2010; 18:683-95] isolated following 6-months treatment with BRAFi (R), compared to the parent metastatic melanoma 451-LU cell line before treatment (P). Further demonstrated are the higher levels of Stat3 phosphorylation in cells (R) taken from patients (M2068, M560n, M571) that have been treated with PLX4032 and developed resistance towards it, compared to melanoma cells from naïve patients (N) that carry mutated BRAF (YUMAC, YURIF, YUSIK) but were not yet treated with BRAFi (FIG. 7B).

The protein levels of Stat3 are similar in all samples, only the phosphorylation levels are dramatically enhanced in the PLX4032-resistant cells.

Figure 7D:
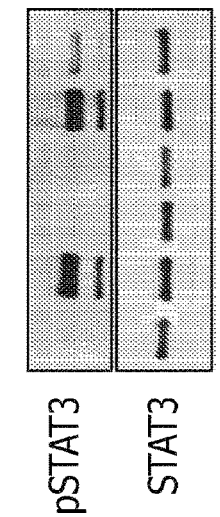
Figure 7C:
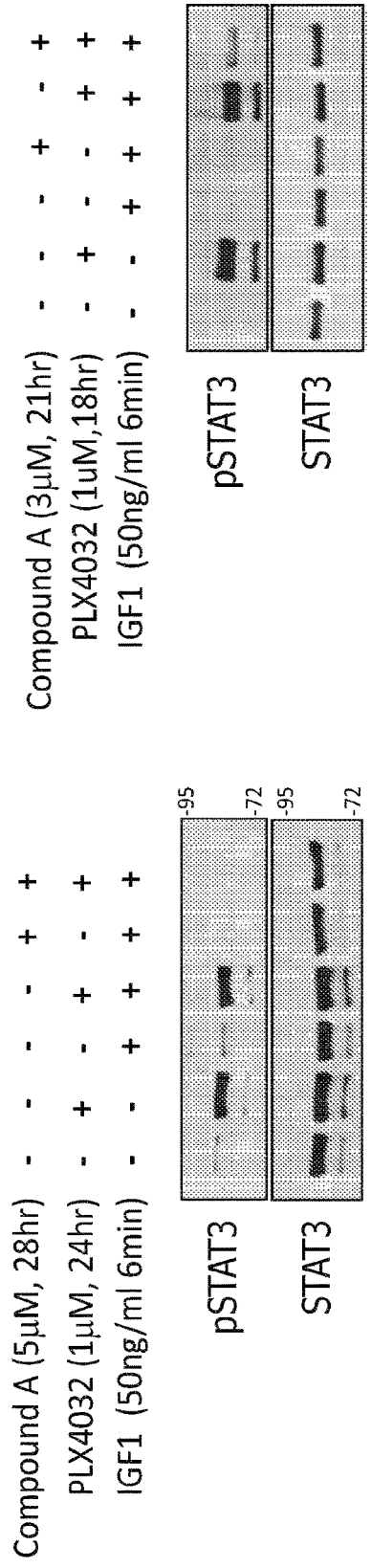
Figure 7E:
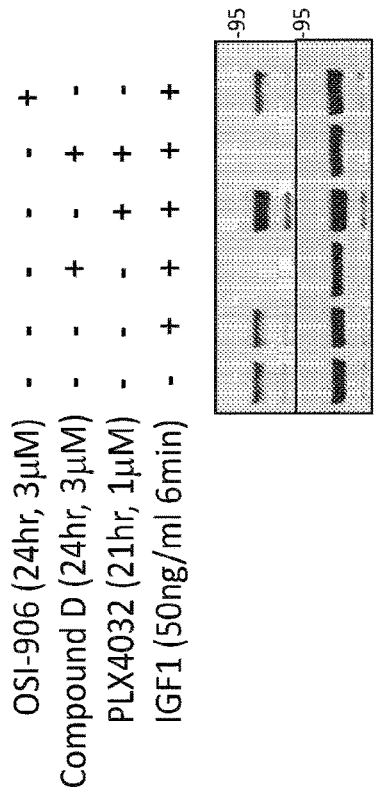

Surprisingly, it was discovered in PLX4032-sensitive melanoma cells that treatment with 1 µM PLX4032 for 18-24 hr induced a marked induction in Stat3 Y705-phosphorylation (pStat3). It was tested and demonstrated in three different human metastatic melanoma cell lines (FIG. 7C-E). The results in FIG. 7 suggest that the increase in pStat3 may play a role in acquired resistance to BRAFi and that resistant cells adapt high constant pStat3 level as a survival factor. Thereby it was speculated that combining dual IRS/Stat3 modulators with BRAFi may prevent acquired resistance to BRAFi as well as to other drugs inducing up-regulation of pStat3 and/or IRS1 and/or IRS2. The potential of the IRS/Stat3 dual modulators to prevent acquired resistance to such drugs is indeed demonstrated in Example 1, showing that compound D prevented acquired resistance to Erlotinib in HNSCC derived from a patient and implanted to mice.

Furthermore, pStat3 has a major role in immune evasion of the tumor, it upregulates the expression and secretion of immune-suppressive factors and down-regulates proinflammatory mediators, thereby masking the tumors from the local immune system. In addition to cancer cells, diverse immune subsets in the tumor micro-environment also display constitutively activated Stat3, and blocking Stat3 in immune cells may also elicit potent anti tumor immune response (increased cytotoxicity of NK cells and neutrophils, T cell activation and increased tumor infiltration, etc.). Therefore, it was speculated that combining our dual IRS/Stat3 modulators with immunotherapy will down-regulate pSTAT3 and sensitize the tumor to various immunotherapy agents.

Herein it is demonstrated that the IRS/Stat3 dual modulators, represented by compounds A & D, block both the basal and the PLX4032-induced levels of pStat3, while the IGF1R/IR TK inhibitor OSI-906 had no effect on pStat3 levels (FIGS. 7E & 8A). Testing the significance of this finding in terms of anti-cancer activity, the anti-proliferative activity of the IRS/Stat3 dual modulators vs. the IGF1R/IR TK inhibitor OSI-906 was compared in various cancer types. Table 1 shows that compounds A and D are far more effective than OSI-906 in various melanoma cells (both PLX4032-resistant and PLX4032-sensitive); in colon cancer cells resistant to various chemotherapies and EGFRi; in prostate cancer cells (resistant to several chemotherapies) and hepatocellular carcinoma (resistant to EGFRi). These differences between the dual modulators and the tyrosine kinase inhibitor of IGF1R/IR suggest that inhibiting both the Stat3 and IRS, central junction proteins highly involved in survival and drug resistance, may contribute to the potential of the dual modulators to sensitize resistant cancer cells to various therapies.

Figure 6A:
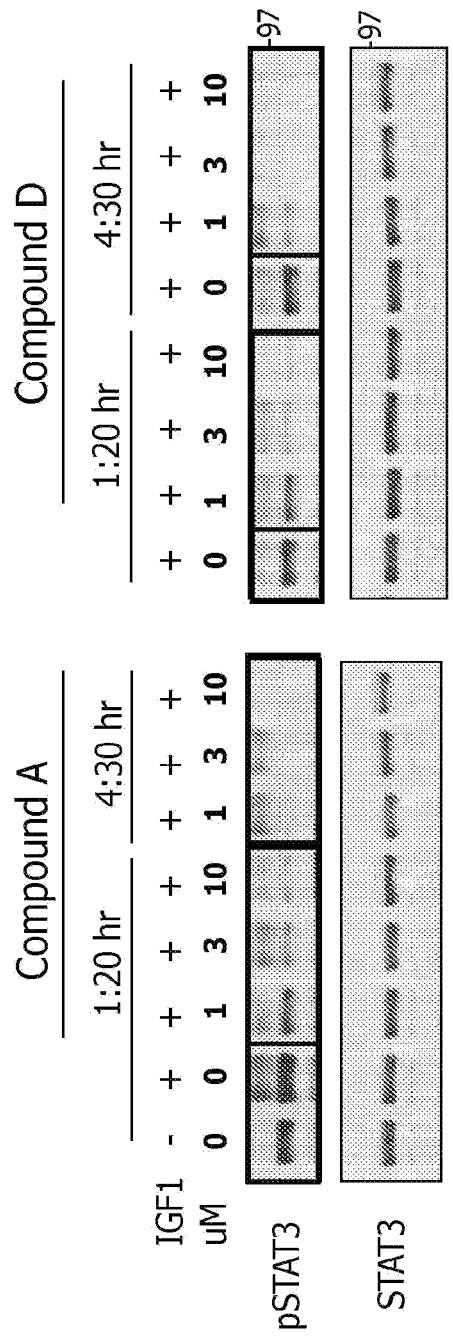
FIGS. 6A-6E. Dual modulators of IRS/Stat3 potently inhibit Stat3 phosphorylation in intact cells in a dose-dependent manner, and their inhibitory effect on Stat3 lasts long after the modulators are washed out the cells. A. Human melanoma A375 cells were treated with the indicated concentrations of compounds A or D for 1.3 and 4.5 hr. Cells were lysed and immunoblotted with antibodies against phospho-Y705 Stat3 (pSTAT3) and Stat3. A dose response inhibition of pStat3 with sub-micromolar IC50 values is demonstrated, and the effect is potentiated in time. B. Cells were treated with 2 µM Compound A and lysed following the indicated times. C. A375 cells were treated with compound D for 4 hr, then washed with medium several times and lysed after 4, 24 and 48 hr of incubation without inhibitors. D. Dose-dependent inhibition of pStat3 showing IC50 values of <1 µM for compounds A, C, D; 1 µM for compound B and 2 µM for compound F. E. Complete inhibition of Stat3 Y705-phosphorylation in melanoma A375 cells 24 hr post treatment with 3 µM compounds IV-1, IV-2, IV-3 and IV-4.
Figure 6B:
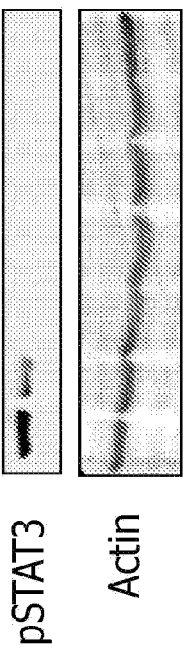
Figure 6C:
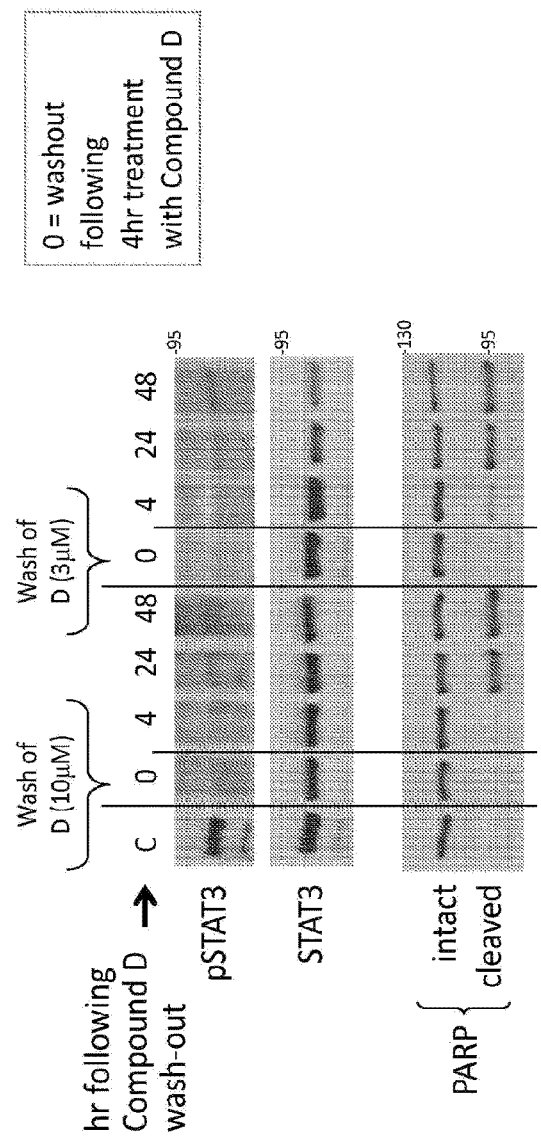
Figure 6D:
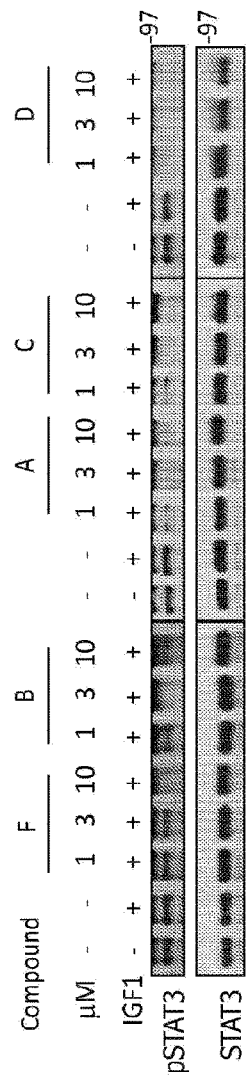
Figure 6E:
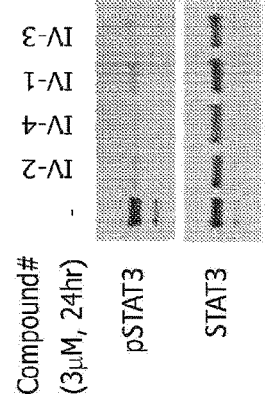

As previously described in FIGS. 6A&B, there are increased levels of pStat3 in melanoma cells which developed resistance to BRAFi. FIGS. 8A&B show that compounds A & D block Stat3 phosphorylation completely in these PLX4032-resistant clones of melanoma cell lines (451-LU-BR described above and Mel1617-BR [Villanueva et al. *Cancer Cell* 2010; 18:683-95]) as well as in melanoma cells derived from two patients [M2068 (i) & M571 (ii)] who have acquired resistance to PLX4032 treatment (FIG. 8C). FIG. 8C demonstrates better activity of compound D compared with compound A. These results suggest that the IRS/Stat3 dual modulators may re-sensitize melanoma cells which have acquired resistance to BRAFi, and combined therapy of the IRS/Stat3 dual modulators with BRAFi may induce tumor regression of the resistant tumors. The potential of the IRS/Stat3 dual modulators to re-sensitize drug-resistant tumors to the drug, is indeed demonstrated in examples 2 and 3, demonstrating that the combination of compound D with Erlotinib induces regression of Erlotinib-resistant HNSCC tumors in mice.

Figure 8D:
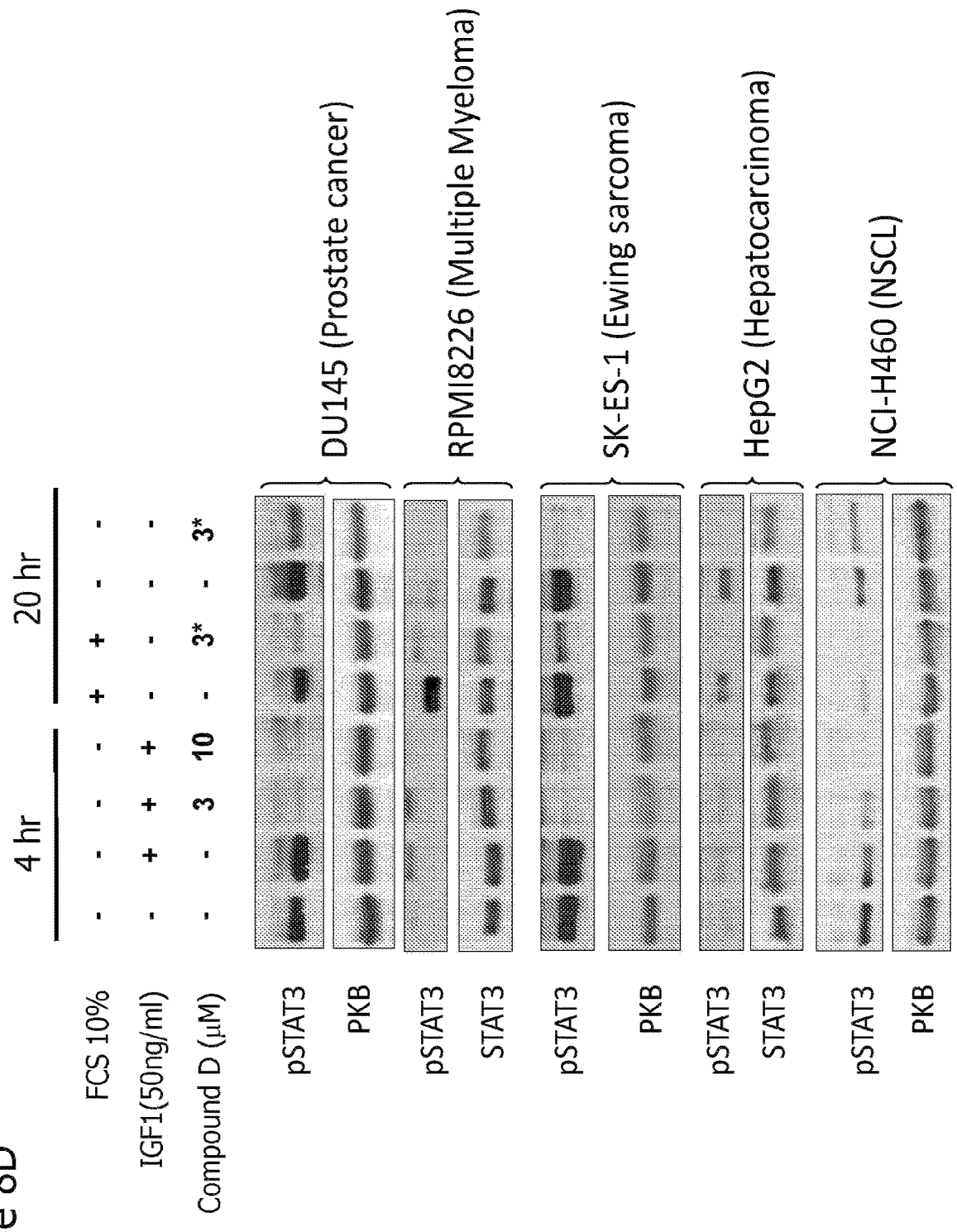

The capability of the IRS/Stat3 dual modulators to inhibit pStat3 was demonstrated in various cancer types, as previously demonstrated for their effect on IRS1/2 Ser-phosphorylation and elimination. FIG. 8D exemplifies their inhibitory activity on Stat3 Y705 phosphorylation (pStat3) in prostate cancer, multiple myeloma, Ewing sarcoma, hepatocellular carcinoma and NSCL.

Figure 9A:
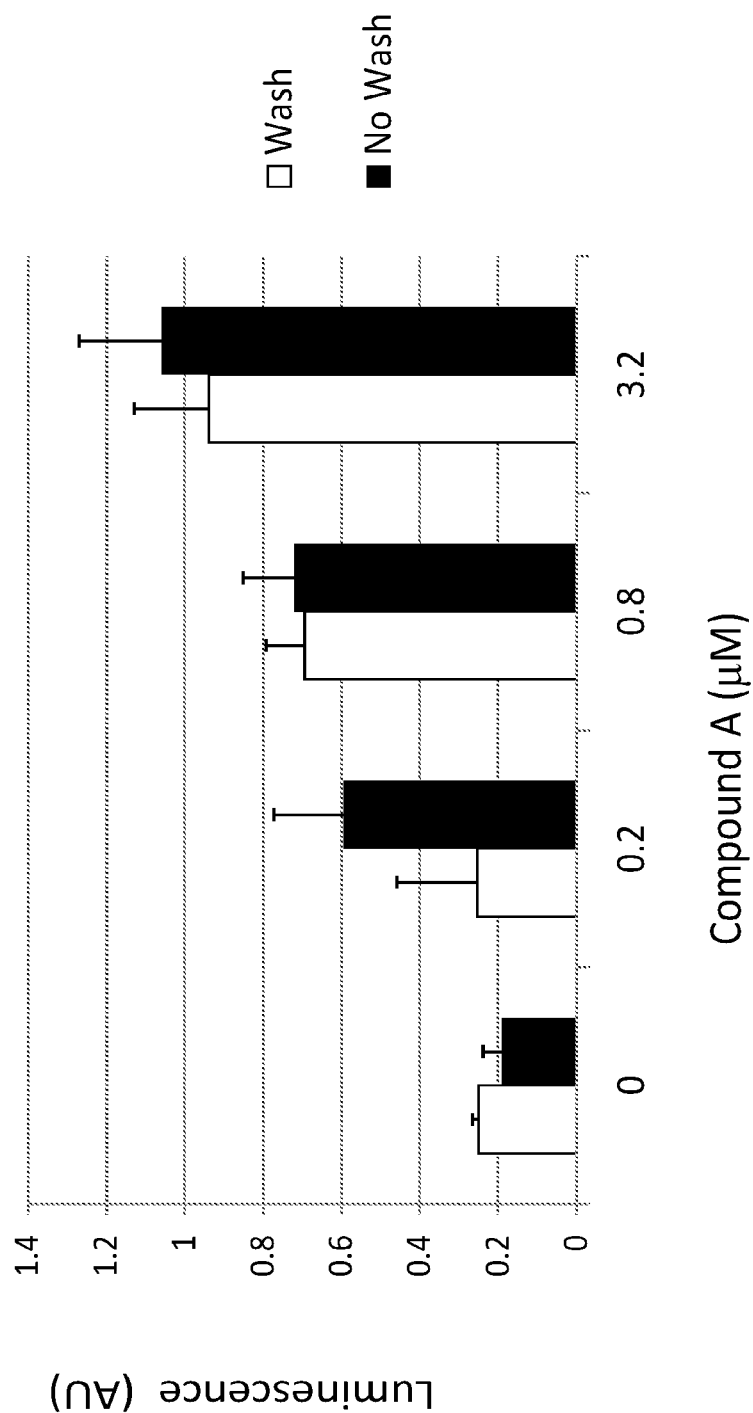
FIGS. 9A-9B. Treatment of melanoma A375 cells with Compound A induces PBMC's chemotaxis. A375 cells were treated with the indicated concentrations of Compound A and washed twice with the medium 4 hrs after treatment where indicated (Wash). 30 hrs following treatment the cell medium was transferred to lower plate of chemotaxis device. 10,000 PBMCs/well were added to the upper plate. In addition, PBMCs were added into lower plate as positive control.
Figure 9B:
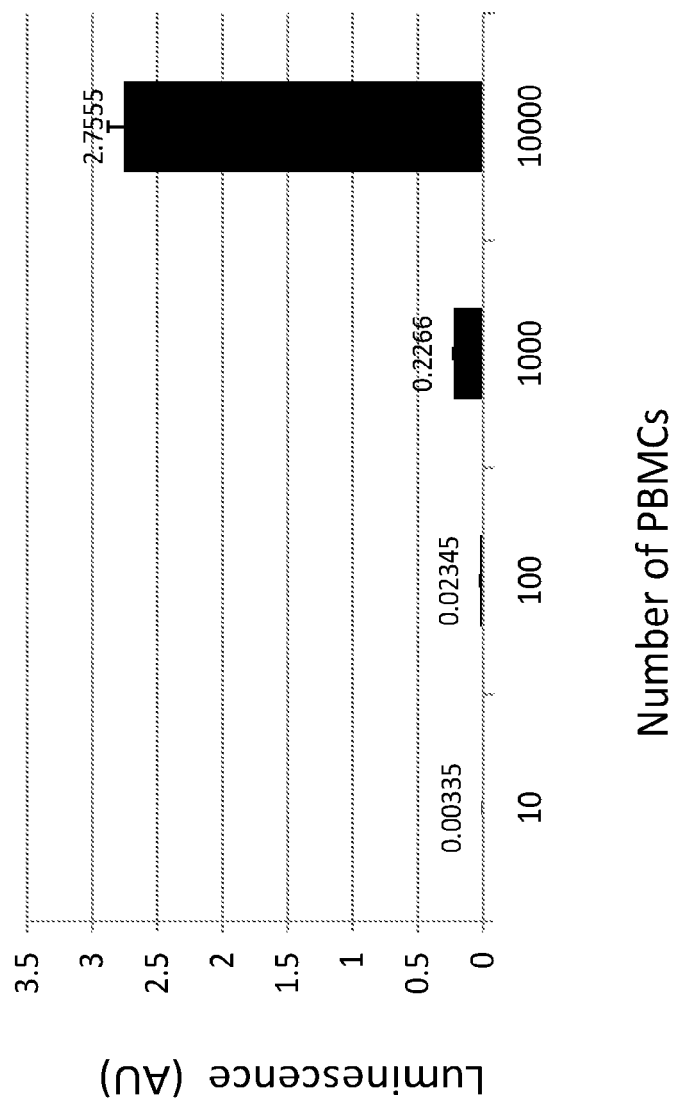

The immune system is a powerful, largely untapped force for fighting tumors. Tumors have developed sophisticated mechanisms to evade the immune system. Stat3 has a crucial role in mediating the crosstalk between tumor cells and tumor-interacting immune cells. Targeting Stat3 in tumors involves bystander tumor cell killing associated with infiltration of various immune effector cells. Thus, it was tested whether treatment of tumor cells with IRS/Stat3 dual modulators may induce the recruitment of peripheral blood mononuclear cells towards the cancer cells. Human melanoma A375 cells were treated with increasing concentrations of compound A and washed twice with the medium 4 hrs post-treatment where indicated (Wash). 30 hrs following treatment the cell medium was transferred to lower plate of chemotaxis device, and 10,000 human PBMCs/well were added to the upper plate. Chemotaxis of the PBMCs towards the A375 medium samples was examined 24 hrs later by Cell Titer Glo analysis of the lower plate As shown in FIG. 9A a dose dependent chemotaxis was detected, suggesting compound A-regulated cytokine expression/secretion inducing PBMC's recruitment towards the treated tumor. Thus, combining our dual modulators with immunotherapy may gain enhanced anti-tumor effects. These IRS/Stat3 dual modulators should sensitize the tumors to other immunotherapies or PK inhibitors (EGFRi, mTORi etc) by affecting directly and indirectly the tumor cells and the tumor's microenvironment, including the tumor-interacting immune cells.

Example 7: Combined Treatment of EGFR Antibody Cetuximab with Compound D Shows a Dramatic Delay in Tumor Recurrence Compared to Cetuximab Alone in Mice Implanted with a Tumor from a Head & Neck Squamous Cell Carcinoma (HNSCC) Patient. The Same is True when Cetuximab+Afatinib are Used Instead of Cetuximab Experimental system: Patient-derived xenograft (PDX) of HNSCC tumor biopsy subcutaneous implanted into Nod-Scid mice.

I. Animals and Biopsy
  Implantation of HNSCC tumor biopsy graft (P6) into NodScid mice for efficacy study: Few months following implantation of frozen HNSCC tumor biopsy graft (P1) in mice, tumor cells (P6) were injected into NodScid mice (generated by in-house breeding), using the same procedure described for implantation of P1. The original biopsy is the same as described above and the P indicates passages (implantation number in mice).
  Onset of tumor growth (palpable tumor mass) was detected four days following cell injection. Five days later, treatments initiated in mice which developed tumors sized around 113 $mm^3$. The mice were randomly divided into 6 treatment groups including 4 animals in the groups treated with Cetuximab, Cetuximab+Afatinib, Cetuximab+Compound D, Cetuximab+Afatinib+Compound D, and 3 mice in the groups treated with Vehicle or Compound D. Treatments initiated simultaneously (on day 0) and applied for a period of 9 days.

II. Treatments and Procedures
  Treatment groups included:
  1. Vehicle-control: Vehicle (0.5% Hydroxymethyl-cellulose, 0.4% Tween-80) 200 µl PO (5 times/week, qd).
  2. Compound D 70 mg/kg in HPbCD, IV (3 times/week, qod).
  3. Cetuximab 1 mg/mouse IP (2 times/week).
  4. Cetuximab 1 mg/mouse IP (2 times/week)+Compound D 70 mg/kg IV (3 times/week). Cetuximab was administered ~4 hr following Compound D, when administered at the same days.
  5. Cetuximab 1 mg/mouse IP (2 times/week)+Afatinib 25 mg/kg in vehicle PO (5 times/week)
  6. Cetuximab 1 mg/mouse IP (2 times/week)+Afatinib 25 mg/kg PO (5 times/week)+Compound D 70 mg/kg IV (3 times/week). Cetuximab and/or Afatinib were administered ~4 hr following Compound D, when administered at the same days.

The length (l) and the width (w) of the tumors were measured 2-4 times a week and the volumes of the tumors were calculated as follows: $v=lw^2/2$. Graphs represent average tumor volumes with standard errors (standard deviations/square root of group size). Mice weight and behavior were examined at least once a week. Mice were sacrificed and the tumors were excised for biochemical and genomic analysis.

Results

Figure 10:
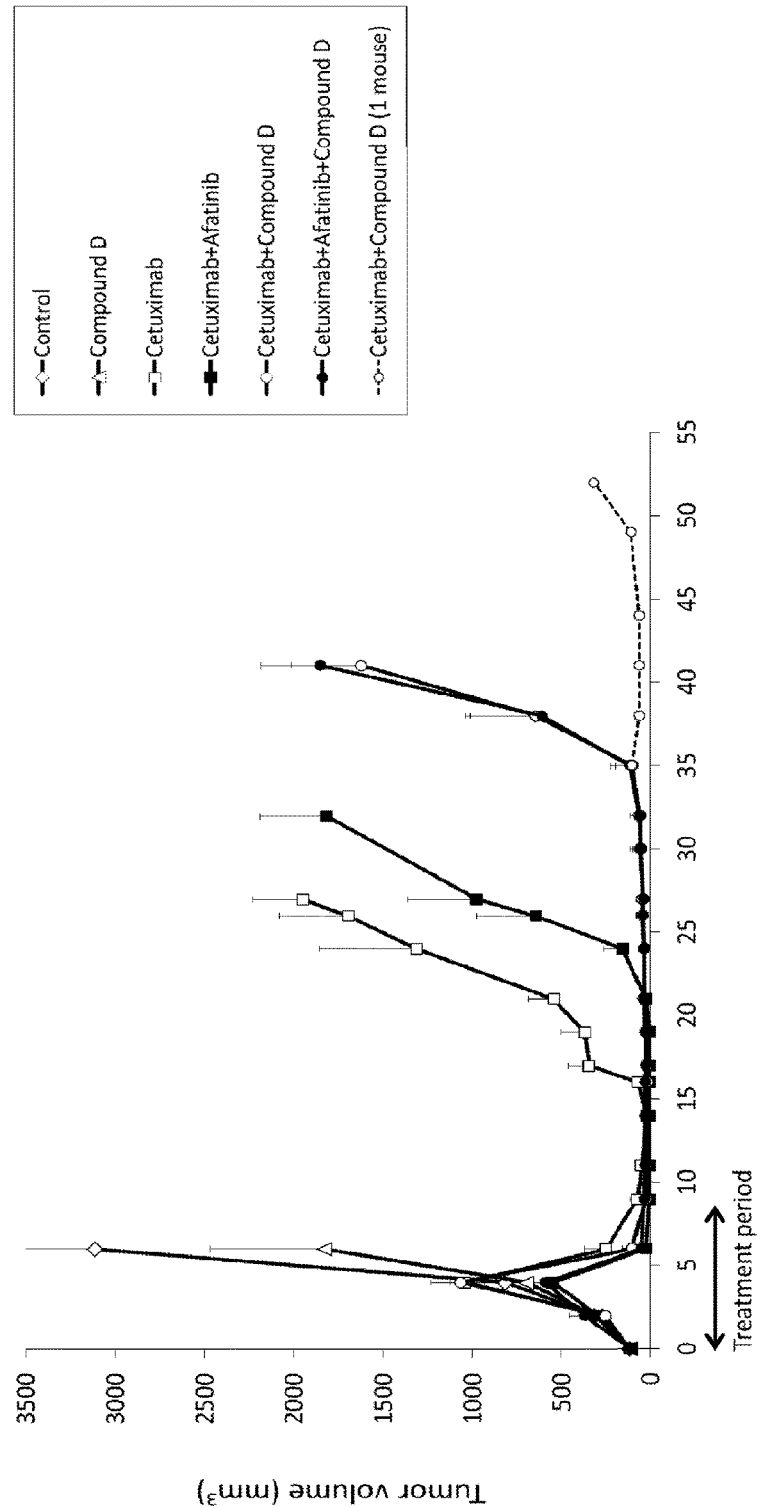
FIG. 10. Combined treatment of Cetuximab±Afatinib with Compound D shows a dramatic delay in tumor recurrence compared to Cetuximab±Afatinib alone in mice implanted with a tumor from a HNSCC patient. Mice were treated for 9 days with (a) vehicle (◇); (b) Compound D (Δ); (c) Cetuximab (□); (d) Cetuximab+Afatinib (⌐); (e) Cetuximab+Compound D (○); or (e) Cetuximab+Afatinib+Compound D (●). Treatments were initiated when average tumor size was ~110 mm³. Combined treatment of Compound D with either Cetuximab or Cetuximab+Afatinib for 9 days only, significantly delayed recurrence of regressed tumors and prolonged response to Cetuximab or to Cetuximab+Afatinib.

As shown in FIG. 10, at the first 4 days of treatment all tumors progressed, but then, treatment with either Cetuximab, Cetuximab+Compound D, Cetuximab+Afatinib or Cetuximab+Afatinib+Compound D led to dramatic tumor regression in all mice, while all tumors in the vehicle-treated mice and in the Compound D-treated mice (as a stand-alone treatment) aggressively progressed. Treatments applied for a period of 9 days only. Eight days following cease of treatments the tumors of the Cetuximab-treated group started re-growing and aggressively progressed and a week later the tumors of the Cetuximab+Afatinib treated group progressed, while the combinations with Compound D extended the positive responses to >4 weeks following end of treatment.

Afatinib is a second-generation irreversible EGFR tyrosine kinase inhibitor developed to overcome acquired resistance to EGFR blockers, stems from EGFR T790M mutation, which is the most frequent mechanism of acquired resistance to EGFR tyrosine kinase inhibitors.

Conclusion

Combined treatment of Compound D with either Cetuximab or even Cetuximab+Afatinib for 9 days only, significantly delayed recurrence of regressed tumors and prolonged response to Cetuximab or to Cetuximab+Afatinib.

Example 8: Compound D Synergizes with the Combination of Drugs, Comprising Inhibitors of Mutated-BRAF and MEK, to Induce Dramatic Tumor Regression in Mice Implanted with Tumor Cells from a Melanoma Patient Who has Acquired Resistance to Vemurafenib Experimental system: Patient-derived xenograft (PDX) of melanoma subcutaneous injected into NodScid mice.
I. Animals and Biopsy
  Biopsy: Biopsy was excised from a melanoma patient harboring mutated-BRaf$^{V600E}$ who has shown short response to Vemurafenib, and cells were seeded in plates. Early passage cells (million cells/mouse) were sub-cutaneously (SC) injected into NOD.CB17-Prkdc$^{scid}$/J (NodScid) female mice 10 weeks old (generated by in-house breeding). Onset of tumors was detected five days later, and treatments initiated seven days following cell-injection when average tumor volume was ~60 mm³.
II. Treatments and Procedures
  When tumor size was ~60 mm³ (day0) the following treatments initiated:
    5. Control (vehicle): Vehicle of Vemurafenib+Trametinib PO—5% Propylene Glycol, 0.5% Tween-80, 30% PEG 400 in Sterile DDW (5 times/week, qd), 6mice
    6. Compound D 70 mg/kg in 20% 2-Hydroxypropyl-β-cyclodextrin (HPbCD), IV (3 times/week, qod), 6 mice
    7. Vemurafenib 75 mg/kg+Trametinib 1 mg/kg PO (5 times/week, qd), 20 mice.
    8. Vemurafenib 75 mg/kg+Trametinib 1 mg/kg PO (5 times/week, qd)+Compound D 70 mg/kg IV (3 times/week), 7 mice. Vemurafenib+Trametinib were administered ~4 hr following Compound D, when administered on the same days.
  All treatments for each of the treatment groups 1-4 were initiated simultaneously.
  The length (l) and the width (w) of the tumors were measured 4 times a week and the volumes of the tumors were calculated as follows: v=lw²/2. Graphs represent average tumor volumes with standard errors (standard deviations/square root of group size). Mice weight and behavior were examined at least twice a week.

Results

Figure 11:
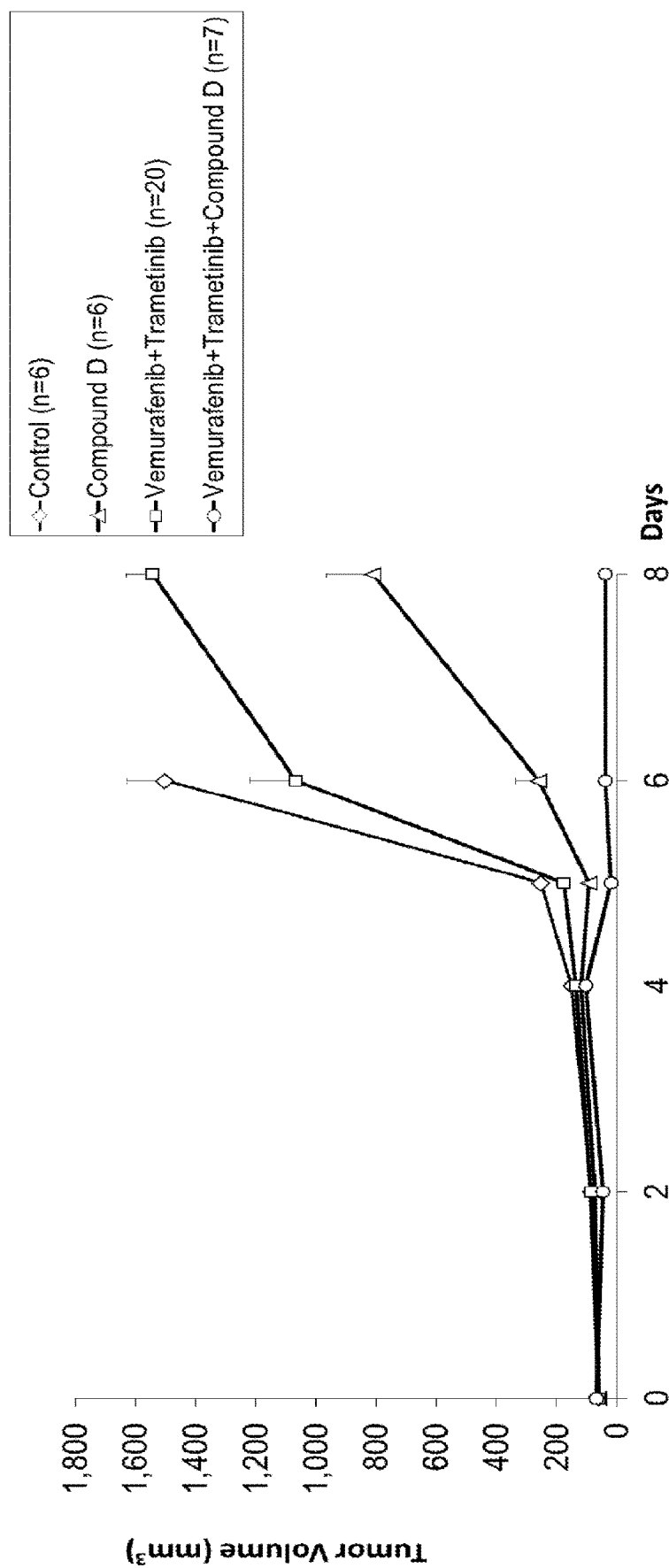
FIG. 11. Compound D synergizes with the combination of mutated-BRAF inhibitor (BRAFi) and MEK inhibitor (MEKi), to induce dramatic tumor regression in mice implanted with tumor cells from a melanoma patient who has acquired resistance to mutated-BRAF inhibitory drug treatment. Mice were treated with (a) vehicle (◇); (b) Trametinib (MEKi)+Vemurafenib (BRAFi) (□); (c) Compound D (Δ); or (d) Trametinib+Vemurafenib+Compound D (○). Treatments were initiated when average tumor size was ~60 mm³. Tumors aggressively progressed in all mice treated with Trametinib+Vemurafenib, while combined treatment of Trametinib+Vemurafenib with Compound D induced tumor regression in all mice in this group and none of them regrew while on treatment. P values of Trametinib+Vemurafenib+Compound D vs. Trametinib+Vemurafenib=0.0001.

As shown in FIG. 11, while on treatment with Vemurafenib+Trametinib, tumors aggressively progressed on day6 of treatment (FIG. 11, open squares), all tumors in the combined treatment with Compound D (Vemurafenib+Trametinib+Compound D) regressed (FIG. 11, open circles).

Vemurafenib was the first mutated-BRaf inhibitor approved by the FDA for the treatment of melanoma patients harboring mutation in BRaf$^{V600}$. Unfortunately, few months after treatment initiation the patients developed resistance to Vemurafenib and regressed tumors resurged more aggressively. Consequently, the combination of mutated-BRaf inhibitor and MEK inhibitor was approved for the treatment of melanoma patients harboring mutation in BRaf$^{V600}$, but still resistance is acquired. We show that two feedback pathways are induced by treatment of cells in culture with Vemurafenib (mutated-BRaf inhibitor) or Trametinib (MEK inhibitor)—the levels of both IRS and phosphorylated STAT5 increase. Both pathways are central for cell survival, proliferation, metastasis and angiogenesis. Without wishing to be bound by any particular theory or mechanism of action, Compound D and the compounds of formulae (I-IV) described herein are dual inhibitors of IRS1/2 and Stat3 and, therefore, should antagonize these mechanisms induced by the MAPK pathway inhibitors (like mutated BRaf inhibitors and MEK inhibitors), synergize with these inhibitors (with each alone or with the combinations of them) and prevent resistance to these inhibitors.

Example 9: Compound D Synergizes with MEK Inhibitor Trametinib to Induce Tumor Regression in Mice Implanted with Tumor from Adenoid Cyctic Carcinoma Patient Harboring Mutation in BRAF Experimental system: Patient-derived xenograft (PDX) of Adenoid Cyctic Carcinoma tumor biopsy subcutaneous implanted into NodScid mice.
I. Animals and Biopsy
  Biopsy: Fresh human primary Adenoid Cyctic Carcinoma tumor biopsy. Genomic analysis revealed mutated BRaf.
  Implantation of Adenoid Cyctic Carcinoma RA_148 tumor biopsy graft into NodScid mice for efficacy study:
  Implantation of tumor biopsy grafts (P0): Fresh human primary Adenoid Cyctic Carcinoma tumor biopsy grafts were sub-cutaneously (SC) implanted into NOD.CB17-Prkdcscid/J (NodScid mice).
  Implantation of tumor biopsy grafts (P5) into NodScid female mice (generated by in-house breeding) for efficacy study, was performed using the same procedure described above for implantation of HNSCC.
  Onset of tumor growth (palpable tumor mass) was detected in all mice five days following cell injection. After three additional days, mice developed tumors with an average size of about 65 mm³. The mice were randomly divided into treatment groups including 5 animals/group. The vehicle-treated group included 4 mice.
II. Treatments and Procedures
  Treatment groups included:
    1. Vehicle-control: vehicle of Trametinib (5% Propylene Glycol, 0.5% Tween-80, 30% PEG 400 in Sterile DDW) 200 μl PO (5 times/week, qd).
    2. Compound D 70 mg/kg in HPbCD, IV (3 times/week, qod).
    3. Trametinib 1 mg/kg PO (5 times/week, qd).

4. Trametinib 1 mg/kg PO (5 times/week, qd)+Compound D 70 mg/kg IV (3 times/week). Trametinib was administered ~4 hr following Compound D, when administered on the same days.

All treatments for each of the treatment groups 1-4 were initiated simultaneously on day0, and the study included two phases of treatments day0-day13 and day24-day31.

The length (l) and the width (w) of the tumors were measured 2-4 times a week and the volumes of the tumors were calculated as follows: $v=lw^2/2$. Graphs represent average tumor volumes with standard errors (standard deviations/square root of group size). Mice weight and behavior were examined at least twice a week.

Results

Figure 12:
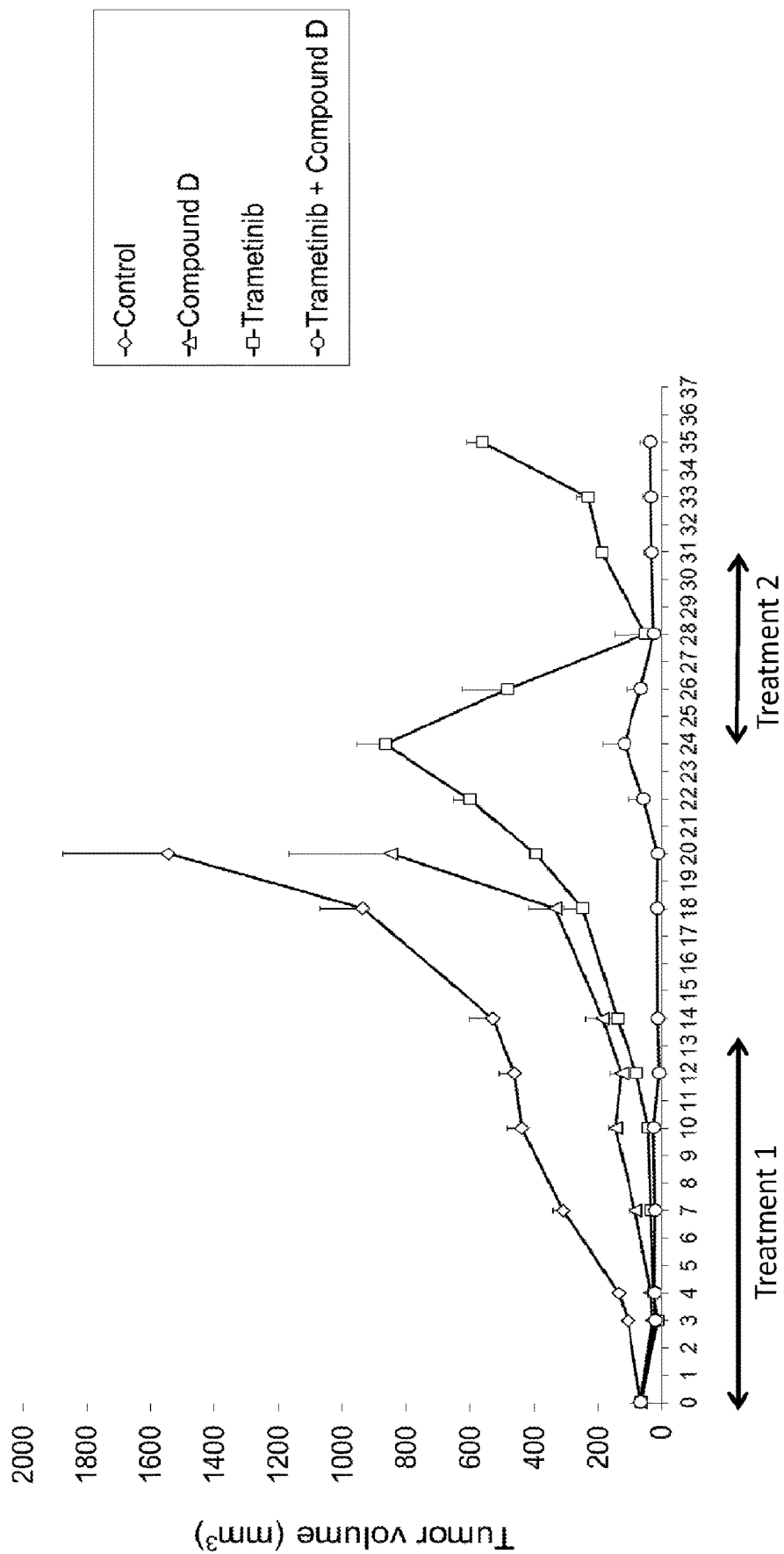
FIG. 12. Compound D synergizes with MEK inhibitor Trametinib to induce tumor regression in mice implanted with tumor from Adenoid Cyctic Carcinoma patient harboring mutation in BRAF. Mice were treated with (a) vehicle (◇); (b) Trametinib (□); (c) Compound D (Δ); or (d) Trametinib+Compound D (○). Treatments were initiated when average tumor size was ~65 mm$^3$. Treatment with Trametinib induced tumor regression, but while on treatment tumors progressed. Combined treatment of Trametinib and Compound D induced tumor regression and none of these tumors regrew while on treatment. The study included two phases of treatments day0-day13 and day24-day31.

As shown in FIG. 12, Treatment with Trametinib induced tumor regression, but while on treatment after day10 tumors progressed. Combined treatment of Trametinib and Compound D induced tumor regression and none of these tumors regrew while on treatment. A second phase treatment on days 24-31 induced dramatic tumor regression in all mice treated with Trametinib but the response was transient and after 4 days of treatment tumors acquired resistance to the treatment and aggressively progressed while on treatment. Second phase treatment with the Trametinib+Compound D combination induced tumor regression and none of these tumors regrew while on treatment.

Conclusion

Although the treatment of the initial tumor with Compound D alone led to moderate tumor growth inhibition, the combined treatment with Trametinib and Compound D led to dramatic tumor regression and the acquired resistance to Trametinib was abolished by Compound D. Evidence from the literature suggests that treatment with Trametinib induces IRS up-regulation leading to resistance by the activation of IGF1R/IRS-to-AKT survival pathway. Other reports claim Trametinib induces Stat3 phosphorylation in cancer cells leading to survival and acquired resistance to Trametinib. Without wishing to be bound by any particular theory or mechanism of action, Compound D and other compounds of formulae (I-IV) described herein are dual inhibitors of IRS1/2 and Stat3 and, therefore, should antagonize these Trametinib-induced feedback mechanisms and prevent resistance.

Example 10: Compound D Re-Sensitizes Gemcitabine-Resistant Tumors to Gemcitabine in Mice Implanted with Tumor from a Liver Metastasis of a Pancreatic Cancer Patient Experimental system: Patient-derived xenograft (PDX) of a biopsy of pancreatic cancer metastasis from the liver, subcutaneous implanted into NodScid mice.

I. Animals and Biopsy

Implantation of pancreatic cancer metastasis from the liver RA_160 tumor biopsy graft (P5) into NodScid mice for efficacy study: Several weeks following implantation of pancreatic cancer liver metastasis biopsy graft in mice, tumor cells (P5) were injected into NodScid mice (generated by in-house breeding), using the same procedure described above.

Onset of tumor growth (palpable tumor mass) was detected ten days following cell injection. A week later (on da0), 19 mice with average tumor size of 90 mm³ initiated treatments with Gemcitabine 25 mg/kg IP twice a week for 35 days. On day11 all tumors in Gemcitabine-treated mice regressed while the tumors in all 5 control mice progressed. On day21 the average tumor size in Gemcitabine-treated group was ~5 mm³ as compared to 1400 mm³ in the control group.

42 days following initiation of treatment with Gemcitabine resistance developed and regressed tumors progressed. Four days later 16 mice of the Gemcitabine-treated group with average tumor volume of ~110 mm³ were divided to two groups as follows.

II. Treatments

Treatment groups, following resistance to Gemcitabine has been acquired, included:
1. Gemcitabine 25 mg/kg IP twice a week
2. Gemcitabine 25 mg/kg IP+Compound D 70 mg/kg IV, twice a week.

The length (l) and the width (w) of the tumors were measured 2-4 times a week and the volumes of the tumors were calculated as follows: $v=lw^2/2$. Graphs represent average tumor volumes with standard errors (standard deviations/square root of group size). Mice weight and behavior were examined at least twice a week.

Results

Figure 13A:
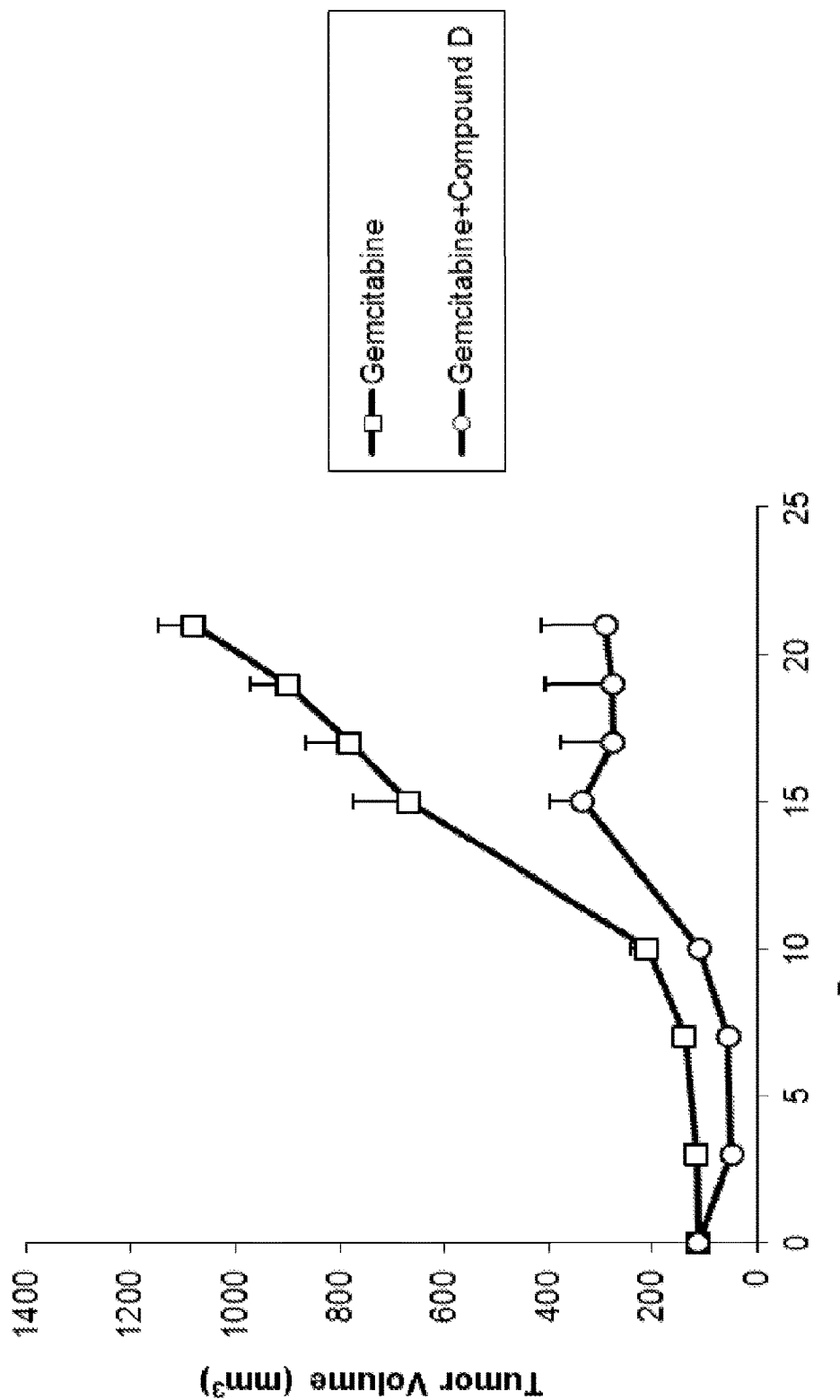
FIGS. 13A-13B. Compound D re-sensitizes Gemcitabine-resistant tumors to Gemcitabine in mice implanted with tumor from a liver metastasis of a pancreatic cancer patient. A. Mice were treated with Gemcitabine for 35 days and a week later regressed tumors acquired resistance to Gemcitabine and progressed. At this point when average tumor size was already ~110 mm$^3$ the Gemcitabine-treated mice were divided to two groups: (a) Gemcitabine (□); (b) Gemcitabine+Compound D (○). While all tumors treated with Gemcitabine progressed, combined treatment with Compound D+Gemcitabine led to tumor regression in half of the group and significant tumor growth inhibition in terms of average tumor size of the group compared to the Gemcitabine-treated group (p value=7.35*10$^{-5}$). B. At the end of the experiment, tumor pieces, similar in size, were cultured in plates (3 tumors per group) to test their viability and proliferative activity. Nine days later the plates were fixed and stained, showing massive proliferation in the Gemcitabine-treated tumors as opposed to a very low to negligible proliferative activity in the tumors from mice treated with Gemcitabine+Compound D.

Mice were treated with Gemcitabine for more than a month until regressed tumors acquired resistance to Gemcitabine and progressed. At this point the Gemcitabine-treated mice were divided to two groups (FIG. 13): (a) Gemcitabine (□); (b) Gemcitabine+Compound D (○). Treatments were initiated when average tumor size was ~110 mm³. While all tumors treated with Gemcitabine progressed, combined treatment with Compound D+Gemcitabine led to tumor regression in half of the group, and significant tumor growth inhibition in terms of average tumor size of the group compared to the Gemcitabine-treated group (FIG. 13A, p value=$7.35*10^{-5}$).

Figure 13B:
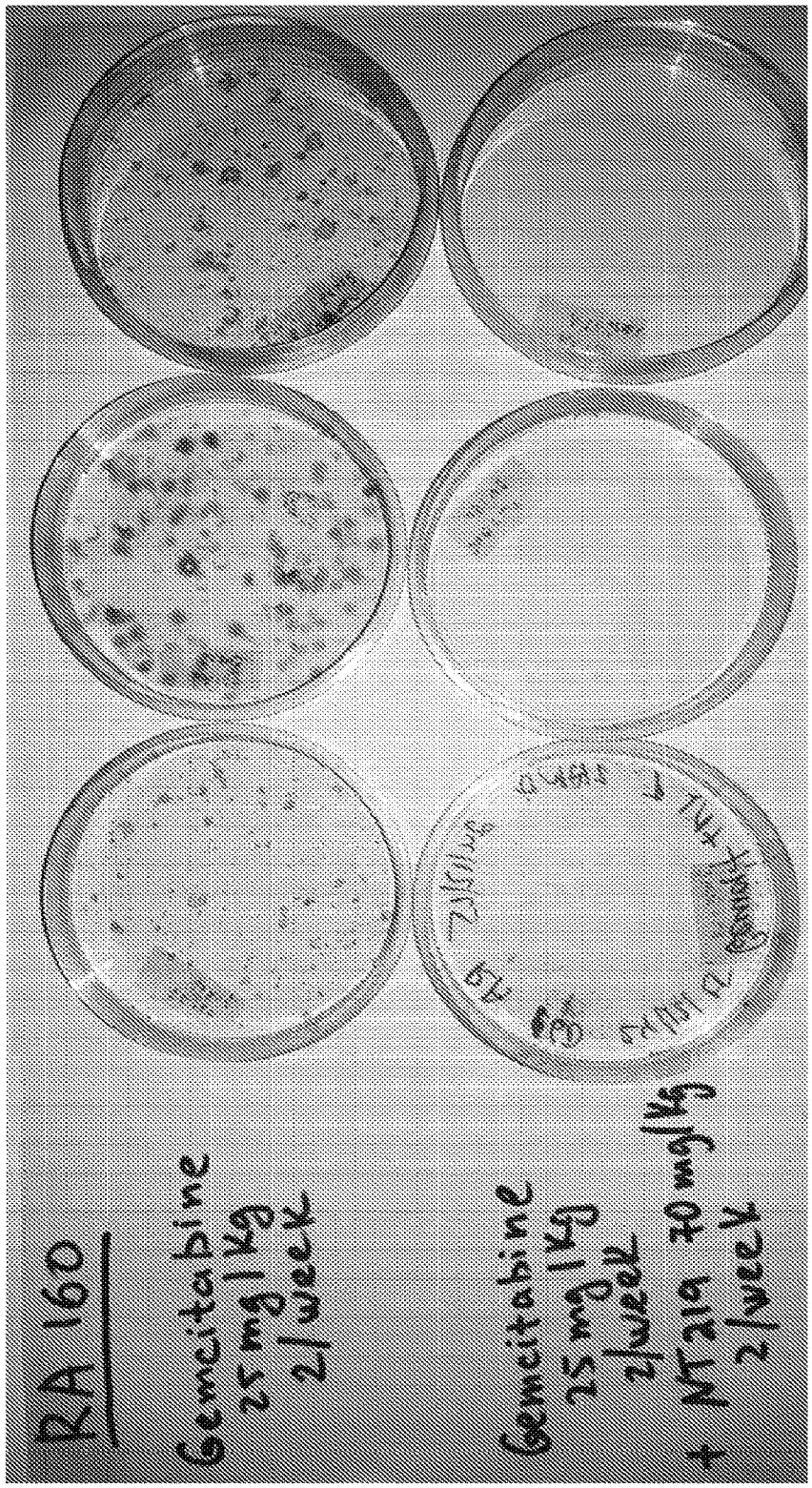

At the end of the experiment, tumor pieces, similar in size, from three tumors per group were cultured in separate plates to test their viability and proliferative activity. Nine days later the plates were fixed and stained, showing massive proliferation in the Gemcitabine-treated tumors as opposed to a very low to negligible proliferative activity in the tumors from mice treated with Gemcitabine+Compound D (FIG. 13B).

Conclusion

Compound D surprisingly synergized with chemotherapeutic drug Gemcitabine to combat resistance developed to Gemcitabine in pancreatic cancer.

Example 11: Compound D Prevents Acquired Resistance to Cetuximab in Mice Implanted with a Tumor from an Adnexal Adeno Carcinoma Metastatic Patient Experimental system: Patient-derived xenograft (PDX) of human primary Adnexal adeno metastatic carcinoma biopsy subcutaneous implanted into NodScid mice.

1. Animals and Biopsy

Biopsy: fresh human Adnexal adeno carcinoma metastatic (skin) biopsy (sample ID: RA-162)

Implantation of tumor biopsy grafts (P3) into NodScid mice for efficacy study: When tumors (P2) reached average size of about 1500 mm³, tumor tissue was injected into 50 male NodScid mice, generated by in-house breeding in the animal facilities of Bar Ilan University, at the same procedure described in example 1.

19 mice whose tumors reached average size of about 90 mm³ were included in the study.

The mice were divided into 4 groups and the following treatments initiated (day 0):
Control: Vehicle of NT219 (20% HPbCD) 50 µl IV twice a week—5 mice
Compound D 70 mg/kg IV twice a week—6 mice
Cetuximab 1 mg/mouse IP twice a week—5 mice
Cetuximab (1 mg/mouse IP)+Compound D (70 mg/kg IV), twice a week—3 mice In the combination group Cetuximab was administered ~4 hr following Compound D.

The length (l) and the width (w) of the tumors were measured 4 times a week and the volumes of the tumors were calculated as follows: $v=lw^2/2$. Graphs represent average tumor volumes with standard errors (standard deviations/square root of group size). Mice weight and behavior were examined at least once a week.

Results

Figure 14:
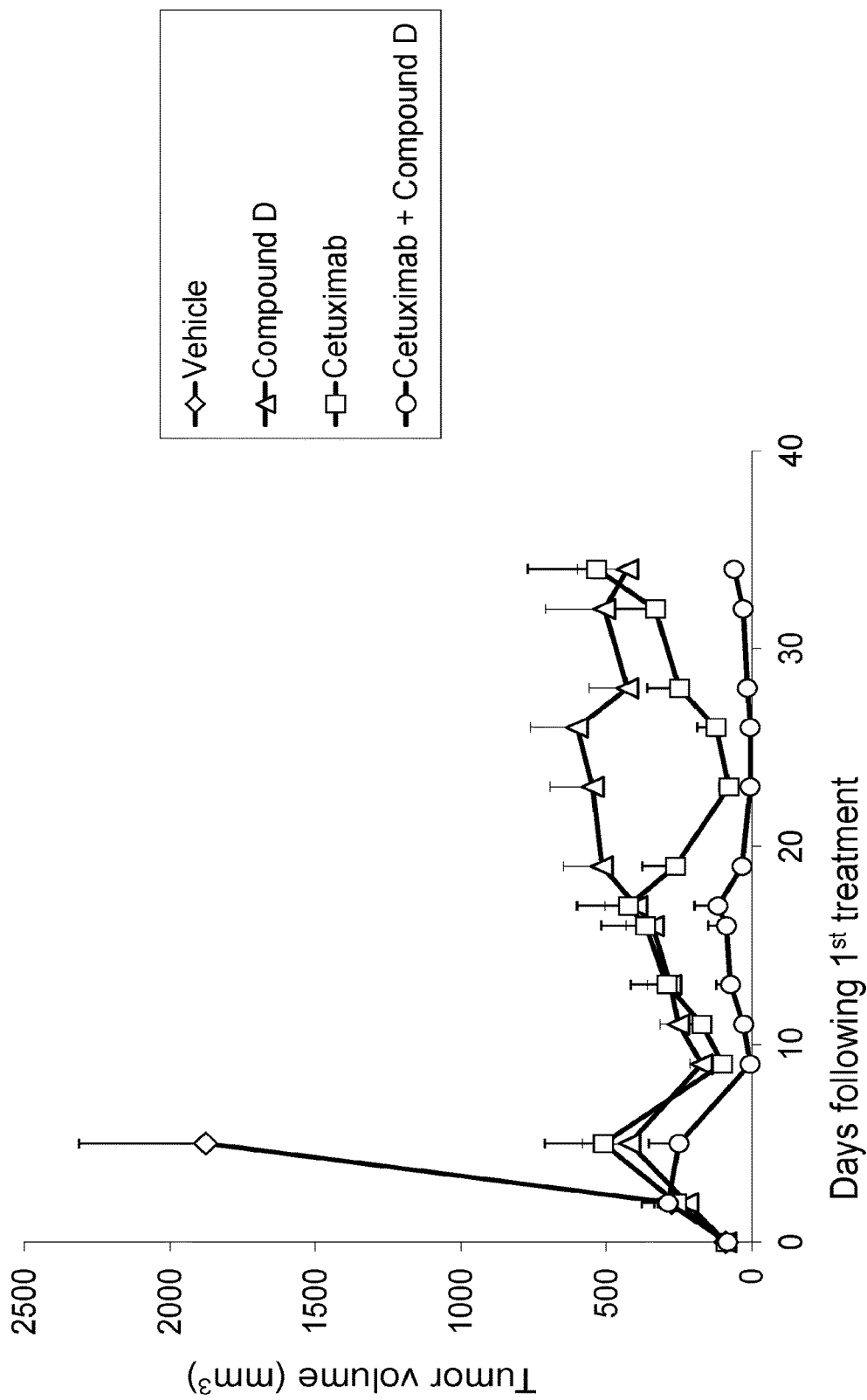
FIG. 14. Compound D prevents acquired resistance to Cetuximab in mice implanted with a tumor from an adnexal adeno carcinoma metastatic patient. Mice were treated for 32 days with (a) vehicle (◇); (b) Compound D (Δ); (c) Cetuximab (□); (d) Cetuximab+Compound D (○). Treatments were initiated when average tumor size was ~90 mm$^3$. Treatment with Cetuximab led to transient tumor growth attenuation followed by acquired resistance to Cetuximab, while the combined treatment of Cetuximab+Compound D induced tumor regression and prevented acquired resistance to Cetuximab.

After 5 days of treatment mice of the control group reached their endpoint (defined as tumor size above 1.5 cm³) (FIG. 14) and were sacrificed.

Treatment with Cetuximab led to transient tumor growth attenuation followed by acquired resistance to Cetuximab, and while on treatment tumors progressed (day 26 of treatment and onwards).

Combined treatment with Cetuximab+Compound D led to a significant tumor regression, and while the Cetuximab-treated group showed average tumor volume of >500 mm³—the average tumor volume of the combined treatment (Cetuximab+Compound D) was only 60 mm³ at the end of the experiment (day34).

Example 12

Compound D prevents acquired resistance to the combined treatment of Cetuximab and FOLFIRI (an approved treatment for colon cancer patients) in mice implanted with a tumor from a colon cancer patient. FOLFIRI contains the following regimen:
FOL—folinic acid (leucovorin), a vitamin B derivative used as a "rescue" drug for high doses of the drug methotrexate, but increases the cytotoxicity of 5-fluorouracil;
F—fluorouracil (5-FU), a pyrimidine analog and antimetabolite which incorporates into the DNA molecule and stops synthesis; and
IRI—irinotecan (Camptosar), a topoisomerase inhibitor, which prevents DNA from uncoiling and duplicating.

Experimental system: Patient-derived xenograft (PDX) of human primary colon metastatic carcinoma biopsy subcutaneous implanted into NodScid mice.

1. Animals and Biopsy
Biopsy: fresh human colon cancer biopsy (sample ID: RA-149)
Implantation of tumor biopsy grafts (P4) into NodScid mice for efficacy study: When tumors (P3) reached average size of about 1500 mm³, tumor tissue was injected into male NodScid mice, generated by in-house breeding in the animal facilities of Bar Ilan University, at the same procedure described in example 1.

36 mice whose tumors reached average size of about 110 mm³ were included in the study.

The mice were divided into 7 groups and the following treatments initiated (day 0):
Control: Vehicle of NT219 (20% HPbCD) 50 µl IV twice a week—5 mice
Compound D 70 mg/kg IV twice a week—5 mice
Cetuximab 1 mg/mouse IP twice a week—5 mice
FOLFIRI IP 5 times a week—5 mice
Cetuximab 1 mg/mouse IP twice a week+FOLFIRI IP 5 times a week—5 mice
Cetuximab 1 mg/mouse IP twice a week+FOLFIRI IP 5 times a week+Compound D 70 mg/kg IV twice a week—6 mice In the combination group Cetuximab was administered ~4 hr following Compound D.

In colon cancer Cetuximab is not effective as a standalone therapy, therefore it is approved for patients in combination with chemotherapy like FOLFIRI. FOLFIRI includes folinic acid (leucoverin), 5FU and Irinotecan.

The length (l) and the width (w) of the tumors were measured 4 times a week and the volume of the tumors were calculated as follows: $v=lw^2/2$. Graphs represent average tumor volumes with standard errors (standard deviations/square root of group size). Mice weight and behavior were examined at least once a week.

Results

No effect on tumor growth was detected in the group treated by either Cetuximab, Compound D or FOLFIRI alone. But the combination of Cetuximab with FOLFIRI with or without Compound D led to a significant regression of the tumors (FIG. 15).

Figure 15:
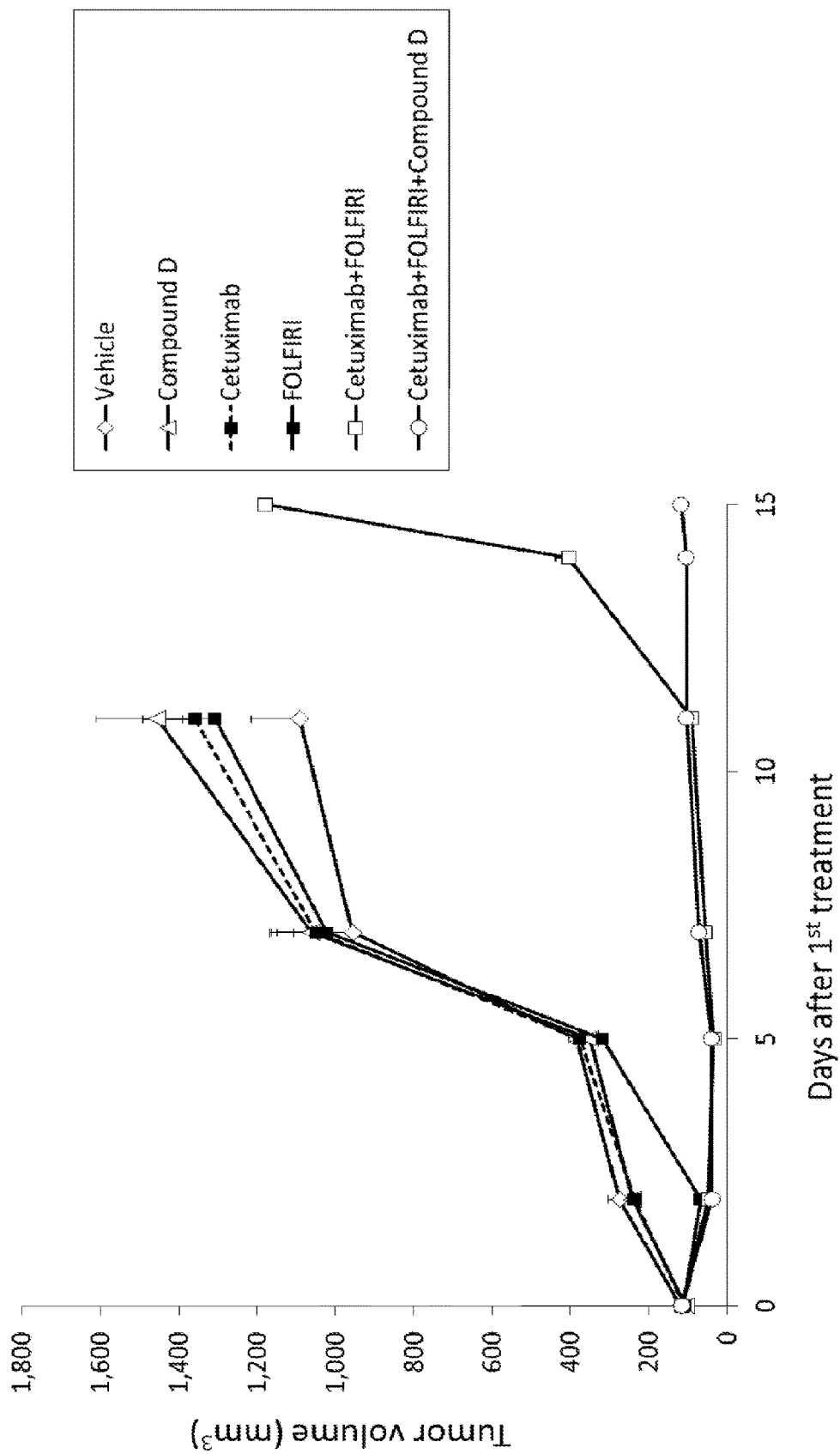
FIG. 15. Compound D prevents acquired resistance to the combined treatment of Cetuximab and FOLFIRI (an approved treatment for colon cancer patients) in mice implanted with a tumor from a colon cancer patient. Mice were treated for 14 days with (a) vehicle (◇); (b) Compound D (Δ); (c) Cetuximab+FOLFIRI (□); (d) Cetuximab+FOLFIRI+Compound D (○); (e) FOLFIRI (■); and (f) Cetuximab (■, dashed line). Treatments were initiated when average tumor size was ~110 mm$^3$. Combined treatment of Cetuximab+FOLFIRI with or without Compound D induced tumor regression at the first week of treatment. While all tumors in mice treated with Cetuximab+FOLFIRI developed resistance to the treatment during the second week of treatment and aggressively progressed, the combined treatment with Compound D prevented acquired resistance to Cetuximab+FOLFIRI.

Following 12 days of treatment the tumors of the Cetuximab+FOLFIRI group developed resistance to the treatment and progressed, while the tumors of the Cetuximab+FOLFIRI+Compound D group regressed and haven't acquired resistance to the treatment (FIG. 15).

Conclusions

The FDA has approved Cetuximab (Erbitux) in combination with FOLFIRI regimen as a first-line treatment for patients with metastatic colorectal cancer who test negative for the KRAS mutation. Cetuximab as a monotherapy in colorectal cancer is usually not effective. The colon cancer PDX model of RA_149 biopsy is in accordance with the clinical condition—Cetuximab as a monotherapy is not effective but with chemotherapy like FOLFIRI it induces dramatic tumor regression. In addition, as unfortunately seen with patients, resistance is acquired and tumors progress. We show that combining this therapy with Compound D prevents acquired resistance to Cetuximab+FOLFIRI, extending the positive response.

While certain embodiments of the invention have been illustrated and described, it will be clear that the invention is not limited to the embodiments described herein. Numerous modifications, changes, variations, substitutions and equivalents will be apparent to those skilled in the art without departing from the spirit and scope of the present invention as described by the claims, which follow.

What is claimed is:

1. A method of treating a subject having a tumor with acquired resistance to treatment with an EGFR inhibitor and/or EGFR antibody, the method comprising administering to the subject a compound represented by the structure of formula D:

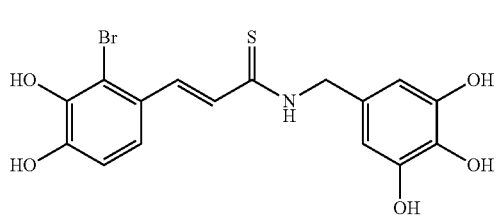

including salts and hydrates thereof;
in combination with an EGFR antibody selected from the group consisting of cetuximab, panitumumab, and necitumumab, wherein the treatment results in attenuation or regression in the growth of the tumor with acquired resistance to EGFR inhibitor and/or EGFR antibody treatment, and wherein the compound represented by the structure of formula (D) and the EGFR antibody are administered in separate pharmaceutical compositions.

2. The method according to claim 1, wherein the tumor is present in a cancer patient who is receiving treatment with an EGFR inhibitor and/or EGFR antibody or is a candidate for receiving such treatment.

3. The method according to claim 1, wherein the tumor is present in a patient having a cancer selected from the group consisting of head and neck (H&N) cancer, sarcoma, multiple myeloma, ovarian cancer, breast cancer, kidney cancer, hematopoietic cancer, lung carcinoma, melanoma, glioblastoma, hepatocarcinoma, prostate cancer, thyroid cancer, esophageal carcinoma, stomach cancer, and colon cancer.

4. The method according to claim 3, wherein the tumor is present in a patient having head and neck (H&N) cancer, thyroid cancer, esophageal carcinoma, stomach cancer, or colon cancer.

5. The method according to claim 3, wherein the tumor is present in a patient having hematopoietic cancer, wherein the hematopoietic cancer is lymphoma or leukemia.

6. The method according to claim 1, wherein the compound represented by the structure of formula (D) is in a form suitable for oral administration, intravenous administration, topical administration, administration by inhalation, or administration via a suppository; and wherein the EGFR antibody is in a form suitable for intravenous administration.

7. The method according to claim 1, wherein the compound represented by the structure of formula (D) is formulated in a solution, a suspension, a syrup, an emulsion, a dispersion, a tablet, a pill, a capsule, a pellet, granules, a powder, an ointment, a gel, or a cream; and wherein the EGFR antibody is formulated in a solution or a suspension.

8. The method according to claim 1, wherein the EGFR antibody is cetuximab.

9. A method of preventing or delaying tumor recurrence following cessation of treatment with an EGFR inhibitor and/or EGFR antibody, the method comprising administering to the subject following cessation of treatment with an EGFR inhibitor and/or EGFR antibody a compound represented by the structure of formula D:

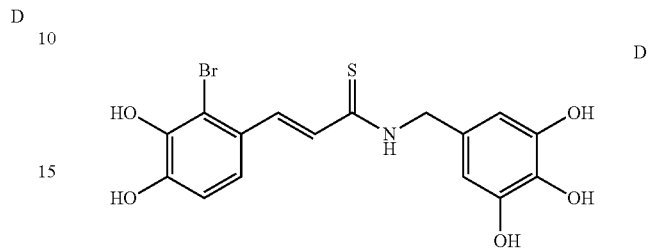

including salts and hydrates thereof;
in combination with an EGFR antibody selected from the group consisting of cetuximab, panitumumab, and necitumumab, wherein the compound represented by the structure of formula (D) and the EGFR antibody are administered in separate pharmaceutical compositions.

10. The method according to claim 9, wherein the EGFR antibody is cetuximab.

11. The method according to claim 9, wherein the tumor is present in a cancer patient who has received treatment with an EGFR inhibitor and/or EGFR antibody.

12. The method according to claim 9, wherein the tumor is present in a patient having a cancer selected from the group consisting of head and neck (H&N) cancer, sarcoma, multiple myeloma, ovarian cancer, breast cancer, kidney cancer, hematopoietic cancer, lung carcinoma, melanoma, glioblastoma, hepatocarcinoma, prostate cancer, thyroid cancer, esophageal carcinoma, stomach cancer, and colon cancer.

13. The method according to claim 12, wherein the tumor is present in a patient having head and neck (H&N) cancer, thyroid cancer, esophageal carcinoma, stomach cancer, or colon cancer.

14. The method according to claim 12, wherein the tumor is present in a patient having hematopoietic cancer, wherein the hematopoietic cancer is lymphoma or leukemia.

15. The method according to claim 9, wherein the compound represented by the structure of formula (D) is in a form suitable for oral administration, intravenous administration, topical administration, administration by inhalation, or administration via a suppository; and wherein the EGFR antibody is in a form suitable for intravenous administration.

16. The method according to claim 9, wherein the compound represented by the structure of formula (D) is formulated in a solution, a suspension, a syrup, an emulsion, a dispersion, a tablet, a pill, a capsule, a pellet, granules, a powder, an ointment, a gel, or a cream; and wherein the EGFR antibody is formulated in a solution or a suspension.

* * * * *